United States Patent
Kubota et al.

(10) Patent No.: US 7,709,230 B2
(45) Date of Patent: May 4, 2010

(54) PROCESS FOR PRODUCING ISOMALTOSE AND USES THEREOF

(75) Inventors: Michio Kubota, Okayama (JP);
Tomoyuki Nishimoto, Okayama (JP);
Takanobu Higashiyama, Okayama (JP);
Hikaru Watanabe, Okayama (JP);
Shigeharu Fukuda, Okayama (JP);
Toshio Miyake, Okayama (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 0 days.

(21) Appl. No.: 11/777,044

(22) Filed: Jul. 12, 2007

(65) Prior Publication Data

US 2008/0241904 A1 Oct. 2, 2008

Related U.S. Application Data

(63) Continuation-in-part of application No. 10/363,556, filed as application No. PCT/JP02/04166 on Apr. 25, 2002, now abandoned.

(30) Foreign Application Priority Data

Apr. 27, 2001 (JP) .............................. 2001-130922

(51) Int. Cl.
*C12P 19/44* (2006.01)
*C12P 19/18* (2006.01)
*C12P 19/04* (2006.01)
*C12N 9/00* (2006.01)
*C12N 9/10* (2006.01)
*C12P 21/06* (2006.01)
*C07H 1/00* (2006.01)

(52) U.S. Cl. ........................... 435/74; 435/97; 435/101; 435/183; 435/193; 435/69.1; 435/91.1; 536/123.12

(58) Field of Classification Search ...................... None
See application file for complete search history.

(56) References Cited

U.S. PATENT DOCUMENTS

| 4,521,252 A * | 6/1985 | Miyake et al. ............. 127/46.3 |
| RE33,047 E | 9/1989 | Miyake et al. |
| 6,025,168 A * | 2/2000 | Vercauteren et al. .......... 435/97 |
| 2005/0009017 A1* | 1/2005 | Kubota et al. .................. 435/6 |

FOREIGN PATENT DOCUMENTS

| EP | 0 608 635 A | 8/1994 |
| EP | 0 875 585 A | 11/1998 |
| EP | 0 990 704 | 4/2000 |
| JP | 23799/83 | 2/1983 |
| JP | 72598/83 | 4/1983 |
| JP | 63-216493 | 9/1988 |
| JP | 63-287495 | 11/1988 |
| JP | 234937/00 | 2/2002 |
| JP | 350142/00 | 5/2002 |
| WO | WO 99/27124 A | 6/1999 |
| WO | WO 01/90338 | * 11/2001 |
| WO | WO 02/10361 | 2/2002 |
| WO | WO 02/40659 | 5/2002 |
| WO | WO 02/055708 | 7/2002 |

OTHER PUBLICATIONS

Broun et al., Catalytic plasticity of fatty acid modification enzymes underlying chemical diversity of plant lipids. Science, 1998, vol. 282: 1315-1317.*
Kisselev L., Polypeptide release factors in prokaryotes and eukaryotes: same function, different structure. Structure, 2002, vol. 10: 8-9.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a malonyl decarboxylase by replacemnt of the active-site cysteine with glutamine. Biochemistry, 1999, vol. 38: 11643-11650.*
Seffernick et al., Melamine deaminase and atrazine chlorohydrolase: 98 percent identical but functionally different. J. Bacteriol., 2001, vol. 183 (8): 2405-2410.*
Hayashi et al., The enzymatic reaction for the production of panose and isomaltose by glycosyltransferase from Aureobasidium. Lett. Appl. Mirobiol., 1994, vol. 19: 247-248.*
Yun et al., Continuous production of isomalto-oligosaccharides from maltose syrup by immobilized cells of permeabilized Aureobasidium pullulans. Biotech. Lettt., 1994, vol. 16 (11): 1145-1150.*
Torii et al., Degradation of alpha-linked D-gluco-oligosaccharides and dextrans by an isomalto-dextranase preparation from Arthobacter globiformis T6. Biochem. Biophys. Res. Commun., 1976, vol. 70 (2): 459-464.*
Kim et al: "Enzymatic Preparation of Novel Non-Reducing Oligosaccharides Having An Isomaltosyl Residue by Using the Arthobacter Globiformis T6" Bioscience, Biotechnology and Biochemistry, vol. 59, No. 7, 1995, pp. 1367-1369.
Cote et al., "Enzymatically produced cyclic α-1, 3-linked and α-1, 6-linked oligosaccharides of D-glucose," *Eur. J. Biochem.*, 226: 641-648, (1994).

(Continued)

*Primary Examiner*—Ganapathirama Raghu
(74) *Attorney, Agent, or Firm*—Browdy and Neimark, PLLC

(57) ABSTRACT

A novel process for producing isomaltose and uses thereof and comprising the steps of contacting saccharides, which have a glucose polymerization degree of at least two and α-1,4 glucosidic linkage as a linkage at the non-reducing end, with an α-isomaltosylglucosaccharide-forming enzyme, in the presence or the absence of α-isomaltosyl-transferring enzyme to form a-isomaltosylglucosaccharides, which have a glucose polymerization degree of at least three, α-1,6 glucosidic linkage as a linkage at the non-reducing end, and α-1,4 glucosidic linkage as a linkage other than the non-reducing end, and/or to form cyclo{→6)-α-D-glucopyranosyl-(1→3)-α-D-glucopyranosyl-(1→6)-α-D-glucopyranosyl-(1→3)-α-D-glucopyranosyl-(1→)}; contacting the saccharides so formed with isomaltose-releasing enzyme to release isomaltose; and collecting the released isomaltose; and uses thereof.

7 Claims, 22 Drawing Sheets

OTHER PUBLICATIONS

Sawai et al. "Purification and Some Properties of the Isomaltodexranse of *Actinomadura* Strain R10 and Comparison with that *Arthrobacter globiformis Arthrobacter globiformis* T6" *Carbohydrate Research* 89: 289-299, (1981).

Sawai et at "A Bacterial Dextranase Releasing Only Isomaltose form Dextrans" *J Biochem* 75: 105-112, (1974).

Hayashi et al., "The enzymatic reaction for the production of panose and isomaltose by glucosyltransferase from *Aureobasidium*," *Letters in Applied Microbiology* 19:247-248, (1994).

* cited by examiner

PROCESS FOR PRODUCING ISOMALTOSE AND USES THEREOF

CROSS-REFERENCE TO RELATED APPLICATIONS

This application is a continuation in part of application Ser. No. 10/363,556, which was filed as a 371 of PCT/JP02/04166, the entire contents of which are hereby incorporated by reference.

TECHNICAL FIELD

The present invention relates to a novel process for producing isomaltose and uses thereof, more particularly, a process for producing isomaltose from saccharides, which have both a glucose polymerization degree of at least two and an α-1,4 glucosidic linkage as a linkage at the non-reducing end, in a relatively high yield.

BACKGROUND ART

Isomaltose is a substantially non-crystallizable saccharide which is present in small quantities in fermented foods and has a relatively low sweetness and satisfactory humectancy. The saccharide has been widely used in a mixture form with saccharides such as glucose, maltose and panose in foods, cosmetics, pharmaceuticals, etc.

Isomaltose is a rare saccharide present in small quantities in fermented foods, etc., in the natural world. On an industrial-scale production, the following methods for producing isomaltose have been known; partial hydrolysis reaction of dextrans using acid catalysts, enzymatic reactions using dextranase or isomaltodextranase, etc., reverse synthetic reactions from glucose using glucoamylase or acid catalysts, and glucose saccharide-transferring reactions from maltose or maltodextrins using α-glucosidase. However, the isomaltose content of reaction mixtures obtained by conventional methods is only about 10 to about 25% (w/w), on a dry solid basis (d.s.b.) (throughout the specification, "% (w/w)" is abbreviated as "%", unless specified otherwise), and therefore it is far from satisfactory in view of the purity of isomaltose on an industrial-scale production. As a method for improving the drawback, one can use column chromatography, as disclosed in Japanese Patent Kokai No. 72,598/83. According to the disclosed method, a high purity isomaltose is obtained from a material saccharide solution with an isomaltose content of about 10 to about 25%, d.s.b. However, the method has the drawback that the purity and yield of isomaltose inevitably depends on the isomaltose content in the material saccharide solutions used.

Under this background, there has been a great demand for a novel process for producing isomaltose on an industrial scale, at a lower cost, and in a relatively high yield.

In view of the prior arts, the object of the present invention is to establish a process for producing isomaltose which produces isomaltose on an industrial scale, at a lower cost, and in a relatively high yield.

DISCLOSURE OF INVENTION

During the present inventors' energetic studying to solve the above object, it has reported in *European Journal of Biochemistry*, Vol. 226, pp. 641-648 (1994) a cyclic tetrasaccharide having the structure of cyclo{→6)-α-D-glucopyranosyl-(1→3)-α-D-glucopyranosyl-(1→6)-α-D-glucopyranosyl-(1→3)-α-D-glucopyranosyl-(1→} (abbreviated as "cyclotetrasaccharide" throughout the specification), formed by allowing a hydrolyzing enzyme, i.e., alternanase, to act on alternan linked with glucose residues via the alternating α-1,3 and α-1,6 linkages.

In U.S. Published Application 2005/0009017 A1, the present inventors disclosed a process for producing cyclotetrasaccharide using an α-isomaltosyl-transferring enzyme which forms cyclotetrasaccharide from α-isomaltosylglucosaccharides such as panose derived from starches. U.S. Published Application 2003/0194762 A1 discloses a process for producing cyclotetrasaccharide in a satisfactorily high yield by allowing the above α-isomaltosyl-transferring enzyme and an α-isomaltosylglucosaccharide-forming enzyme which forms α-isomaltosylglucosaccharide from maltooligosaccharides.

Thereafter, the present inventors focused on the fact that the above α-isomaltosylglucosaccharide and cyclotetrasaccharide have an isomaltose structure intramolecularly, and then studied a method for producing isomaltose from these saccharides. As the result of studying on the enzymatic reaction mechanisms of the above α-isomaltosylglucosaccharide-forming enzyme and α-isomaltosyl-transferring enzyme, the present inventors found that the production yield of isomaltose is outstandingly improved by allowing α-isomaltosylglucosaccharide-forming enzyme and isomaltose-releasing enzyme capable of releasing isomaltose, in the presence or the absence of α-isomaltosyl-transferring enzyme, to act on saccharides having both a glucose polymerization degree of at least two and α-1,4 glucosidic linkage as a linkage at the non-reducing end; and found that the method is easily feasible on an industrial scale. The present inventors also established the uses of isomaltose thus obtained, and accomplished this invention:

They accomplished the following process and uses thereof and solved the object of the present invention; a process for producing isomaltose characterized in that it comprises the steps of allowing α-isomaltosylglucosaccharide-forming enzyme, in the presence or the absence of α-isomaltosyl-transferring enzyme, to act on saccharides, which have both a glucose polymerization degree of at least two and α-1,4 glucosidic linkage as a linkage at the non-reducing end, to form α-isomaltosylglucosaccharides, which have a glucose polymerizaton degree of at least three, α-1,6 glucosidic linkage as a linkage at the non-reducing end, and α-1,4 glucosidic linkage as a linkage other than the non-reducing end, and/or to form cyclo{→6)-α-D-glucopyranosyl-(1→3)-α-D-glucopyranosyl-(1→6)-α-D-glucopyranosyl-(1→3)-α-D-glucopyranosyl-(1→}; allowing isomaltose-releasing enzyme to act on the formed saccharide(s) to release isomaltose; and collecting the released isomaltose.

BEST MODE FOR CARRYING OUT THE INVENTION

Figure 1:
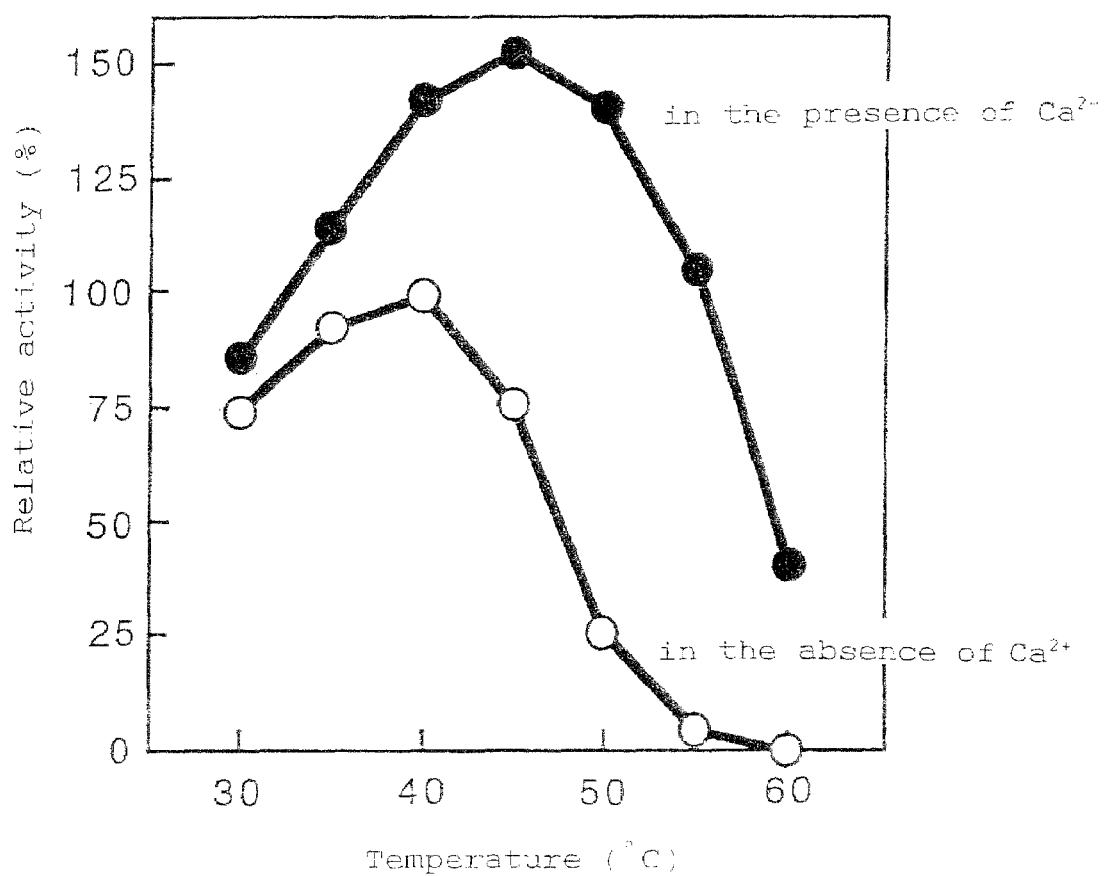
FIG. 1 shows the thermal influence on the enzymatic activity of α-isomaltosylglucosaccharide-forming enzyme from a microorganism of *Bacillus globiformis* C9 strain.

The α-isomaltosylglucosaccharide-forming enzyme used in the process claimed herein means an enzyme which forms α-isomaltosylglucosaccharides such as α-isomaltosylglucose (also known as panose), α-isomaltosylmaltose, α-isomaltosylmaltotriose, and α-isomaltosylmaltotetraose from amylaceous substances. These enzymes include, for example, an α-isomaltosylglucosaccharide-forming enzyme from *Bacillus globisporus* C9, FERM BP-7143 (hereinafter designated as "Strain C9"), and *Bacillus globisporus* C11, FERM BP-7144 (hereinafter designated as "Strain C11"), which strains were deposited on Apr. 25, 2000, in International Patent Organism Depositary National Institute of Advanced Industrial Science and Technology Tsukuba Central 6, 1-1, Higashi 1-Chome Tsukuba-shi, Ibaraki-ken, 305-8566, Japan. These strains are disclosed in U.S. Published Application 2003/0194762 A1; and recombinant polypeptides having an α-isomaltosylglucosaccharide-forming enzyme activity, as disclosed in U.S. Published Application 2004/0161835 A1. Additionally, α-isomaltosylglucosaccharide-forming enzymes from *Bacillus globisporus* N75, FERM BP-7591 and *Arthrobacter globiformis* A19, FERM BP-7690, disclosed in U.S. Published Application 2003/0194762 A1, can be used in the process claimed herein.

The α-isomaltosyl-transferring enzyme for use in the present invention means an enzyme which forms cyclotetrasaccharide from α-isomaltosylglucosaccharides such as panose and α-isomaltosylmaltose. Examples of such enzymes include an α-isomaltosyl-transferring enzyme from *Bacillus globisporus* C9, FERM BP-7143, *Bacillus globisporus* C11, FERM BP-7144, *Bacillus globisporus* N 75, FERM BP-7591 and *Arthrobacter ramosus* S1, FERM BP-7592, disclosed in U.S. Published Application 2005/0009017 A1; and recombinant polypeptides having an α-isomaltosyl-transferring enzyme activity, as disclosed in U.S. Published Application 2004/0121431 A1.

The isomaltose-releasing enzyme that can be used in the present invention means an enzyme, which has an activity of releasing isomaltose from α-isomaltosylglucosaccharides or cyclotetrasaccharide, for example, isomaltodextranase (EC 3.2.1.94) from microorganisms such as *Arthrobacter globiformis* T6, NRRL B-4425, reported in *Journal of Biochemistry*, Vol. 75, pp. 105-112 (1974); *Arthrobacter globiformis*, IAM 12103, provided from Institute of Applied Microbiology (IAM), The University of Tokyo, Tokyo, Japan; and *Actinomadura R*10, NRRL B-11411, reported in *Carbohydrate Research*, Vol. 89, pp. 289-299 (1981).

The saccharides, which have both a glucose polymerization degree of at least two and α-1,4 glucosidic linkage as a linkage at the non-reducing end, which can be used in the present invention include, for example, terrestrial starches such as corn, rice, and wheat; and subterranean starches such as potatoes, sweet potatoes, and tapioca, as well as partial hydrolyzates thereof, i.e., partial starch hydrolyzates thereof. The partial starch hydrolyzates can be usually prepared by suspending the above terrestrial or subterranean starches in water, usually, into 10%, preferably, 15-65%, more preferably, 20-50% starch suspensions, and then liquefying the suspensions by heating or using acid agents or enzyme preparations. The degree of liquefaction is preferably set to a relatively low level, usually, less than DE (dextrose equivalent) 15, preferably, less than DE 10, and more preferably, DE 0.1-9.

In the case of liquefaction with acid agents, there employed is a method comprising a step of liquefying the above starches with acid agents such as hydrochloric acid, phosphoric acid, and oxalic acid, and usually neutralizing the liquefied suspensions to the desired pHs with alkaline agents such as calcium carbonate, calcium oxide, and sodium carbonate. While in the case of liquefaction with enzyme preparations, α-amylases, particularly, thermostable liquefying α-amylases are preferably used in the present invention.

Isomaltose can be obtained in a relatively high yield by allowing α-isomaltosylglucosaccharide-forming enzyme, in the presence or the absence of α-isomaltosyl-transferring enzyme, to act on saccharides, which have both a glucose polymerization degree of at least two and α-1,4 glucosidic linkage as a linkage at the non-reducing end, to form α-isomaltosylglucosaccharides, which have a glucose polymerization degree of at least three, α-1,6 glucosidic linkage as a linkage at the non-reducing end, and α-1,4 glucosidic linkage as a linkage other than the non-reducing end, and/or to form cyclo{→6)-α-D-glucopyranosyl-(1→3)-α-D-glucopyranosyl-(1→6)-α-D-glucopyranosyl-(1→3)-α-D-glucopyranosyl-(1→}; allowing isomaltosyl-releasing enzymes to act on the products to form isomaltose; and collecting the formed isomaltose. When allowed to act on substrates, α-isomaltosylglucosaccharide-forming enzyme can be used in combination with one or more another enzymes of α-isomaltosyl-transferring enzyme, cyclomaltodextrin glucanotransferase (hereinafter abbreviated as "CGTase"), α-glucosidase, glucoamylase, and starch debranching enzymes such as isoamylase and pullulanase to further increase the yield of isomaltose. Particularly, the yield of isomaltose from cyclotetrasaccharide can be increased up to a maximum yield of 100% in such a manner by allowing isomaltose-releasing enzyme to act on cyclotetrasaccharide obtained by allowing α-isomaltosylglucosaccharide-forming enzyme, in the presence of α-isomaltosyl-transferring enzyme, to act on saccharides having both a glucose polymerization degree of at least two and α-1,4 glucosidic linkage as a linkage at the non-reducing end. The order of a plurality of enzymes employed in the present invention can be decided depending on the yield of isomaltose, reaction times, reaction conditions, etc. These enzymes can be allowed to act on substrates at the same time or different timings after divided into several aliquots with the desired amount. Any pHs at which the enzymes used in the present invention are allowed to act on their substrates can be employed as long as the enzymes exert their enzymatic activities at the pHs, usually, those which are selected from pH 4-10, preferably, pH 5-8. The temperatures of allowing enzymes are usually selected from 10-80° C., preferably, 30-70° C.

The amount of enzymes used can be appropriately altered in view of the reaction condition and time for each enzyme: Usually, the amounts of α-isomaltosyl-transferring enzyme and α-isomaltosylglucosaccharide-forming enzyme used are respectively selected from 0.01-100 units, the amounts of isomaltose-releasing enzyme and starch debranching enzyme used are selected from 1-10,000 units, and the amounts of CGTase, α-glucosidase, glucoamylase, and isoamylase used are selected from 0.05-7,000 units. Although the reaction time of enzymes used varies depending on their amounts used, it is appropriately selected in view of the yield of isomaltose. Usually, the reaction time is set to 1-200 hours, preferably, 5-150 hours, and more preferably, 10-100 hours to complete the overall enzymatic reactions. The pHs and temperatures in the enzymatic reaction for each enzyme can be appropriately altered before termination of the enzymatic reactions of the present invention.

The content of isomaltose in the enzymatic reaction mixtures thus obtained is usually, on a dry solid basis, at least 30%, preferably, at least 40%, more preferably, at least 50%, and still more preferably, up to a maximum level of 99% or higher. Particularly, when α-isomaltosylglucosaccharide-forming enzyme, α-isomaltosyl-transferring enzyme, and isomaltose-releasing enzyme are simultaneously or in this order added to and allowed to act on saccharides having both a glucose polymerization degree of at least two and α-1,4 glucosidic linkage as a linkage at the non-reducing end, enzymatic reaction mixtures with an isomaltose content of at least 50%, d.s.b., can be easily obtained. In general, the reaction mixtures can be subjected to conventional methods such as filtration and centrifugation to remove impurities; decolored with an activated charcoal, desalted and purified, for example, by ion-exchange resins in a H— or OH-form; and concentrated into syrupy products; and optionally dried into powdery products. If necessary, the resulting products can be further purified into high isomaltose content products by appropriately using alone or in combination with two or more methods of column chromatography such as ion-exchange column chromatography, column chromatography using activated charcoal, and silica gel column chromatography; separation using organic solvents such as alcohols and acetone; and membrane separation. In particular, as an industrial-scale production method for high isomaltose content product, ion-exchange column chromatography is preferably employed. For example, high isomaltose content products can be produced on an industrial scale at a relatively high yield and amount and at a lesser cost by ion-exchange column chromatography using one or more styrene-divinylbenzene cross-linked copolymeric resins with sulfonyl group and strong-acid cation exchange resins in the form of alkaline metals such as $Na^+$ and $K^+$, and of alkaline earth metals such as $Ca^{2+}$ and $Mg^{2+}$, as disclosed in Japanese Patent Kokai Nos. 23,799/83 and 72,598/83. Examples of commercialized products of the above strong-acid cation exchange resins include "DOWEX 50WX2", "DOWEX 50WX4", and "DOWEX 50WX8", produced by Dow Chemical Co., Midland, Mich., USA; "AMBERLITE CG-120", produced by Rohm & Hass Company, Philadelphia, Pa., USA; "XT-1022E" produced by Tokyo Organic Chemical Industries, Ltd., Tokyo, Japan; and "DIAION SK1B", "DIAION SK102", and "DIAION SK104", produced by Mitsubishi Chemical Industries, Tokyo, Japan. In practicing the above ion-exchange column chromatography, any one of fixed-bed, moving bed, and semi-moving bed methods can be appropriately used. With these methods the purity of isomaltose can be increased, usually, to at least 60%, preferably, at least 80%, and more preferably, at least 99%, d.s.b., as the highest possible purity. Products of isomaltose except for the highest possible isomaltose, i.e., high isomaltose content products usually contain isomaltose and 1-60%, d.s.b., of one or more saccharides from glucose, maltose, maltotriose, maltotetraose, other starch hydrolyzates, α-isomaltosylglucosaccharides, and α-glucosyl-(1→6)-α-glucosyl-(1→3)-α-glucosyl-(1→6)-α-glucose (may be abbreviated as "open-ring tetrasaccharide", hereinafter).

The isomaltose and high isomaltose content products thus obtained can be suitably used as sweeteners which substantially do not induce dental caries because of their action of inhibiting the formation of dextran, a cause of dental caries, as well as satisfactory quality and good tasting sweetness. The isomaltose and high isomaltose content products of the present invention have also satisfactory storage stability. Particularly, products with a relatively high content of crystalline isomaltose can be advantageously used as sugar coatings for tablets in combination with conventional binders such as pullulan, hydroxyethyl starch, and polyvinylpyrrolidone. The isomaltose and high isomaltose content products of the present invention have useful properties of osmosis-controlling ability, filler-imparting ability, gloss-imparting ability, humectancy, viscosity, crystallization-preventing ability for saccharides, insubstantial fermentability, retrogradation-preventing ability for gelatinized starches, etc. Thus, the isomaltose and high isomaltose content products can be arbitrarily used as a sweetener, taste-improving agent, flavor-improving agent, quality-improving agent, stabilizer, excipient, filler, etc., in a variety of compositions such as food products, feeds, pet foods, cosmetics, pharmaceuticals, tobaccos, and cigarettes.

The isomaltose and high isomaltose content products of the present invention can be used as seasonings to sweeten food products, and if necessary, they can be arbitrarily used in combination with one or more other sweeteners such as powdered syrup, glucose, fructose, lactosucrose, maltose, sucrose, isomerized sugar, honey, maple sugar, isomaltooligosaccharides, galactooligosaccharides, fructooligosaccharides, sorbitol, maltitol, lactitol, dihydrochalcone, stevioside, α-glycosyl stevioside, sweetener of *Momordica grosvenori*, glycyrrhizin, L-aspartyl L-phenylalanine methyl ester, sucralose, acesulfame K, saccharin, glycine, and alanine; and fillers such as dextrins, starches, and lactose.

Particularly, the isomaltose and high isomaltose content products of the present invention can be arbitrarily used intact or after mixing with appropriate fillers, excipients, binders, sweeteners, etc., and then formed into products with different shapes such as granules, spheres, plates, cubes, tablets, films, and sheets.

Since the isomaltose and high isomaltose content products of the present invention well harmonize with other materials having sour-, acid-, salty-, astringent-, delicious-, or bitter-tastes, and have a satisfactorily high acid- and heat-tolerance, they can be favorably used in food products to sweeten and/or improve the taste or the quality of food products; amino acids, peptides, soy sauces, powdered soy sauces, miso, "funmatsu-miso" (a powdered miso), "moromi" (a refined sake), "hishio" (a refined soy sauce) "furikake" (a seasoned fish meal), mayonnaises, dressings, vinegars, "sanbai-zu" (a sauce of sugar, soy sauce and vinegar), "funmatsu-sushi-su" (powdered vinegar for sushi), "chuka-no-moto" (an instant mix for Chinese dish), "tentsuyu" (a sauce for Japanese deep-fat fried food), "mentsuyu" (a sauce for Japanese vermicelli), sauce, catsups, "yakiniku-no-tare" (a sauce for Japanese grilled meat), curry roux, instant stew mixes, instant soup mixes, "dashi-no-moto" (an instant stock mix), nucleotide seasonings, mixed seasonings, "mirin" (a sweet sake), "shin-mirin" (a synthetic mirin), table sugars, and coffee sugars. Also, the isomaltose and high isomaltose content products of the present invention can be arbitrarily used in "wagashi" (Japanese cakes) such as "senbei" (a rice cracker), "arare" (a rice cake cube), "okoshi" (a millet-and-rice cake), "mochi" (a rice paste) and the like, "manju" (a bun with a bean-jam), "uiro" (a sweet rice jelly), "an" (a bean jam) and the like, "yokan" (a sweet jelly of beans), "mizu-yokan" (a soft adzuki-bean jelly), "kingyoku" (a kind of yokan), jellies, pao de Castella, and "amedama" (a Japanese toffee); Western confectioneries such as a bun, biscuit, cracker, cookie, pie, pudding, butter cream, custard cream, cream puff, waffle, sponge cake, doughnut, chocolate, chewing gum, caramel, nougat, and candy; frozen desserts such as an ice cream and sherbet; syrups such as "kajitsu-no-syrup-zuke" (a preserved fruit) and "korimitsu" (a sugar syrup for shaved ice) ; pastes such as a flour paste, peanut paste, fruit paste, and spread; processed fruits and vegetables such as a jam, marmalade, "syrup-zuke" (fruit pickles), and "toka" (conserves); pickles and pickled products such as a "fukujin-zuke" (red colored radish pickles), "bettara-zuke" (a kind of whole fresh radish pickles), "senmai-zuke" (a kind of sliced fresh radish pickles), and "rakkyo-zuke" (pickled shallots); premixes for pickles and pickled products such as a "takuan-zuke-no-moto" (a premix for pickled radish), and "hakusai-zuke-no-moto" (a premix for fresh white rape pickles); meat products such as a ham and sausage; products of fish meat such as a fish ham, fish sausage, "kamaboko" (a steamed fish paste), "chikuwa" (a kind of fish paste), and "tenpura" (a Japanese deep-fat fried fish paste); "chinmi" (relish) such as a "unino-shiokara" (salted guts of sea urchin), "ika-no-shiokara" (salted guts of squid), "su-konbu" (processed tangle), "saki-surume" (dried squid strips), "fugu-no-mirin-boshi" (a dried mirin-seasoned swellfish); "tsukudani" (foods boiled down in soy sauce) such as those of lavers, edible wild plants, dried squids, small fishes, and shellfishes; daily dishes such as a "nimame" (cooked beans), potato salad, and "konbu-maki" (a tangle roll); milk products such as yogurts and cheeses; canned and bottled products such as those of meat, fish meat, fruit, and vegetables; alcoholic beverages such as a sake, synthetic sake, liqueur, and foreign liquors and drinks; soft drinks such as a coffee, tea, cocoa, juice, carbonated beverage, sour milk beverage, and beverage containing lactic acid bacteria; instant food products such as an instant pudding mix, instant hot cake mix, "sokuseki-shiruko" (an instant mix of adzuki-bean soup with rice cake), and instant soup mix; and other foods and beverages such as a solid food for babies, food for therapy, health/tonic drink, peptide food, frozen food, and health food.

The isomaltose and high isomaltose content products of the present invention can be arbitrarily used to improve the taste preference of feeds and pet foods for animals and pets such as domestic animals, poultry, honey bees, silk worms, and fishes; and also they can be arbitrarily used as a sweetener, taste-improving agent, flavoring substance, quality-improving agent, and stabilizer in products in a liquid or solid form such as a tobacco, cigarettes, tooth paste, lipstick/rouge, lip creams, internal liquid medicine, tablet, troche, cod liver oil in the form of drops, cachou, oral refrigerants, and gargles.

Stable and high-quality health foods and pharmaceuticals in a liquid, paste or solid form can be obtained by incorporating, as a quality-improving agent and/or stabilizer, the isomaltose and high isomaltose content products of the present invention into health foods and pharmaceuticals which contain effective ingredients, active ingredients, or biologically active substances. Examples of such biologically active substances include lymphokines such as α-, 3- and γ-interferons, tumor necrosis factor-α (TNF-α), tumor necrosis factor-β (TNF-β), macrophage migration inhibitory factor, colony-stimulating factor, transfer factor, and interleukins; hormones such as insulin, growth hormone, prolactin, erythropoietin, and follicle-stimulating hormone; biological preparations such as BCG vaccine, Japanese encephalitis vaccine, measles vaccine, live polio vaccine, smallpox vaccine, tetanus toxoid, Trimeresurus antitoxin, and human immunoglobulin; antibiotics such as penicillin, erythromycin, chloramphenicol, tetracycline, streptomycin, and kanamycin sulfate; vitamins such as thiamine, riboflavin, L-ascorbic acid, α-glycosyl ascorbic acid, cod liver oil, carotenoid, ergosterol, tocopherol, rutin, α-glycosyl rutin, naringin, α-glycosyl naringin, hesperidin, and α-glycosyl hesperidin; enzymes such as lipase, elastase, urokinase, protease, β-amylase, isoamylase, glucanase, and lactase; extracts such as a ginseng extract, bamboo leaf extract, Japanese apricot extract, pine leaf extract, snapping turtle extract, chlorella extract, aloe extract, and propolis extract; live microorganisms such as viruses, lactic acid bacteria, and yeasts; and royal jelly.

The methods for incorporating the isomaltose or the high isomaltose content products of the present invention into the aforesaid compositions are those which can complete the incorporation before completion of the processing of the compositions, and can be appropriately selected from the following conventional methods of mixing, kneading, dissolving, melting, soaking, penetrating, dispersing, applying, coating, spraying, injecting, crystallizing, and solidifying. The isomaltose or the high isomaltose content product can be preferably incorporated into the compositions in an amount, usually, of at least 0.1%, preferably, at least 1%, and more preferably, 2-99.99% (w/w).

The following experiments explain the present invention in more detail:

EXPERIMENT 1

Preparation of α-isomaltosylglucosaccharide-forming Enzyme and α-isomaltosyl-Transferring Enzyme A liquid culture medium consisting of 4.0% (w/v) of "PINE-DEX #4", a partial starch hydrolysate commercialized by Matsutani Chemical Ind., Tokyo, Japan, 1.8% (w/v) of "ASAHIMEAST", a yeast extract commercialized by Asahi Breweries, Ltd., Tokyo, Japan, 0.1% (w/v) of dipotassium phosphate, 0.06% (w/v) of sodium phosphate dodecahydrate, 0.05% (w/v) magnesium sulfate heptahydrate, and water was placed in 500-ml Erlenmeyer flasks in a respective volume of 100 ml, sterilized by autoclaving at 121° C. for 20 min, cooled, and then seeded with *Bacillus globisporus* C9 strain, FERM BP-7143, followed by culturing under rotary-shaking conditions at 27° C. and 230 rpm for 48 hours for a seed culture.

About 20 L of a fresh preparation of the same liquid culture medium as used in the above seed culture were placed in a 30-L fermentor, sterilized by heating, and then cooled to 27° C. and inoculated with 1% (v/v) of the seed culture, followed by culturing at 27° C. and pH 6.0-8.0 for 48 hours under aeration-agitation conditions. After completion of the culture, the resulting culture, which had about 0.45 unit/ml of the α-isomaltosylglucosaccharide-forming enzyme, about 1.5 units/ml of α-isomaltosyl-transferring enzyme, and about 0.95 unit/ml of cyclotetrasaccharide-forming activity, was centrifuged at 10,000 rpm for 30 min to obtain about 18 L of a supernatant. When measured for enzymatic activity, the supernatant had about 0.45 unit/ml of the α-isomaltosylglucosaccharide-forming enzyme, i.e., a total enzymatic activity of about 8,110 units; about 1.5 units/ml of α-isomaltosyl-transferring enzyme, i.e., a total enzymatic activity of about 26,900 units. The supernatant thus obtained can be used as an enzyme preparation of α-isomaltosylglucosaccharide-forming enzyme and α-isomaltosyl-transferring enzyme.

The activities of these enzymes were assayed as follows: The α-isomaltosylglucosaccharide-forming enzyme of the present invention was assayed for enzymatic activity by dissolving maltotriose in 100 mM acetate buffer (pH 6.0) to give a concentration of 2% (w/v) for a substrate solution, adding a 0.5 ml of an enzyme solution to a 0.5 ml of the substrate solution, enzymatically reacting the mixture solution at 35° C. for 60 min, suspending the reaction mixture by heating at 100° C. for 10 min, and quantifying maltose, among the isomaltosyl maltose and maltose formed in the reaction mixture, by high-performance liquid chromatography (abbreviated as "HPLC" hereinafter). HPLC was carried out using "YMC PACK ODS-AQ303 column" commercialized by YMC Co., Ltd., Tokyo, Japan, at a column temperature of 40° C. and a flow rate of 0.5 ml/min of water; and using "RI-8012", a differential refractometer commercialized by Tosoh Corporation, Tokyo, Japan. One unit activity of the α-isomaltosylglucosaccharide-forming enzyme is defined as the enzyme amount that forms one micromole of maltose per minute under the above enzymatic reaction conditions.

The α-isomaltosyl-transferring enzyme was assayed for enzymatic activity by dissolving panose in 100 mM acetate buffer (pH 6.0) to give a concentration of 2% (w/v) for a substrate solution, adding a 0.5 ml of an enzyme solution to 0.5 ml of the substrate solution, enzymatically reacting the mixture solution at 35° C. for 30 min, suspending the reaction mixture by boiling for 10 min, and quantifying glucose, among the cyclotetrasaccharide and glucose formed in the reaction mixture, by the glucose oxidase method. One unit activity of the α-isomaltosyl-transferring enzyme is defined as the enzyme amount that forms one micromole of glucose per minute under the above enzymatic reaction conditions.

The cyclotetrasaccharide-forming activity is assayed by dissolving "PINE-DEX #100", a partial starch hydrolysate commercialized by Matsutani Chemical Ind., Tokyo, Japan, in 50 mM acetate buffer (pH 6.0) to give a concentration of 2% (w/v) for a substrate solution, adding 0.5 ml of an enzyme solution to 0.5 ml of the substrate solution, enzymatically reacting the mixture solution at 35° C. for 60 min, suspending the reaction mixture by boiling for 10 min, and then further adding to the resulting mixture one milliliter of 50 mM acetate buffer (pH 5.0) with 70 units/ml of "TRANSGLUCOSIDASE L AMANO™", an α-glucosidase commercialized by Amano Pharmaceutical Co., Ltd., Aichi, Japan, and 27 units/ml of glucoamylase, commercialized by Nagase Biochemicals, Ltd., Kyoto, Japan, and incubated at 50° C. for 60 min, inactivating the remaining enzymes by heating at 100° C. for 10 min, and quantifying cyclotetrasaccharide on HPLC similarly as above. One unit of cyclotetrasaccharide-forming activity is defined as the enzyme amount that forms one micromole of cyclotetrasaccharide per minute under the above enzymatic reaction conditions.

EXPERIMENT 2

Isolation of α-isomaltosylglucosaccharide-forming enzyme and α-isomaltosyl-transferring enzyme

EXPERIMENT 2-1

Isolation of α-isomaltosylglucosaccharide-forming enzyme

About 18 L of the supernatant in Experiment 1 was salted out with 80% saturated ammonium sulfate and allowed to stand at 4° C. for 24 hours, and the formed precipitates were collected by centrifugation at 10,000 rpm for 30 min, dissolved in 10 mM phosphate buffer (pH 7.5), and dialyzed against a fresh preparation of the same buffer to obtain about 400 ml of a crude enzyme solution with 8,110 units of α-isomaltosylglucosaccharide-forming enzyme, 24,700 units of α-isomaltosyl-transferring enzyme, and about 15,600 units of cyclotetrasaccharide-forming activity. The crude enzyme solution was subjected to ion-exchange chromatography using 1,000 ml of "SEPABEADS FP-DA13" gel, an ion-exchange resin commercialized by Mitsubishi Chemical Industries, Ltd., Tokyo, Japan. The α-isomaltosylglucosaccharide-forming enzyme and cyclotetrasaccharide were eluted as non-adsorbed fractions without adsorbing on the ion-exchange resin. The resulting enzyme solution was dialyzed against 10 mM phosphate buffer (pH 7.0) with 1 M ammonium sulfate, and the dialyzed solution was centrifuged to remove impurities, and subjected to affinity chromatography using 500 ml of "SEPHACRYL HR S-200", a gel commercialized by Amersham Corp., Div. Amersham International, Arlington Heights, Ill., USA. Enzymatically active components adsorbed on the gel and, when sequentially eluted with a linear gradient decreasing from 1 M to 0 M of ammonium sulfate and a linear gradient increasing from 0 mM to 100 mM of maltotetraose, the α-isomaltosylglucosaccharide-forming enzyme and the α-isomaltosyl-transferring enzyme were separately eluted, i.e., the former was eluted with the linear gradient of maltotetraose at about 30 mM and the latter was eluted with the linear gradient of ammonium sulfate at about 0 M. Thus, fractions with α-isomaltosyltransferring activity and those with the α-isomaltosylglucosaccharide-forming activity were separatory collected.

The above α-isomaltosylglucosaccharide-forming enzyme fraction were pooled and dialyzed against 10 mM phosphate buffer (pH 7.0) containing 1 M ammonium sulfate. The dialyzed solution was centrifuged to remove insoluble impurities, and the resulting supernatant was fed to hydrophobic chromatography using 350 ml of "BUTYL-TOYOPEARL 650 M", a gel commercialized by Tosoh Corporation, Tokyo, Japan. The active enzyme was adsorbed on the gel and then eluted therefrom at about 0.3 M ammonium sulfate using a linear gradient decreasing from 1 M to 0 M of ammonium sulfate, followed by collecting fractions with the enzyme activity. The fractions were pooled and then dialyzed against 10 mM phosphate buffer (pH 7.0) containing 1 M ammonium sulfate. The resulting dialyzed solution was centrifuged to remove impurities and fed to affinity chromatography using "SEPHACRYL HR S-200" gel to purify the enzyme. The amount of enzyme activity, specific activity, and yield of the α-isomaltosylglucosaccharide-forming enzyme in each purification step are in Table 1.

TABLE 1

| Purification step | Enzyme* activity (unit) | Specific activity of enzyme* (unit/mg protein) | Yield (%) |
| --- | --- | --- | --- |
| Culture supernatant | 8,110 | 0.12 | 100 |
| Dialyzed solution after salting out with ammonium sulfate | 7,450 | 0.56 | 91.9 |
| Eluate from ion-exchange column chromatography | 5,850 | 1.03 | 72.1 |
| Eluate from affinity column chromatography | 4,040 | 8.72 | 49.8 |
| Eluate from hydrophobic column chromatography | 3,070 | 10.6 | 37.8 |
| Eluate from affinity column chromatography | 1,870 | 13.6 | 23.1 |

Note:
The symbol "*" means the α-isomaltosylglucosaccharide-forming enzyme.

The finally purified α-isomaltosylglucosaccharide-forming enzyme specimen was assayed for purity on gel electrophoresis using a 7.5% (w/v) polyacrylamide gel and detected on the gel as a single protein band, i.e., a high purity enzyme specimen.

EXPERIMENT 2-2

Property of α-isomaltosylglucosaccharide-forming Enzyme

A purified specimen of α-isomaltosylglucosaccharide-forming enzyme, obtained by the method in Experiment 2-1, was subjected to SDS-PAGE using a 7.5% (w/v) of polyacrylamide gel and then determined for molecular weight by comparing with the dynamics of standard molecular markers electrophoresed in parallel, commercialized by Bio-Rad Laboratories Inc., Brussels, Belgium, revealing that the enzyme had a molecular weight of about 140,000±20,000 daltons.

A fresh preparation of the above purified specimen was subjected to isoelectrophoresis using a gel containing 2% (w/v) ampholine commercialized by Amersham Corp., Div. Amersham International, Arlington Heights, Ill., USA, and then measured for pHs of protein bands and gels to determine the isoelectric point of the enzyme, revealing that the enzyme had an isoelectric point of about 5.2±0.5.

Figure 2:
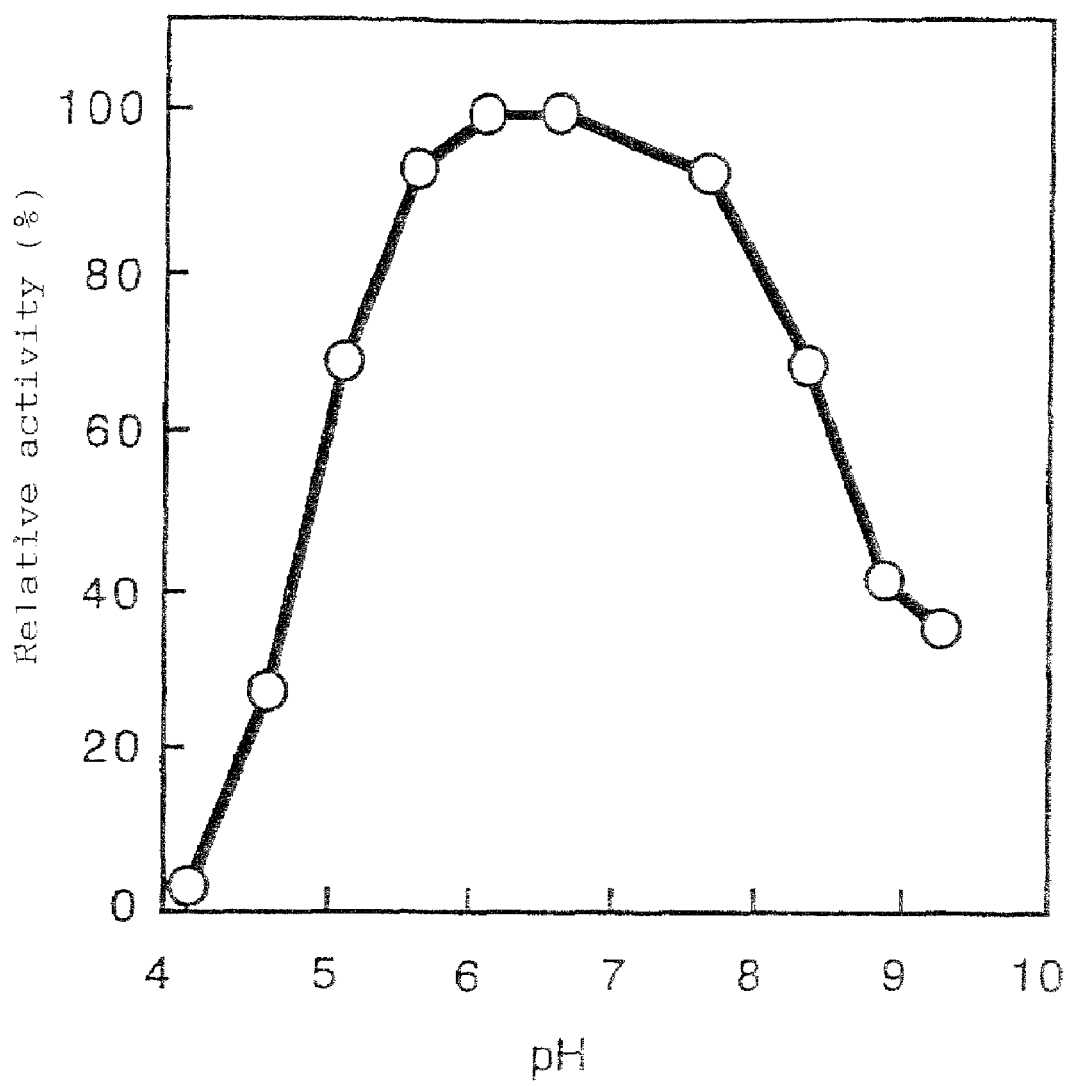
FIG. 2 shows the pH influence on the enzymatic activity of α-isomaltosylglucosaccharide-forming enzyme from a microorganism of *Bacillus globiformis* C9 strain.
Figure 3:
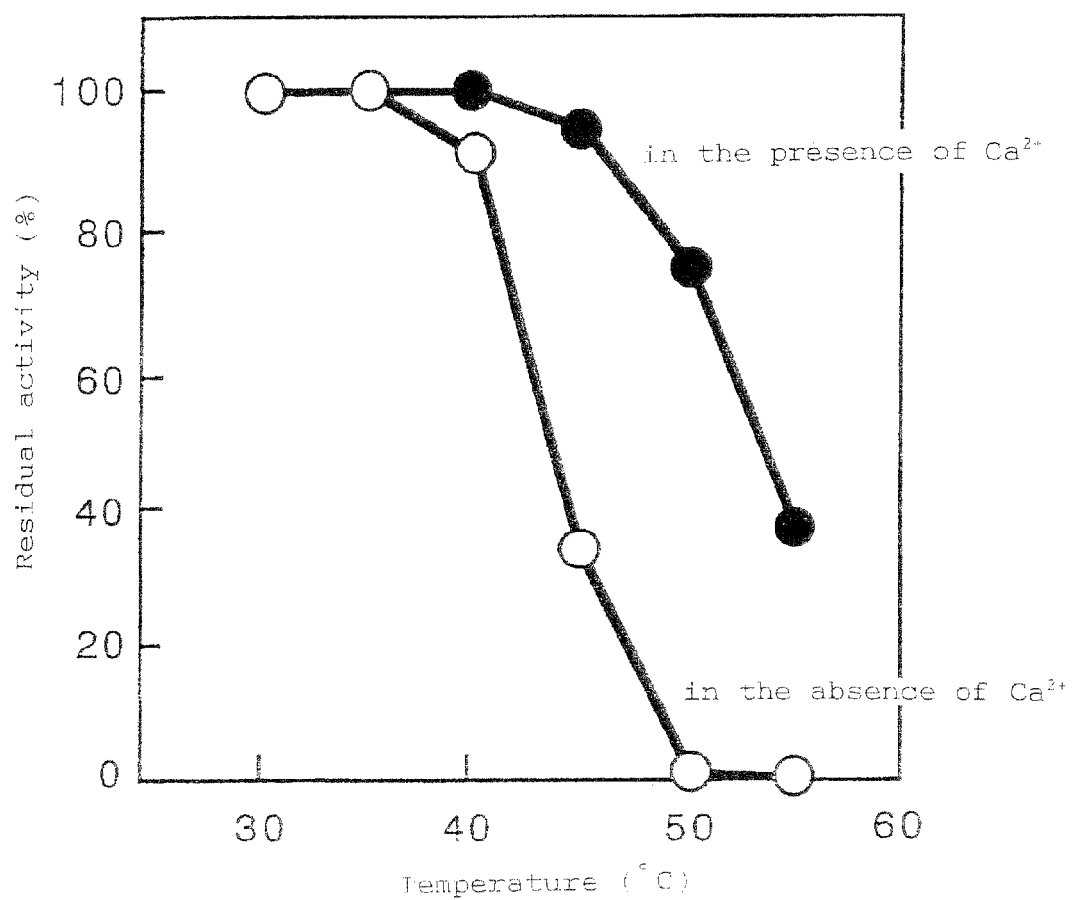
FIG. 3 shows the thermal stability of α-isomaltosylglucosaccharide-forming enzyme from a microorganism of *Bacillus globiformis* C9 strain.
Figure 4:
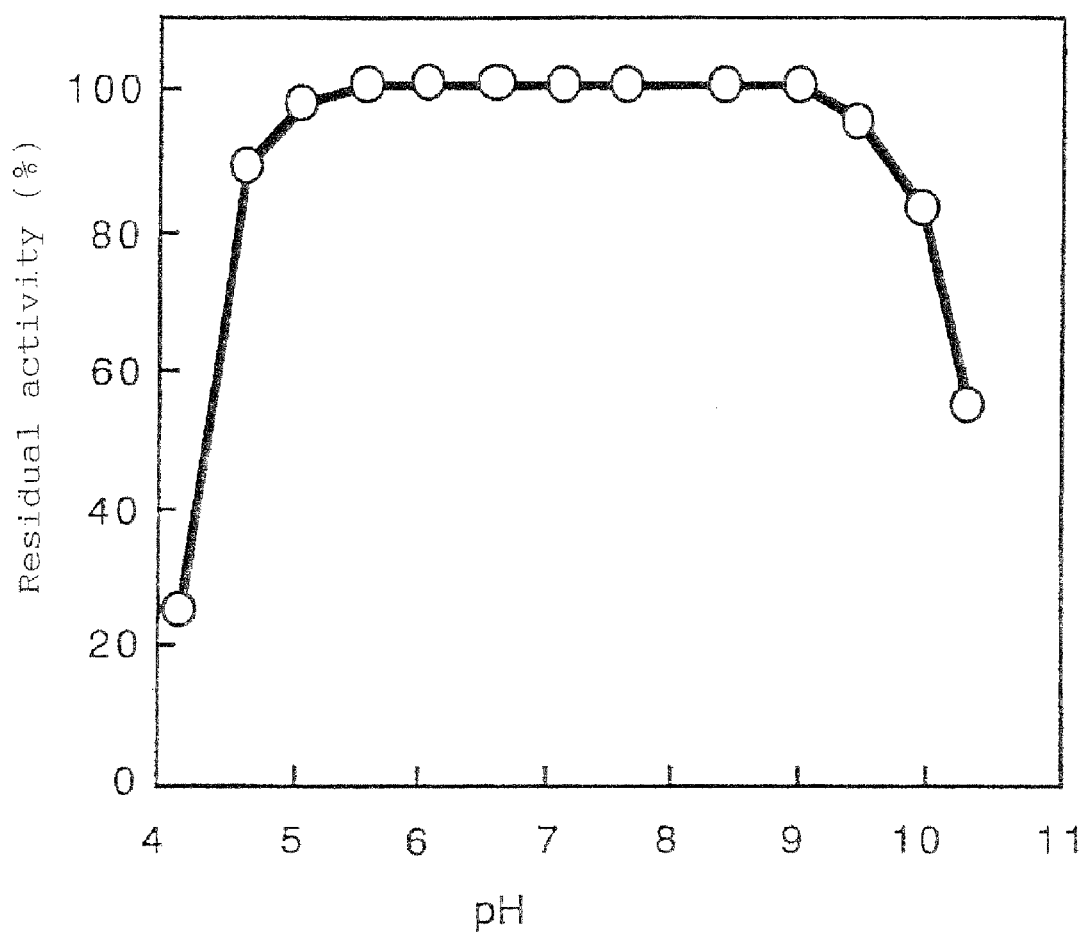
FIG. 4 shows the pH stability of α-isomaltosylglucosaccharide-forming enzyme from a microorganism of *Bacillus globiformis* C9 strain.

The influence of temperature and pH on the activity of α-isomaltosylglucosaccharide-forming enzyme was examined in accordance with the assay for the enzyme activity, where the influence of temperature was conducted in the presence or the absence of 1 mM $Ca^{2+}$. These results are in FIG. 1 (influence of temperature) and FIG. 2 (influence of pH). The optimum temperature of the enzyme was about 40° C. (in the absence of $Ca^{2+}$) and about 45° C. (in the presence of 1 mM $Ca^{2+}$) when incubated at pH 6.0 for 60 min, and the optimum pH of the enzyme was about 6.0 to about 6.5 when incubated at 35° C. for 60 min. The thermal stability of the enzyme was determined by incubating the testing enzyme solutions in 20 mM acetate buffer (pH 6.0) at prescribed temperatures for 60 min in the presence or the absence of 1 mM $Ca^{2+}$, cooling the resulting enzyme solutions with water, and assaying the remaining enzyme activity of each solution. The pH stability of the enzymes was determined by keeping the testing enzyme solutions in 50 mM buffers having prescribed pHs at 4° C. for 24 hours, adjusting the pH of each solution to 6.0, and assaying the remaining enzyme activity of each solution. These results are respectively in FIG. 3 (thermal stability) and FIG. 4 (pH stability). As a result, the enzyme had thermal stability of up to about 35° C. in the absence of $Ca^{2+}$ and about 40° C. in the presence of 1 mM $Ca^{2+}$, and pH stability of about 4.5 to about 9.0.

The influence of metal ions on the activity of α-isomaltosylglucosaccharide-forming enzyme was examined in the presence of 1 mM of each metal-ion according to the assay for the enzyme activity. The results are in Table 2.

TABLE 2

| Metal ion | Relative activity (%) | Metal ion | Relative activity (%) |
| --- | --- | --- | --- |
| None | 100 | $Hg^{2+}$ | 4 |
| $Zn^{2+}$ | 92 | $Ba^{2+}$ | 65 |
| $Mg^{2+}$ | 100 | $Sr^{2+}$ | 80 |
| $Ca^{2+}$ | 115 | $Pb^{2+}$ | 103 |
| $Co^{2+}$ | 100 | $Fe^{2+}$ | 98 |
| $Cu^{2+}$ | 15 | $Fe^{3+}$ | 97 |
| $Ni^{2+}$ | 98 | $Mn^{2+}$ | 111 |
| $Al^{3+}$ | 99 | EDTA | 20 |

As is evident from the results in Table 2, the enzyme activity was greatly inhibited by $Hg^{2+}$, $Cu^{2+}$, and EDTA, and also inhibited by $Ba^{2+}$ and $Sr^{2+}$. It was also found that the enzyme was activated by $Ca^{2+}$ and $Mn^{2+}$.

EXPERIMENT 2-3

Property of α-isomaltosyl-transferring Enzyme

A fraction with α-isomaltosyl-transferring enzyme, obtained in Experiment 2-1, was dialyzed against 10 mM phosphate buffer (pH 7.0) containing 1 M ammonium sulfate. The resulting dialyzed solution was centrifuged to remove impurities and subjected to hydrophobic chromatography using 350 ml of "BUTYL-TOYOPEARL 650 M", a gel commercialized by Tosoh Corporation, Tokyo, Japan. The enzyme adsorbed on the gel and then eluted with a linear gradient decreasing from 1 M to 0 M ammonium sulfate, resulting in an elution of the enzyme from the gel at a concentration of about 0.3 M ammonium sulfate and collecting fractions with the enzyme activity. Thereafter, the fractions were pooled and dialyzed against 10 mM phosphate buffer (pH 7.0) containing 1 M ammonium sulfate, and the dialyzed solution was centrifuged to remove impurities and purified on affinity chromatography using "SEPHACRYL HR S-200" gel. The amount of enzyme activity, specific activity, and yield of the α-isomaltosyl-transferring enzyme in each purification step are in Table 3.

TABLE 3

| Purification step | Enzyme* activity (unit) | Specific activity of enzyme* (unit/mg protein) | Yield (%) |
|---|---|---|---|
| Culture supernatant | 26,900 | 0.41 | 100 |
| Dialyzed solution after salting out with ammonium sulfate | 24,700 | 1.85 | 91.8 |
| Eluate from ion-exchange column chromatography | 19,400 | 3.41 | 72.1 |
| Eluate from affinity column chromatography | 13,400 | 18.6 | 49.8 |
| Eluate from hydrophobic column chromatography | 10,000 | 21.3 | 37.2 |
| Eluate from affinity column chromatography | 6,460 | 26.9 | 24.0 |

Note:
The symbol "*" means the α-isomaltosyl-transferring enzyme.

EXPERIMENT 2-4

Property of α-isomaltosyl-transferring Enzyme

The purified specimen of α-isomaltosyl-transferring enzyme in Experiment 2-3 was subjected to SDS-PAGE using a 7.5% (w/v) of polyacrylamide gel and then determined for molecular weight by comparing with the dynamics of standard molecular markers electrophoresed in parallel, commercialized by Bio-Rad Laboratories Inc., Brussels, Belgium, revealing that the enzyme had a molecular weight of about 112,000±20,000 daltons.

A fresh preparation of the above purified specimen was subjected to isoelectrophoresis using a gel containing 2% (w/v) ampholine commercialized by Amersham Corp., Div., Amersham International, Arlington Heights, Ill., USA, and then measured for pHs of protein bands and gel to determine the isoelectric point of the enzyme, revealing that the enzyme had an isoelectric point of about 5.5±0.5.

Figure 5:
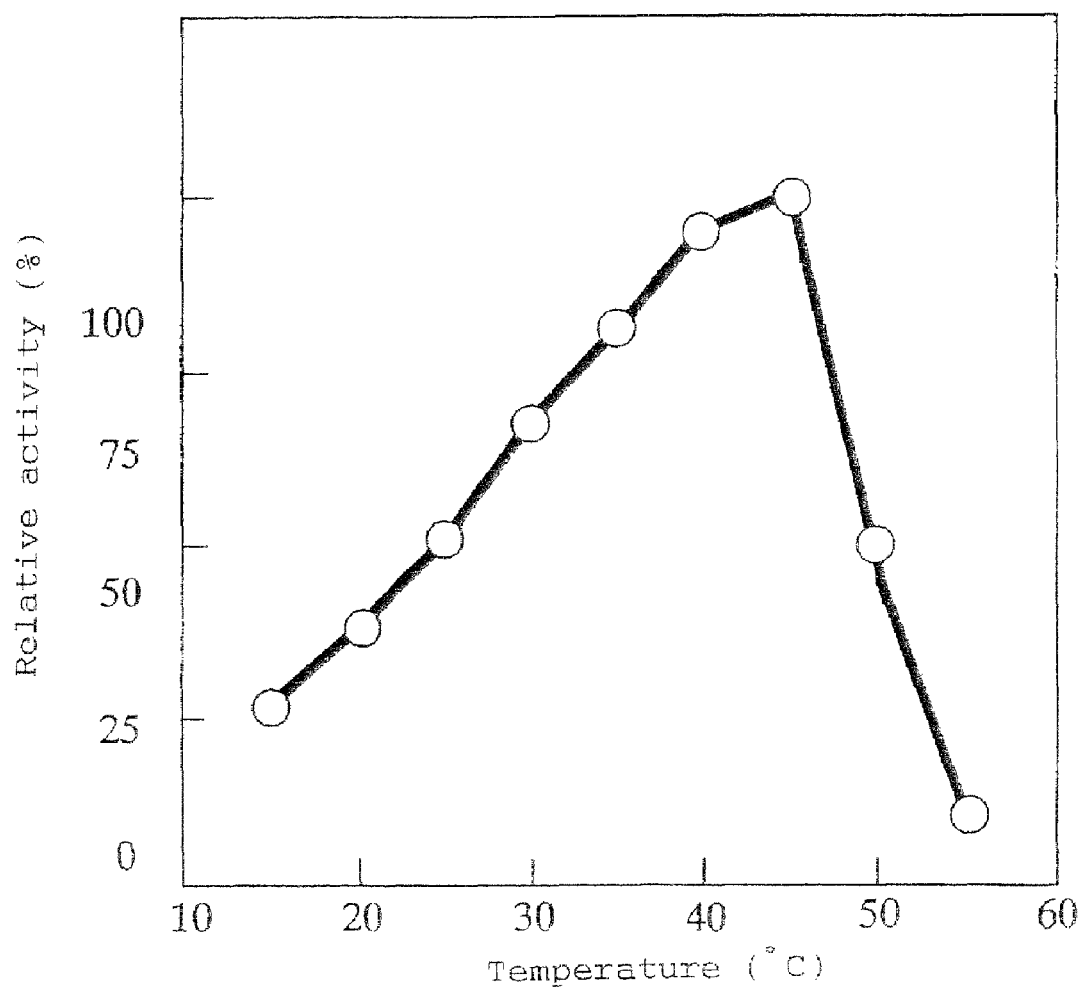
FIG. 5 shows the thermal influence on the enzymatic activity of α-isomaltosyl-transferring enzyme from a microorganism of *Bacillus globiformis* C9 strain.
Figure 6:
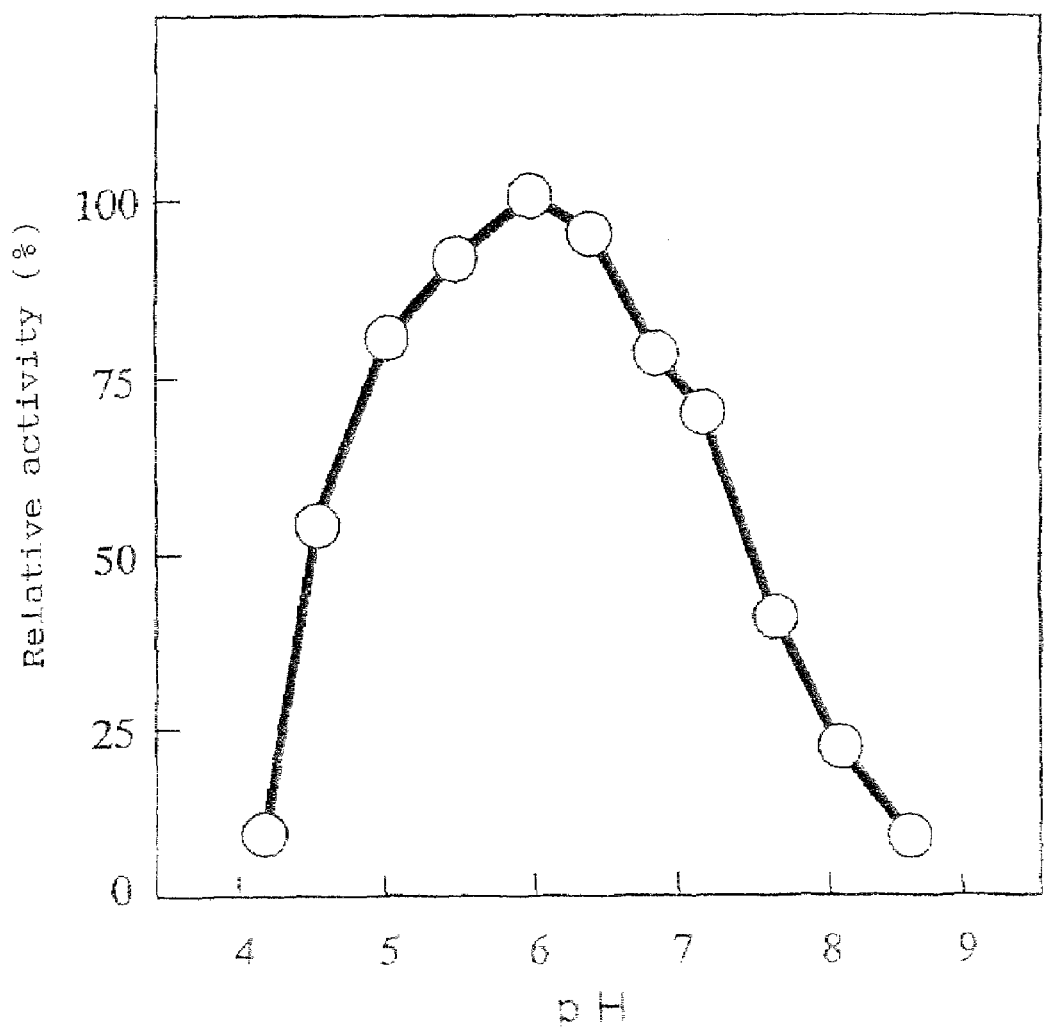
FIG. 6 shows the pH influence on the enzymatic activity of α-isomaltosyl-transferring enzyme from a microorganism of *Bacillus globiformis* C9 strain.
Figure 7:
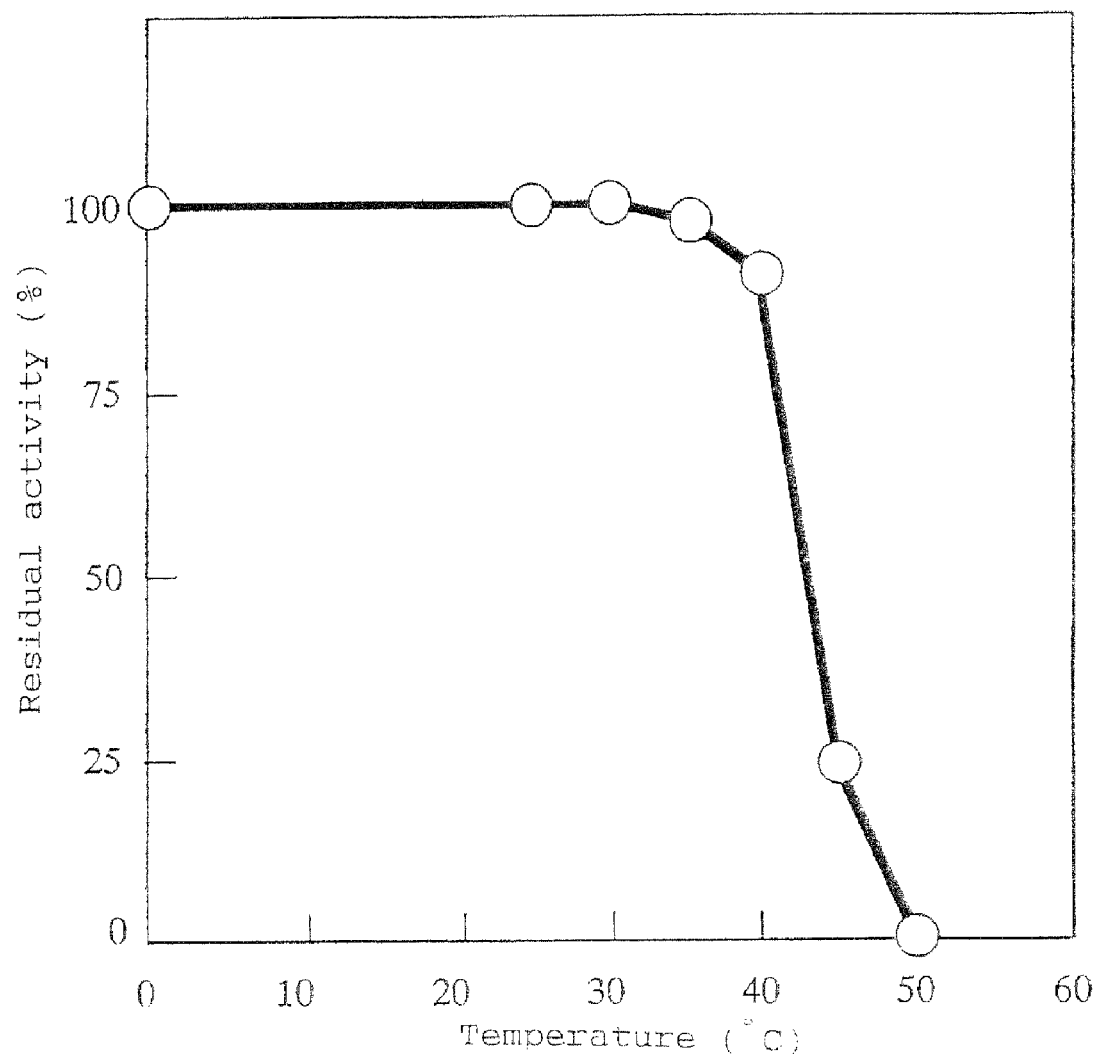
FIG. 7 shows the thermal stability of α-isomaltosyl-transferring enzyme from a microorganism of *Bacillus globiformis* C9 strain.
Figure 8:
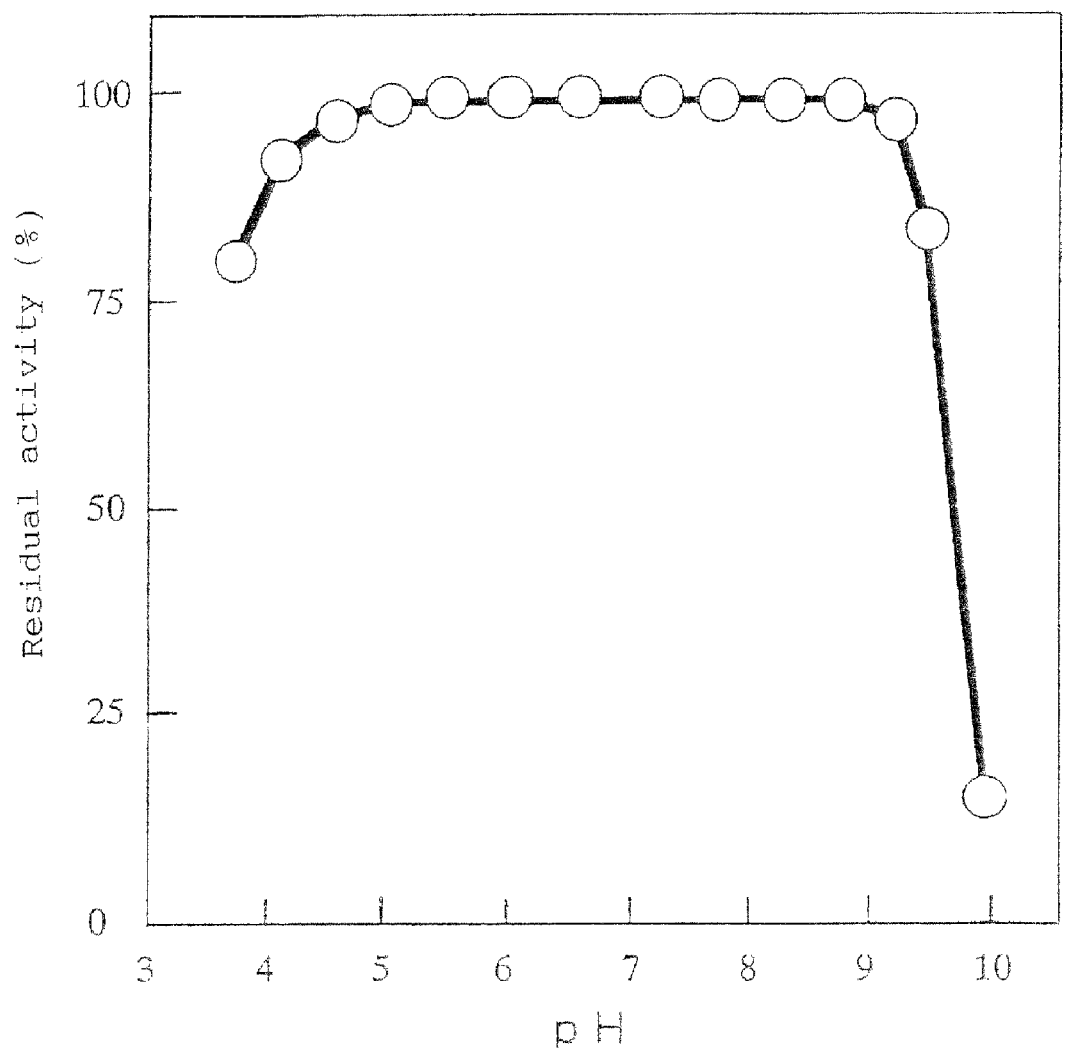
FIG. 8 shows the pH stability of α-isomaltosyl-transferring enzyme from a microorganism of *Bacillus globiformis* C9 strain.

The influence of temperature and pH on the activity of α-isomaltosyl-transferring enzyme was examined in accordance with the assay for the enzyme activity. These results are in FIG. 5 (influence of temperature) and FIG. 6 (influence of pH). The optimum temperature of the enzyme was about 45° C. when incubated at pH 6.0 for 30 min, and the optimum pH of the enzyme was about 6.0 when incubated at 35° C. for 30 min. The thermal stability of the enzyme was determined by incubating the testing enzyme solutions in 20 mM acetate buffer (pH 6.0) at prescribed temperatures for 60 min, cooling the resulting enzyme solutions with water, and assaying the remaining enzyme activity of each solution. The pH stability of the enzyme was determined by keeping the testing enzyme solutions in 50 mM buffers having prescribed pHs at 4° C. for 24 hours, adjusting the pH of each solution to 6.0, and assaying the remaining enzyme activity of each solution. These results are respectively in FIG. 7 (thermal stability) and FIG. 8 (pH stability). As a result, the enzyme had thermal stability of up to about 40° C. and pH stability of about 4.0 to about 9.0.

The influence of metal ions on the activity of α-isomaltosyl-transferring enzyme was examined in the presence of 1 mM of each metal-ion according to the assay for the enzyme activity. The results are in Table 4.

TABLE 4

| Metal ion | Relative activity (%) | Metal ion | Relative activity (%) |
|---|---|---|---|
| None | 100 | $Hg^{2+}$ | 1 |
| $Zn^{2+}$ | 88 | $Ba^{2+}$ | 102 |
| $Mg^{2+}$ | 98 | $Sr^{2+}$ | 101 |
| $Ca^{2+}$ | 101 | $Pb^{2+}$ | 89 |
| $Co^{2+}$ | 103 | $Fe^{2+}$ | 96 |
| $Cu^{2+}$ | 57 | $Fe^{3+}$ | 105 |
| $Ni^{2+}$ | 102 | $Mn^{2+}$ | 106 |
| $Al^{3+}$ | 103 | EDTA | 104 |

As evident form the results in Table 4, the enzyme activity was greatly inhibited by $Hg^{2+}$ and also inhibited by $Cu^{2+}$. It was also found that the enzyme was not activated by $Ca^{2+}$ and not inhibited by EDTA.

Both the α-isomaltosylglucosaccharide-forming enzyme and -he α-isomaltosyl-transferring enzyme from Bacillus globisporus C9 strain, FERM BP-7143, can be suitably used in the present invention.

EXPERIMENT 3

Production of α-isomaltosylglucosaccharide-forming Enzyme and α-isomaltosyl-transferring Enzyme A liquid nutrient culture medium, consisting of 4.0% (w/v) of "PINE-DEX #4", a partial starch hydrolysate, 1.8% (w/v) of "ASAHIMEAST", a yeast extract, 0.1% (w/v) of dipotassium phosphate, 0.06% (w/v) of sodium phosphate dodecahydrate, 0.05% (w/v) magnesium sulfate heptahydrate, and water was placed in 500-ml Erlenmeyer flasks in a respective volume of 100 ml each, autoclaved at 121° C. for 20 minutes to effect sterilization, cooled, inoculated with a stock culture of Bacillus globisporus C11, FERM BP-7144, and incubated at 27° C. for 48 hours under rotary shaking conditions of 230 rpm. The resulting cultures were pooled and used as a seed culture.

About 20 L of a fresh preparation of the same nutrient culture medium as used in the above culture were placed in a 30-L fermentor, sterilized by heating, cooled to 27° C., inoculated with 1% (v/v) of the seed culture, and incubated for about 48 hours while stirring under aeration agitation conditions at 27° C. and pH 6.0-8.0. The resultant culture, having about 0.55 unit/ml of α-isomaltosylglucosaccharide-forming enzyme activity, about 1.8 units/ml of α-isomaltosyl-transferring enzyme activity, and about 1.1 units/ml of cyclotetrasaccharide-forming enzyme activity, was centrifuged at 10,000 rpm for 30 min to obtain about 18 L of a supernatant. Measurement of the supernatant revealed that it had about 0.51 unit/ml of α-isomaltosylglucosaccharide-forming enzyme activity, i.e., a total enzyme activity of about 9,180 units; and about 1.7 units/ml of α-isomaltosyl-transferring enzyme activity, i.e., a total enzyme activity of about 30,400 units.

An 18 L of the above supernatant was salted out with an 80% saturated ammonium sulfate solution and allowed to stand at 4° C. for 24 hours. Then the salted out precipitates were collected by centrifugation at 10,000 for 30 min, dissolved in 10 mM phosphate buffer (pH 7.5), dialyzed against a fresh preparation of the same buffer to obtain about 416 ml of a crude enzyme solution. The crude enzyme solution was revealed to have 8,440 units of the α-isomaltosylglucosaccharide-forming enzyme, about 28,000 units or α-isomaltosyl-transferring enzyme, and about 17,700 units of cyclotetrasaccharide-forming enzyme. When subjected to ion-exchange chromatography using "SEPABEADS FP-DA13" gel, disclosed in Experiment 2-1, the above three types of enzymes were eluted as non-adsorbed fractions without adsorbing on the gel. The non-adsorbed fractions with those enzymes were pooled and dialyzed against 10 mM phosphate buffer (pH 7.0) containing 1 M ammonium sulfate, and the dialyzed solution was centrifuged to remove impurities. The resulting supernatant was fed to affinity chromatography using 500 ml of "SEPHACRYL HR S-200" gel to purify the enzyme. Active enzymes were adsorbed on the gel and were sequentially eluted with a linear gradient decreasing from 1 M to 0 M of ammonium sulfate and a linear gradient increasing from 0 mM to 100 mM of maltotetraose, followed by separate elutions of α-isomaltosyl-transferring enzyme and α-isomaltosylglucosaccharide-forming enzyme, where the former enzyme was eluted with the linear gradient of ammonium sulfate at a concentration of about 0.3 M and the latter enzyme was eluted with a linear gradient of maltotetraose at a concentration of about 30 mM. Therefore, fractions with the α-isomaltosylglucosaccharide-forming enzyme and those with α-isomaltosyl-transferring enzyme were separately collected and recovered.

EXPERIMENT 4

Isolation of α-isomaltosylglucosaccharide-forming Enzyme and α-isomaltosyl-transferring Enzyme The pooled fraction of α-isomaltosylglucosaccharide-forming enzyme in Experiment 3 was dialyzed against 10 mM phosphate buffer (pH 7.0) containing 1 M ammonium sulfate. The dialyzed solution was centrifuged to remove insoluble impurities, and the resulting supernatant was fed to hydrophobic chromatography using 350 ml of "BUTYL-TOYOPEARL 650 M", a gel commercialized by Tosoh Corporation, Tokyo, Japan. The enzyme adsorbed on the gel was eluted therefrom at about 0.3 M ammonium sulfate using a linear gradient decreasing from 1 M to 0 M of ammonium sulfate, followed by collecting fractions with the enzyme activity. The fractions were pooled and dialyzed against 10 mM phosphate buffer (pH 7.0) containing 1 M ammonium sulfate. The resulting dialyzed solution was centrifuged to remove impurities and fed to affinity chromatography using "SEPHACRYL HR S-200" gel to purify the enzyme. The amount of enzyme activity, specific activity, and yield of the α-isomaltosylglucosaccharide-forming enzyme in each purification step are in Table 5.

TABLE 5

| Purification step | Enzyme* activity (unit) | Specific activity of enzyme* (unit/mg protein) | Yield (%) |
|---|---|---|---|
| Culture supernatant | 9,180 | 0.14 | 100 |
| Dialyzed solution after salting out with ammonium sulfate | 8,440 | 0.60 | 91.9 |
| Eluate from ion-exchange column chromatography | 6,620 | 1.08 | 72.1 |
| Eluate from affinity column chromatography | 4,130 | 8.83 | 45.0 |
| Eluate from hydrophobic column chromatography | 3,310 | 11.0 | 36.1 |
| Eluate from affinity column chromatography | 2,000 | 13.4 | 21.8 |

Note:
The symbol "*" means the α-isomaltosylglucosaccharide-forming enzyme.

The finally purified α-isomaltosylglucosaccharide-forming enzyme specimen was assayed for purity on gel electrophoresis using a 7.5% (w/v) polyacrylamide gel and detected on the gel as a single protein band, meaning a high purity enzyme specimen.

EXPERIMENT 4-2

Property of α-isomaltosylglucosaccharide-forming Enzyme

The purified specimen of α-isomaltosylglucosaccharide-forming enzyme in Experiment 4-1 was subjected to SDS-PAGE using a 7.5% (w/v) of polyacrylamide gel and then determined for molecular weight by comparing with the dynamics of standard molecular markers electrophoresed in parallel, commercialized by Bio-Rad Laboratories Inc., Brussels, Belgium, revealing that the enzyme had a molecular weight of about 137,000±20,000 daltons.

A fresh preparation of the above purified specimen was subjected to isoelectrophoresis using a gel containing 2% (w/v) ampholine commercialized by Amersham Corp., Div., Amersham International, Arlington Heights, Ill., USA, and then measured for pHs of protein bands and gel to determine the isoelectric point of the enzyme, revealing that the enzyme had an isoelectric point of about 5.2±0.5.

Figure 9:
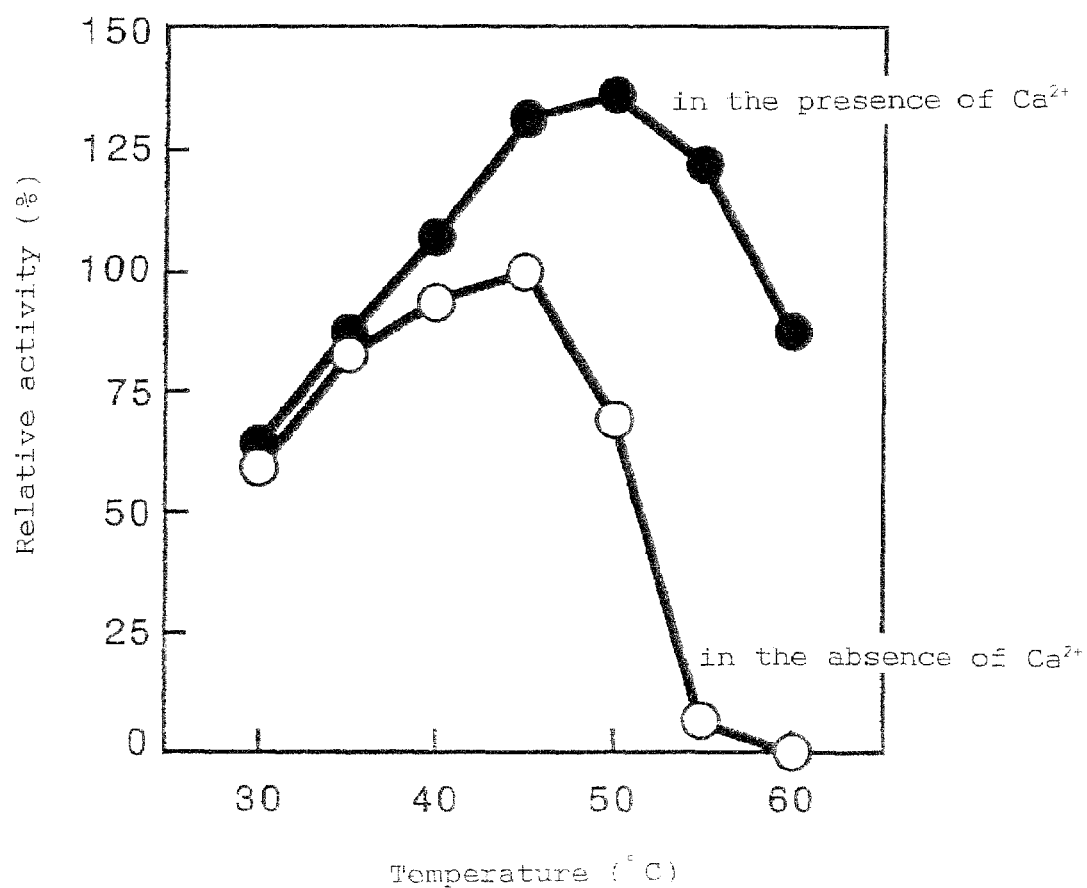
FIG. 9 shows the thermal influence on the enzymatic activity of α-isomaltosylglucosaccharide-forming enzyme from a microorganism of *Bacillus globisporus* C11 strain.
Figure 10:
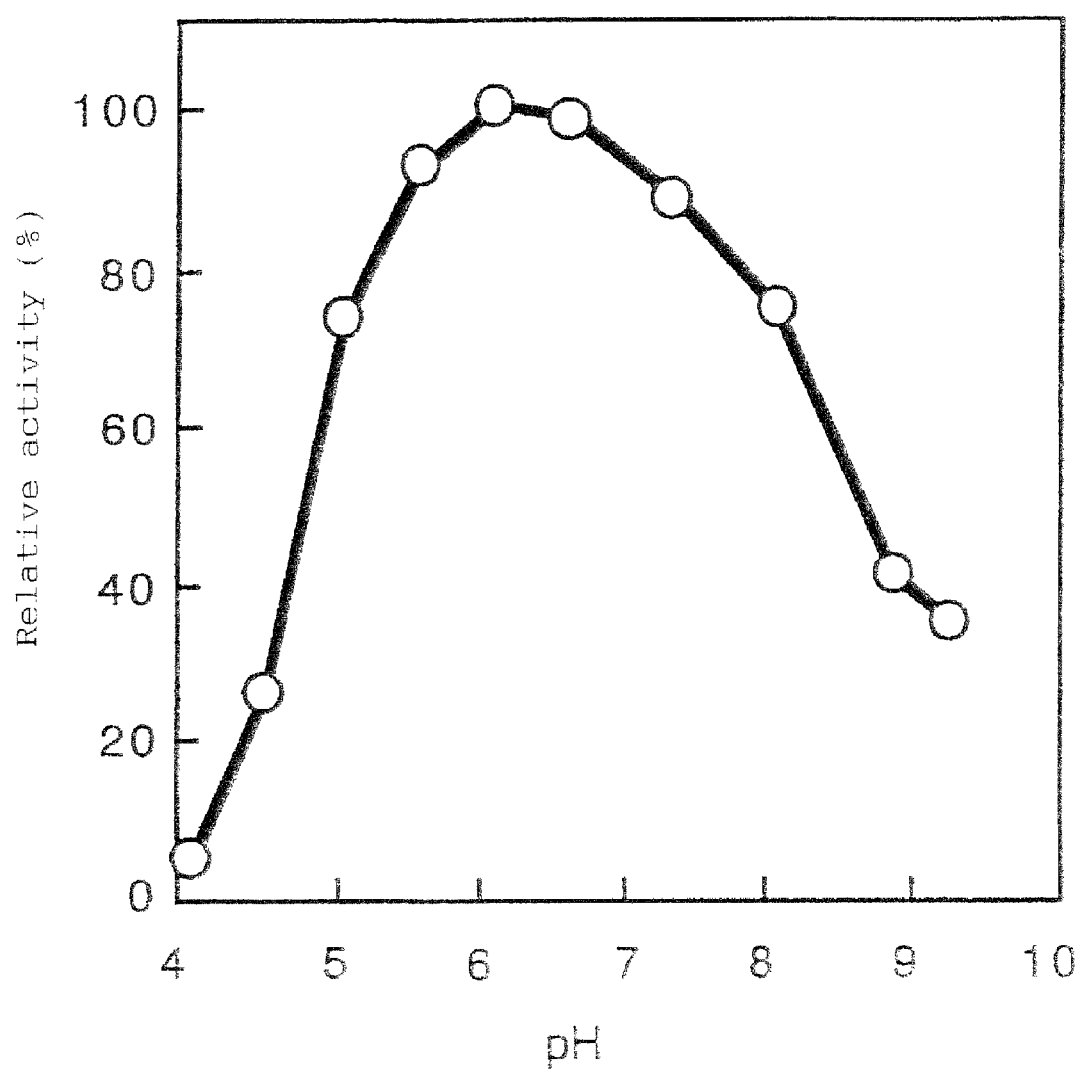
FIG. 10 shows the pH influence on α-isomaltosylglucosaccharide-forming enzyme from a microorganism of *Bacillus globisporus* C11 strain.
Figure 11:
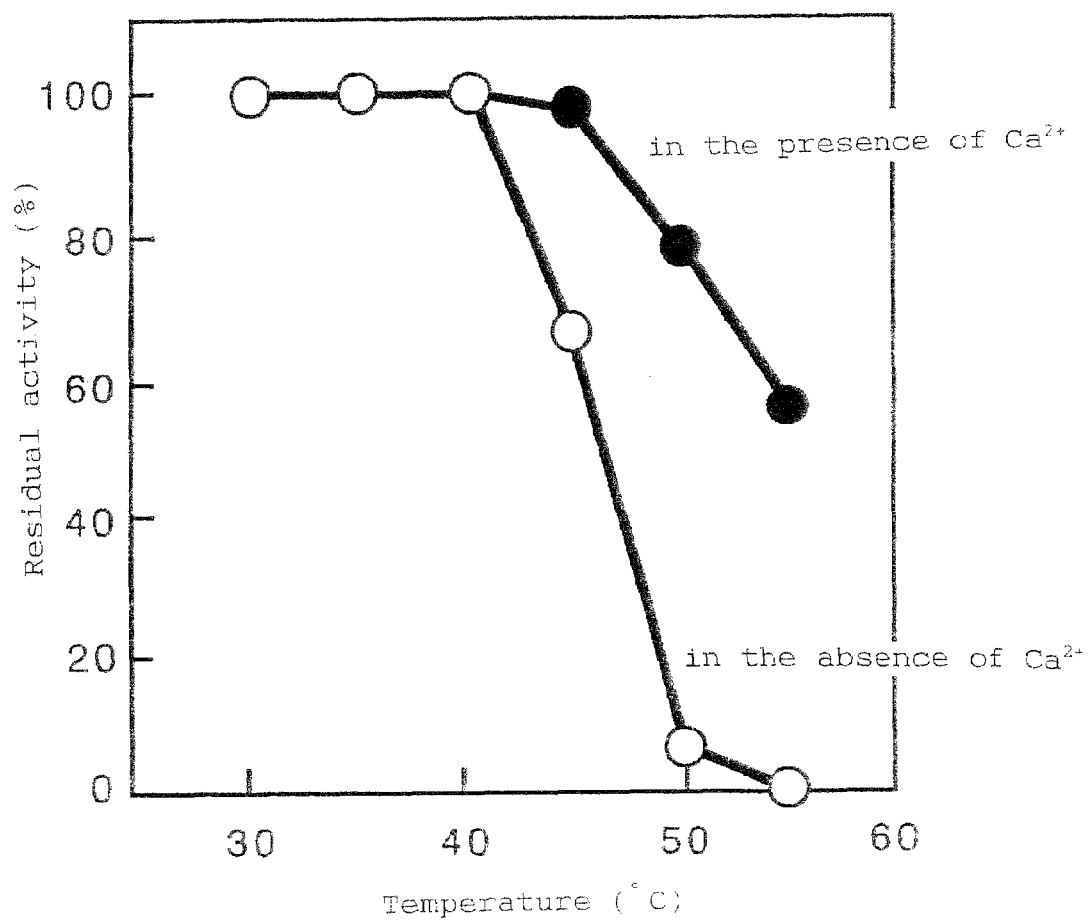
FIG. 11 shows the thermal stability of α-isomaltosylglucosaccharide-forming enzyme from a microorganism of *Bacillus globisporus* C11 strain.
Figure 12:
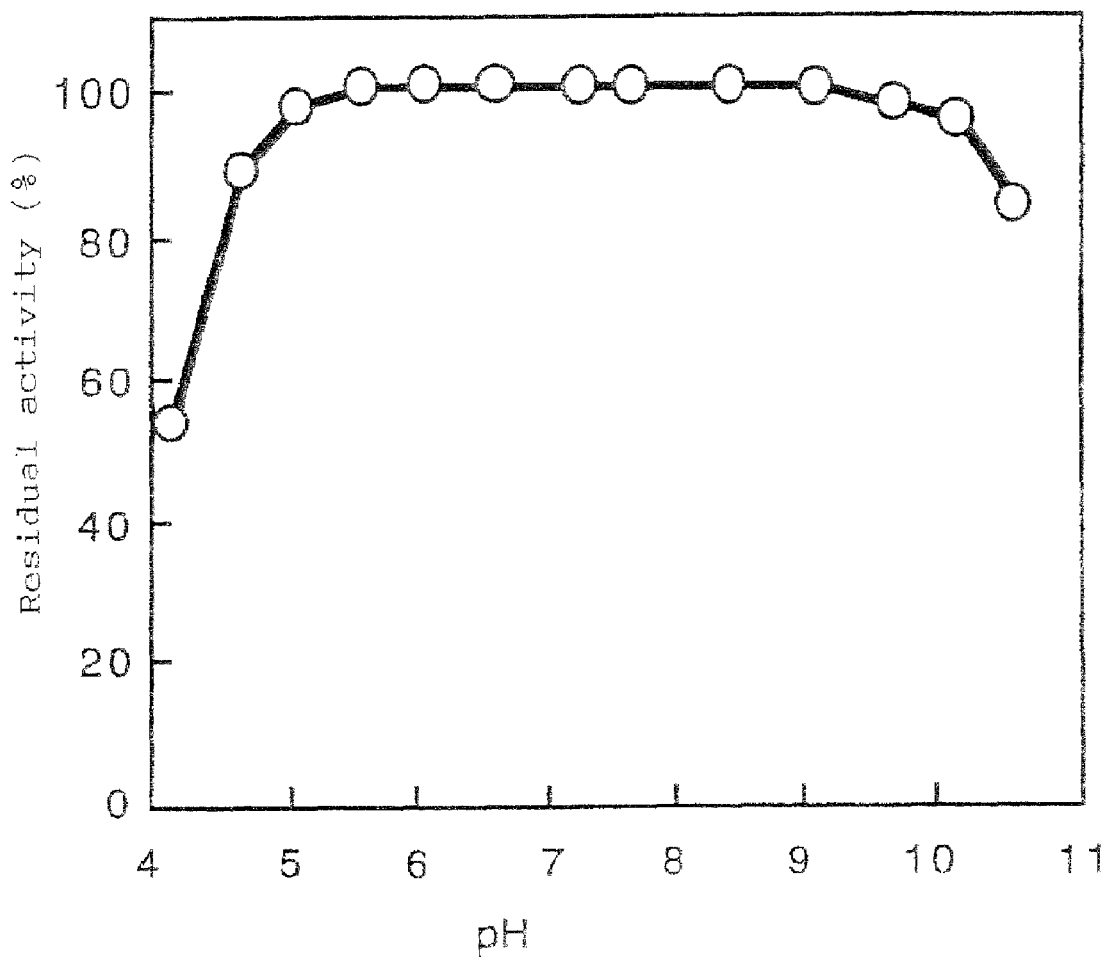
FIG. 12 shows the pH stability of α-isomaltosylglucosaccharide-forming enzyme from a microorganism of *Bacillus globisporus* C11 strain.

The influence of temperature and pH on the activity of α-isomaltosylglucosaccharide-forming enzyme was examined in accordance with the assay for the enzyme activity, where the influence of temperature was conducted in the presence or the absence of 1 mM $Ca^{2+}$. These results are in FIG. 9 (influence of temperature) and FIG. 10 (influence of pH). The optimum temperature of the enzyme was about 45° C. in the absence of $Ca^{2+}$ and about 50° C. in the presence of 1 mM $Ca^{2+}$ when incubated at pH 6.0 for 60 min. The optimum pH of the enzyme was about 6.0 when incubated at 35° C. for 60 min. The thermal stability of the enzyme was determined by incubating the testing enzyme solutions in 20 mM acetate buffer (pH 6.0) in the presence or the absence of 1 mM $Ca^{2+}$ at prescribed temperatures for 60 min, cooling the resulting enzyme solutions with water, and assaying the remaining enzyme activity of each solution. The pH stability of the enzyme was determined by keeping the testing enzyme solutions in 50 mM buffers having prescribed pHs at 4° C. for 24 hours, adjusting the pH of each solution to 6.0, and assaying the remaining enzyme activity of each solution. These results are respectively in FIG. 11 (thermal stability) and FIG. 12 (pH stability). As a result, the enzyme had thermal stability of up to about 40° C. in the absence of $Ca^{2+}$ and up to about 45° C. in the presence of 1 mM $Ca^{2+}$. The pH stability of enzyme was about 5.0 to about 10.0.

The influence of metal ions on the activity of α-isomaltosyl-transferring enzyme was examined in the presence of 1 mM of each metal-ion according to the assay for the enzyme activity. The results are in Table 6.

TABLE 6

| Metal ion | Relative activity (%) | Metal ion | Relative activity (%) |
|---|---|---|---|
| None | 100 | $Hg^{2+}$ | 4 |
| $Zn^{2+}$ | 91 | $Ba^{2+}$ | 65 |
| $Mg^{2+}$ | 98 | $Sr^{2+}$ | 83 |
| $Ca^{2+}$ | 109 | $Pb^{2+}$ | 101 |
| $Co^{2+}$ | 96 | $Fe^{2+}$ | 100 |
| $Cu^{2+}$ | 23 | $Fe^{3+}$ | 102 |
| $Ni^{2+}$ | 93 | $Mn^{2+}$ | 142 |
| $Al^{3+}$ | 100 | EDTA | 24 |

As evident from the results in Table 6, the enzyme activity was greatly inhibited by $Hg^{2+}$, $Cu^{2+}$, and EDTA and also inhibited by $Ba^{2+}$ and $Sr^{2+}$. It was also found that the enzyme was activated by $Ca^{2+}$ and $Mn^{2+}$.

EXPERIMENT 4-3

Amino Acid Sequence of α-isomaltosylglucosaccharide-forming Enzyme

The specification does not describe in detail the method for analyzing the amino acid sequence of α-isomaltosylglucosaccharide-forming enzyme because it is disclosed in detail in Japanese Patent Application No. 5,441/01.

Similarly as the polypeptide disclosed in the application, the α-isomaltosylglucosaccharide-forming enzyme in Experiment 4-1 has an amino acid sequence of the residues 36-1284 of SEQ ID NO:1 shown in parallel with nucleosides.

EXPERIMENT 4-4

Isolation of α-isomaltosyl-transferring Enzyme

The fraction of α-isomaltosyl-transferring enzyme in Experiment 3 was dialyzed against 10 mM phosphate buffer (pH 7.0) containing 1 M ammonium sulfate. The dialyzed solution was centrifuged to remove insoluble impurities, and the resulting supernatant was fed to hydrophobic chromatography using 350 ml of "BUTYL-TOYOPEARL 650 M", a gel commercialized by Tosoh Corporation, Tokyo, Japan. The enzyme adsorbed on the gel and then eluted therefrom at about 0.3 M ammonium sulfate using a linear gradient decreasing from 1 M to 0 M of ammonium sulfate, followed by collecting fractions with the enzyme activity. The fractions were pooled and dialyzed against 10 mM phosphate buffer (pH 7.0) containing 1 M ammonium sulfate. The resulting dialyzed solution was centrifuged to remove impurities and subjected to affinity chromatography using "SEPHACRYL HR S-200" gel to purify the enzyme. The amount of enzyme activity, specific activity, and yield of the α-isomaltosyl-transferring enzyme in each purification step are shown in Table 7.

TABLE 7

| Purification step | Enzyme* activity (unit) | Specific activity of enzyme* (unit/mg protein) | Yield (%) |
|---|---|---|---|
| Culture supernatant | 30,400 | 0.45 | 100 |
| Dialyzed solution after salting out with ammonium sulfate | 28,000 | 1.98 | 92.1 |
| Eluate from ion-exchange column chromatography | 21,800 | 3.56 | 71.7 |
| Eluate from affinity column chromatography | 13,700 | 21.9 | 45.1 |
| Eluate from hydrophobic column chromatography | 10,300 | 23.4 | 33.9 |
| Eluate from affinity column chromatography | 5,510 | 29.6 | 18.1 |

Note:
The symbol "*" means α-isomaltosyl-transferring enzyme.

EXPERIMENT 4-5

Property of α-isomaltosyl-transferring Enzyme

The purified specimen of α-isomaltosyl-transferring enzyme in Experiment 4-4 was subjected to SDS-PAGE using a 7.5% (w/v) of polyacrylamide gel and then the molecular weight was determined by comparing the specimen with the dynamics of standard molecular markers electrophoresed in parallel, commercialized by Bio-Rad Laboratories Inc., Brussels, Belgium, revealing that the enzyme had a molecular weight of about 102,000±20,000 daltons.

A fresh preparation of the above purified specimen was subjected to isoelectrophoresis using a gel containing 2% (w/v) ampholine commercialized by Amersham Corp., Div., Amersham International, Arlington Heights, Ill., USA, and then measured for pHs of protein bands and gel to determine the isoelectric point of the enzyme, revealing that the enzyme had an isoelectric point of about 5.6±0.5.

Figure 13:
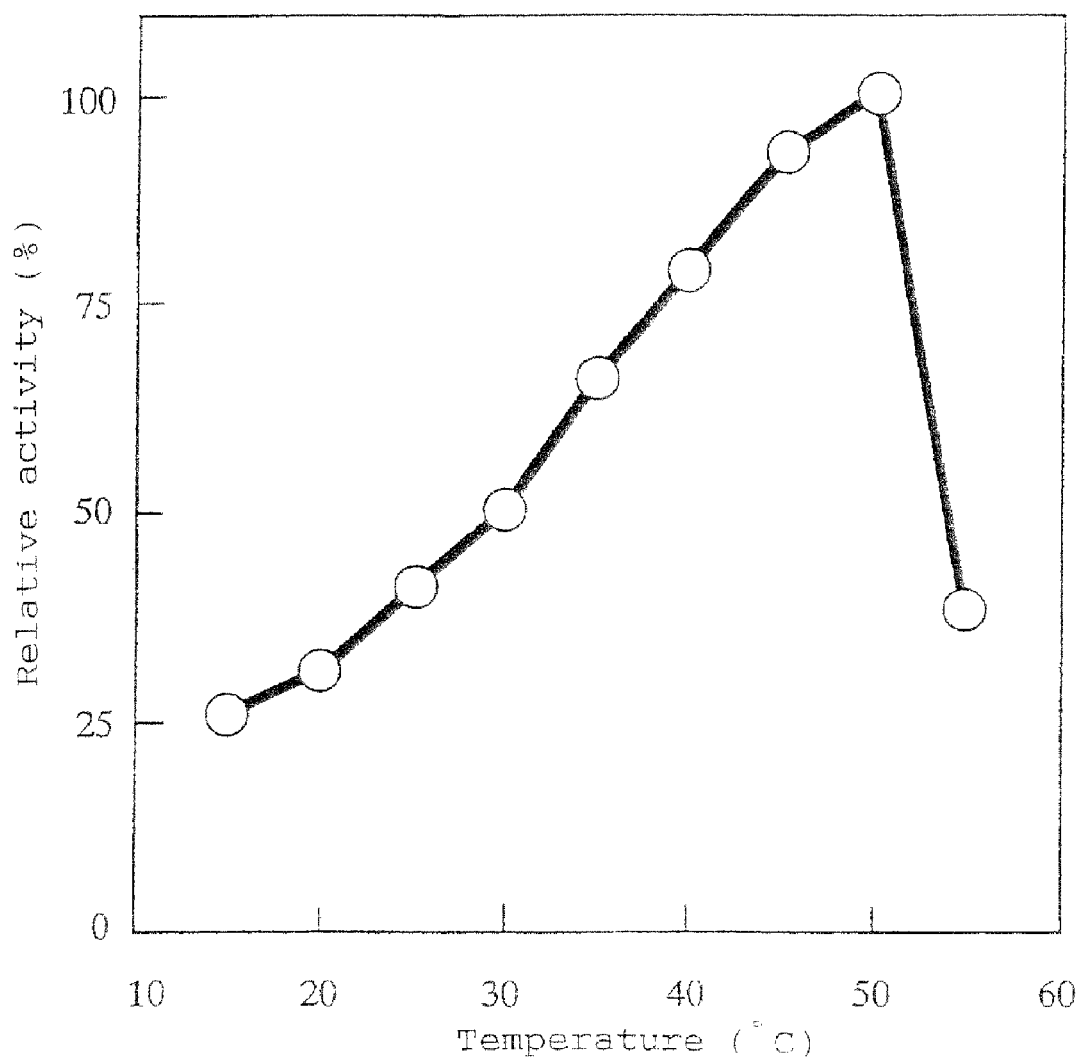
FIG. 13 shows the thermal influence on the enzymatic activity of α-isomaltosyl-transferring enzyme from a microorganism of *Bacillus globisporus* C11 strain.
Figure 14:
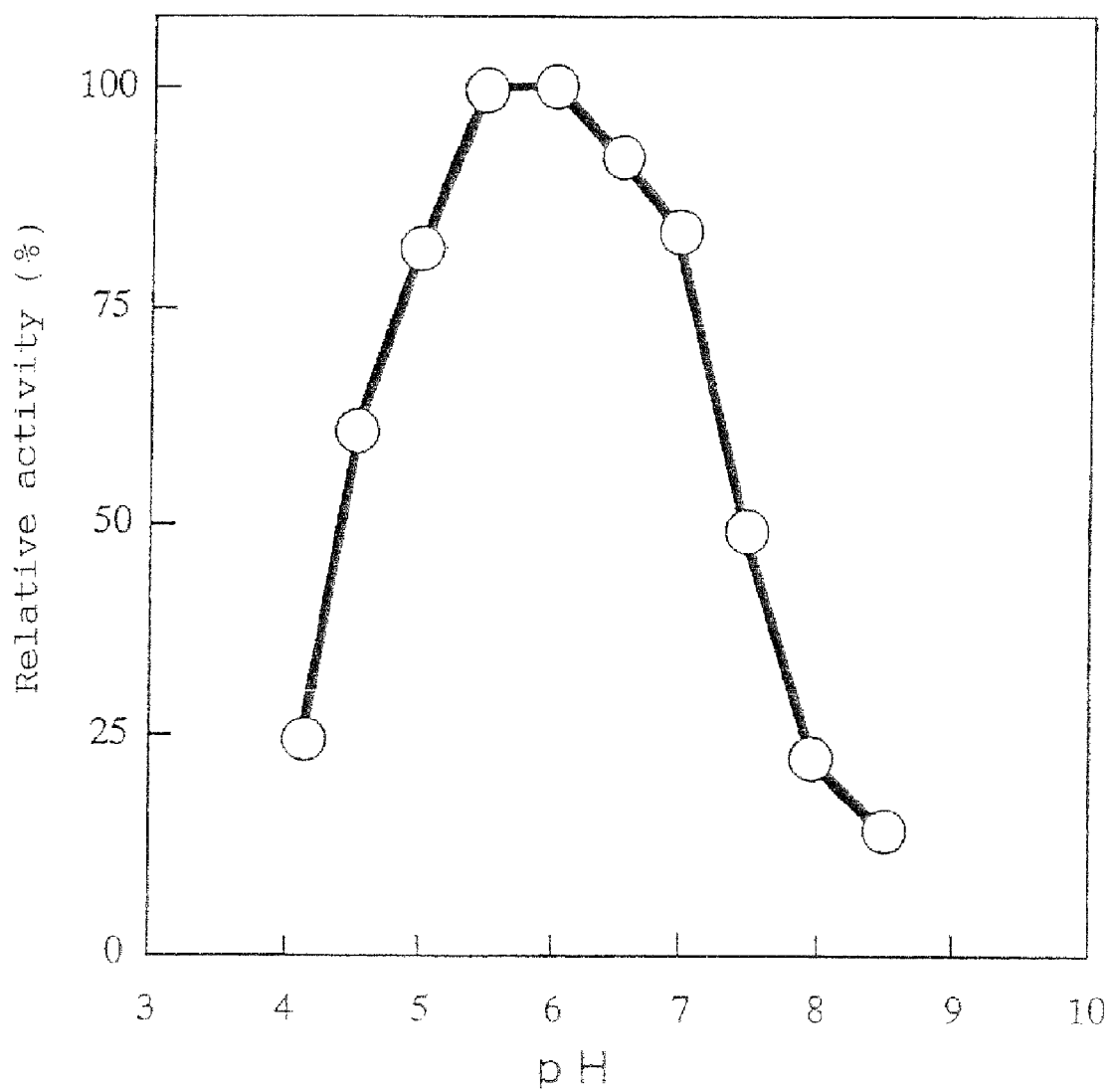
FIG. 14 shows the pH influence on the enzymatic activity of α-isomaltosyl-transferring enzyme from a microorganism of *Bacillus globisporus* C11 strain.
Figure 15:
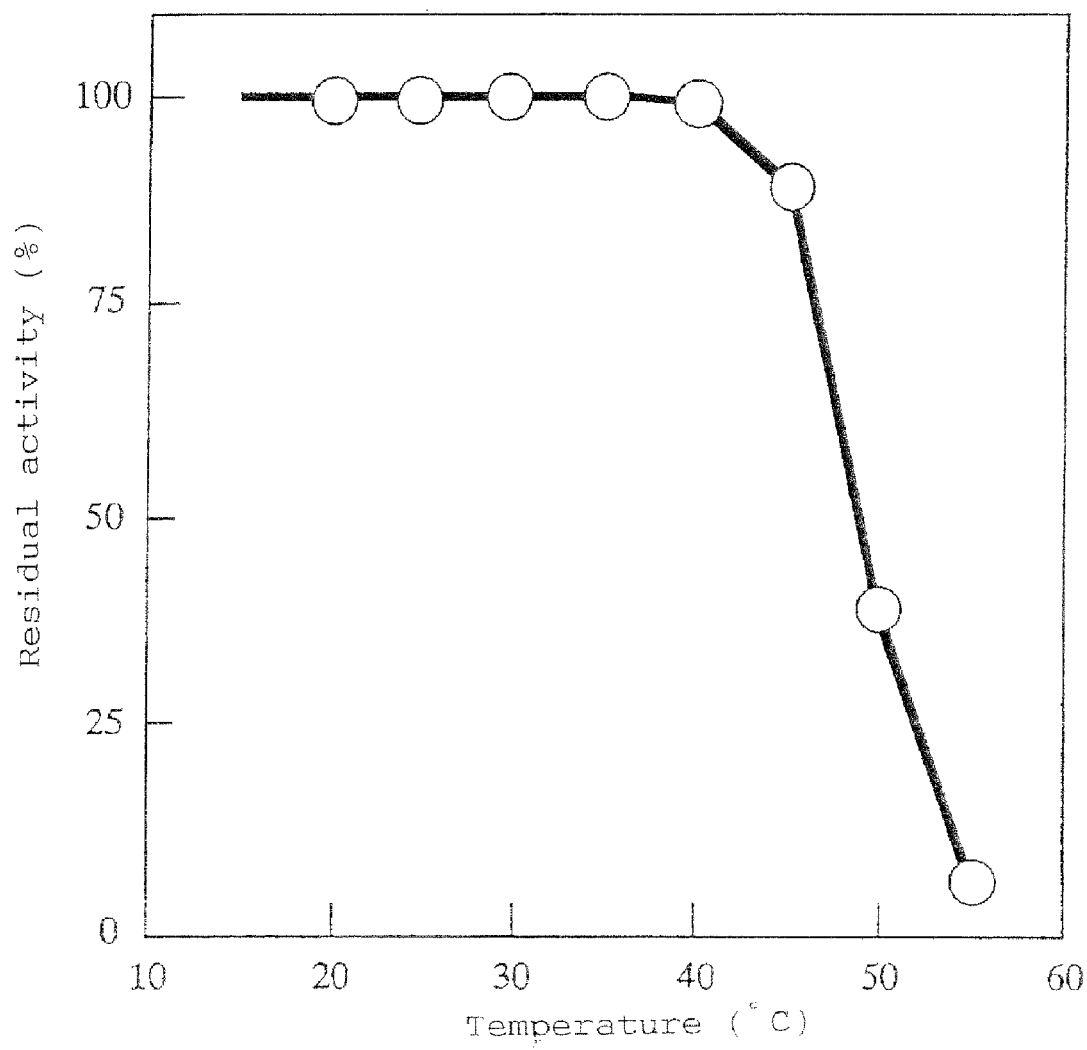
FIG. 15 shows the thermal stability of α-isomaltosyl-transferring enzyme from a microorganism of *Bacillus globisporus* C11 strain.
Figure 16:
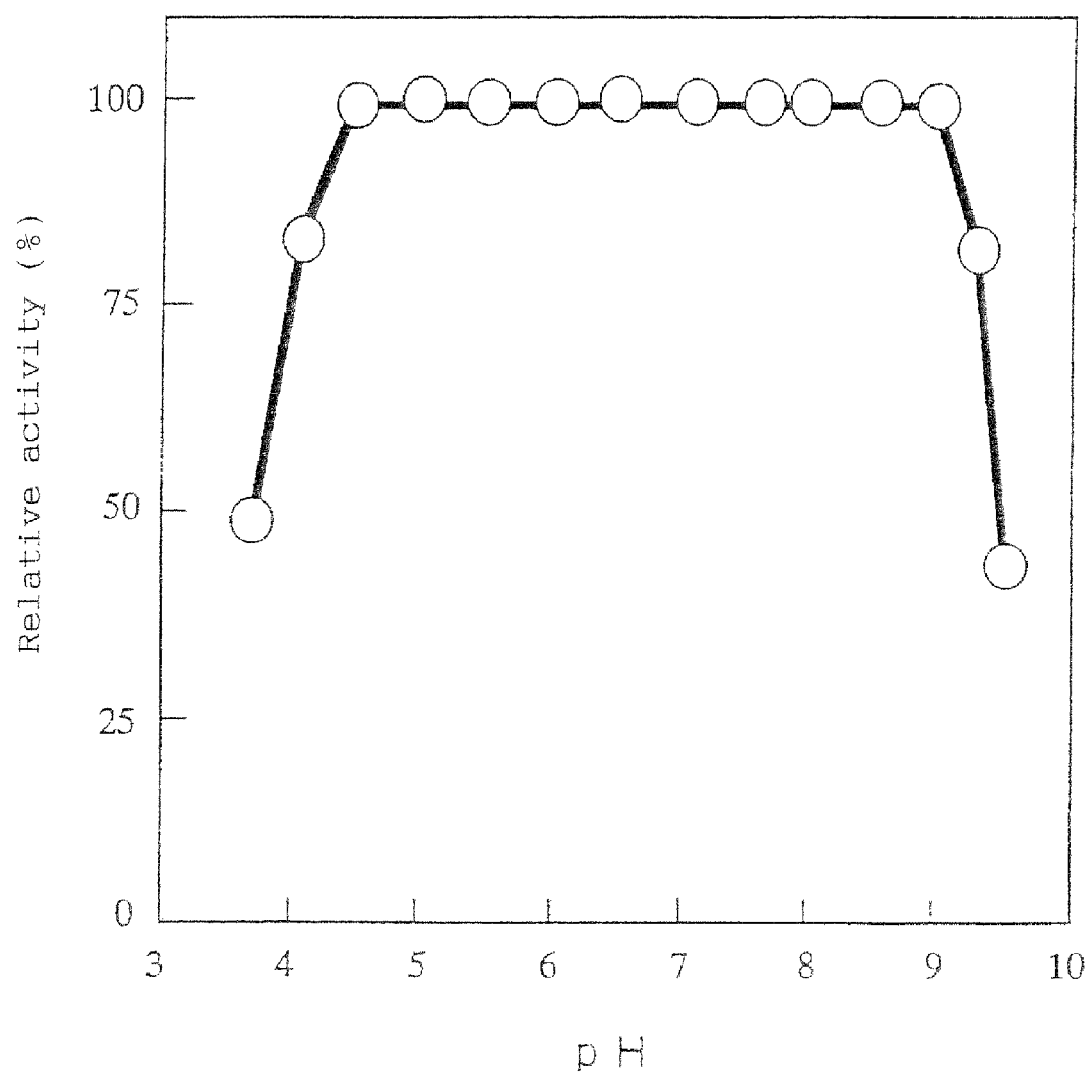
FIG. 16 shows the pH stability of α-isomaltosyl-transferring enzyme from a microorganism of *Bacillus globisporus* C11 strain.

The influence of temperature and pH on the activity of α-isomaltosyl-transferring enzyme was examined in accordance with the assay for enzyme activity. These results are in FIG. 13 (influence of temperature) and FIG. 14 (influence of pH). The optimum temperature of the enzyme was about 50° C. when incubated at pH 6.0 for 30 min. The optimum pH of the enzyme was about 5.5 to about 6.0 when incubated at 35° C. for 30 min. The thermal stability of the enzyme was determined by incubating the testing enzyme solutions in 20 mM acetate buffer (pH 6.0) at prescribed temperatures for 60 min, cooling with water the resulting enzyme solutions, and assaying the remaining enzyme activity of each solution. The pH stability of the enzyme was determined by keeping the testing enzyme solutions in 50 mM buffers having prescribed pHs at 4° C. for 24 hours, adjusting the pH of each solution to 6.0, and assaying the remaining enzyme activity of each solution. These results are respectively in FIG. 15 (thermal stability) and FIG. 16 (pH stability). As a result, the enzyme had thermal stability of up to about 40° C. and pH stability of about 4.5 to about 9.0.

The influence of metal ions on the activity of α-isomaltosyl-transferring enzyme was examined in the presence of 1 mM of each metal-ion according to the assay for the enzyme activity. The results are in Table 8.

TABLE 8

| Metal ion | Relative activity (%) | Metal ion | Relative activity (%) |
|---|---|---|---|
| None | 100 | $Hg^{2+}$ | 2 |
| $Zn^{2+}$ | 83 | $Ba^{2+}$ | 90 |
| $Mg^{2+}$ | 91 | $Sr^{2+}$ | 93 |
| $Ca^{2+}$ | 91 | $Pb^{2+}$ | 74 |
| $Co^{2+}$ | 89 | $Fe^{2+}$ | 104 |
| $Cu^{2+}$ | 56 | $Fe^{3+}$ | 88 |
| $Ni^{2+}$ | 89 | $Mn^{2+}$ | 93 |
| $Al^{3+}$ | 89 | EDTA | 98 |

As evident from the results in Table 8, the enzyme activity was greatly inhibited by $Hg^{2+}$ and also inhibited by $Cu^{2+}$.

It was also found that the enzyme was not activated by $Ca^{2+}$ and not inhibited by EDTA.

EXPERIMENT 4-6

Amino Acid Sequence of α-isomaltosyl-transferring Enzyme

The present specification does not describe in detail the method for analyzing the amino acid sequence of α-isomaltosyl-transferring enzyme because it is disclosed in detail in Japanese Patent Application No. 350,142/00. Similarly as the polypeptide disclosed in the application, the α-isomaltosyl-glucosaccharide-forming enzyme in Experiment 4-4 has an amino acid sequence of the residues 30-1093 of SEQ ID NO:2 shown in parallel with nucleosides.

EXPERIMENT 5

Action of α-isomaltosylglucosaccharide-forming Enzyme on Saccharides

The action of α-isomaltosylglucosaccharide-forming enzyme on saccharides as substrates was tested. First, a solution of maltose, maltotriose, maltotetraose, maltopentaose, maltohexaose, maltoheptaose, isomaltose, isomaltotriose, panose, isopanose, α,α-trehalose (may be abbreviated as "trehalose" hereinafter), kojibiose, nigerose, neotrehalose, cellobiose, gentibiose, maltitol, maltotriitol, lactose, sucrose, erlose, selaginose, maltosyl glucoside, or isomaltosyl glucoside was prepared. To each of the above solutions was added two units/g substrate of the purified specimen of α-isomaltosylglucosaccharide-forming enzyme from *Bacillus globisporus* C9 in Experiment 2-1 or *Bacillus globisporus* C11 in Experiment 4-1, and each resulting solution was adjusted to give a substrate concentration of 2% (w/v) and incubated at 30° C. and pH 6.0 for 24 hours. The solutions before and after the enzymatic reactions were respectively subjected to thin-layer chromatography (abbreviated as "TLC" hereinafter). TLC was carried out in such a manner of separating saccharides by developing the solutions twice each using, as a developer, a mixture solution of n-butanol, pyridine, and water (=6:4:1), and, as a thin-layer plate, "KIESELGEL 60", an aluminum plate (20×20 cm) for TLC commercialized by Merck & Co., Inc., Rahway, USA.; detecting the total saccharides in each mixture solution by spraying a mixture of sulfuric acid and methanol onto the aluminum plates to develop color of the total saccharides and detecting non-reducing saccharides in each mixture solution by the diphenylamine-aniline method. The results on TLC are in Table 9.

degree of at least three and a maltose structure at their non-reducing ends, among the saccharides tested. It was also found that the enzyme only slightly acted on saccharides having a glucose polymerization degree of two, such as maltose, kojibiose, nigerose, neotrehalose, maltotriitol, and erlose.

EXPERIMENT 6

Reaction Product from Maltooligosaccharide

To an aqueous solution containing one percent (w/v) of maltose, maltotriose, maltotetraose, or maltopentaose as a substrate was added the purified specimen of α-isomaltosylglucosaccharide-forming enzyme in Experiment 4-1 in an amount of two units/g solid for the aqueous solution of maltose or maltotriose, 0.2 unit/g solid for that of maltotetraose, and 0.1 unit/g solid for that of maltopentaose, followed by incubation at 35° C. and pH 6.0 for eight hours. After a 10-min incubation at 100° C., the enzymatic reaction was suspended. The resulting reaction solutions were respectively measured for saccharide composition on HPLC using "YMC PACK ODS-AQ303", a column commercialized by YMC Co., Ltd., Tokyo, Japan, at a column temperature of 40° C. and a flow

TABLE 9

| Substrate | Enzymatic action Enzyme of Strain C9 | Enzyme of Strain C11 | Substrate | Enzymatic action Enzyme of Strain C9 | Enzyme of Strain C11 |
|---|---|---|---|---|---|
| Maltose | + | + | Nigerose | + | + |
| Maltotriose | ++ | ++ | Neotrehalose | + | + |
| Maltotetraose | +++ | +++ | Cellobiose | − | − |
| Maltopentaose | +++ | +++ | Gentibiose | − | − |
| Maltohexaose | +++ | +++ | Maltitol | − | − |
| Maltoheptaose | +++ | +++ | Maltotriitol | + | + |
| Isomaltose | − | − | Lactose | − | − |
| Isomaltotriose | − | − | Sucrose | − | − |
| Panose | − | − | Erlose | + | + |
| Isopanose | ++ | ++ | Selaginose | − | − |
| Trehalose | − | − | Maltosylglucoside | ++ | ++ |
| Kojibiose | + | + | Isomaltosylglucoside | − | − |

Note:
Before and after the enzymatic reaction, the symbols "−", "+", "++", and "+++" mean that it showed no change, it showed a slight reduction of the color of substrate spot and the formation of other reaction product, it showed a high reduction of the color of substrate spot and the formation of other reaction product, and it showed a substantial disappearance of the color of substrate spot and the formation of other reaction product, respectively.

As is evident from the results in Table 9, it was revealed that the α-isomaltosylglucosaccharide-forming enzyme acted well on saccharides having both a glucose polymerization rate of 0.5 ml/min of water, and using as a detector "RI-8012", a differential refractometer commercialized by Tosoh Corporation, Tokyo, Japan. The results are in Table 10.

TABLE 10

| Saccharide as reaction product | Substrate | | | |
|---|---|---|---|---|
| | Maltose | Maltotriose | Maltotetraose | Maltopentaose |
| Glucose | 8.5 | 0.1 | 0.0 | 0.0 |
| Maltose | 78.0 | 17.9 | 0.3 | 0.0 |
| Maltotriose | 0.8 | 45.3 | 22.7 | 1.9 |
| Maltotetraose | 0.0 | 1.8 | 35.1 | 19.2 |
| Maltopentaose | 0.0 | 0.0 | 3.5 | 34.4 |
| Maltohexaose | 0.0 | 0.0 | 0.0 | 4.6 |
| Isomaltose | 0.5 | 0.0 | 0.0 | 0.0 |
| Glucosylmaltose | 8.2 | 1.2 | 0.0 | 0.0 |
| Glucosylmaltotriose | 2.4 | 31.5 | 6.8 | 0.0 |
| X | 0.0 | 2.1 | 30.0 | 11.4 |

TABLE 10-continued

| Saccharide | Substrate | | | |
|---|---|---|---|---|
| as reaction product | Maltose | Maltotriose | Maltotetraose | Maltopentaose |
| Y | 0.0 | 0.0 | 1.4 | 26.8 |
| Z | 0.0 | 0.0 | 0.0 | 1.7 |
| Others | 0.6 | 0.1 | 0.2 | 0.0 |

Note:
In the table, glucosylmaltose means α-isomaltosylglucose, alias $6^2$-O-α-glucosylmaltose or panose; glucosylmaltotriose means α-isomaltosylmaltose, alias $6^3$-O-α-glucosylmaltotriose; X means the α-isomaltosylglucotriose in Experiment 7, alias $6^4$-O-α-glucosylmaltotetraose; Y means the α-isomaltosylglucotetraose in Experiment 7, alias $6^5$-O-α-glucosylmaltopentaose; and Z means an unidentified saccharide.

As is evident from the results in Table 10, it was revealed that, after the action of the enzyme, glucose and α-isomaltosylglucose, alias $6^2$-O-α-glucosylmaltose or panose, were mainly formed and maltotriose, isomaltose, and α-isomaltosylmaltose, alias $6^3$-O-α-glucosylmaltotriose were formed in a small amount when the enzyme acted on maltose as a substrate.

Also, it was revealed that, from maltotriose as a substrate, maltose and α-isomaltosylmaltose were mainly formed along with small amounts of glucose, maltotetraose, α-isomaltosylglucose alias $6^2$-O-α-glucosylmaltose or panose, and the product X. It was also found that, from maltotetraose as a substrate, maltotriose and the product X were mainly formed along with small amounts of maltose, maltopentaose, α-isomaltosylmaltose alias $6^3$-O-α-glucosylmaltotriose or panose, and the product Y. Further, it was revealed that, from maltopentaose as a substrate, maltotetraose and the product Y were mainly formed along with small amounts of maltotriose, maltohexaose, and the products X and Z.

The product X as a main product from maltotetraose as a substrate and the product Y as a main product from maltopentaose as a substrate were respectively isolated and purified as follows: The products X and Y were respectively purified on HPLC using "YMC PACK ODS-A R355-15S-15 12A", a separatory HPLC column commercialized by YMC Co., Ltd., Tokyo, Japan, to isolate a specimen of the product X having a purity of at least 99.9% from the reaction product from maltotetraose in a yield of about 8.3%, d.s.b., and a specimen of the product Y having a purity of at least 99.9% from the reaction product from maltotetraose in a yield of about 11.5%, d.s.b.

EXPERIMENT 7

Structural Analysis on Reaction Product

Figure 17:
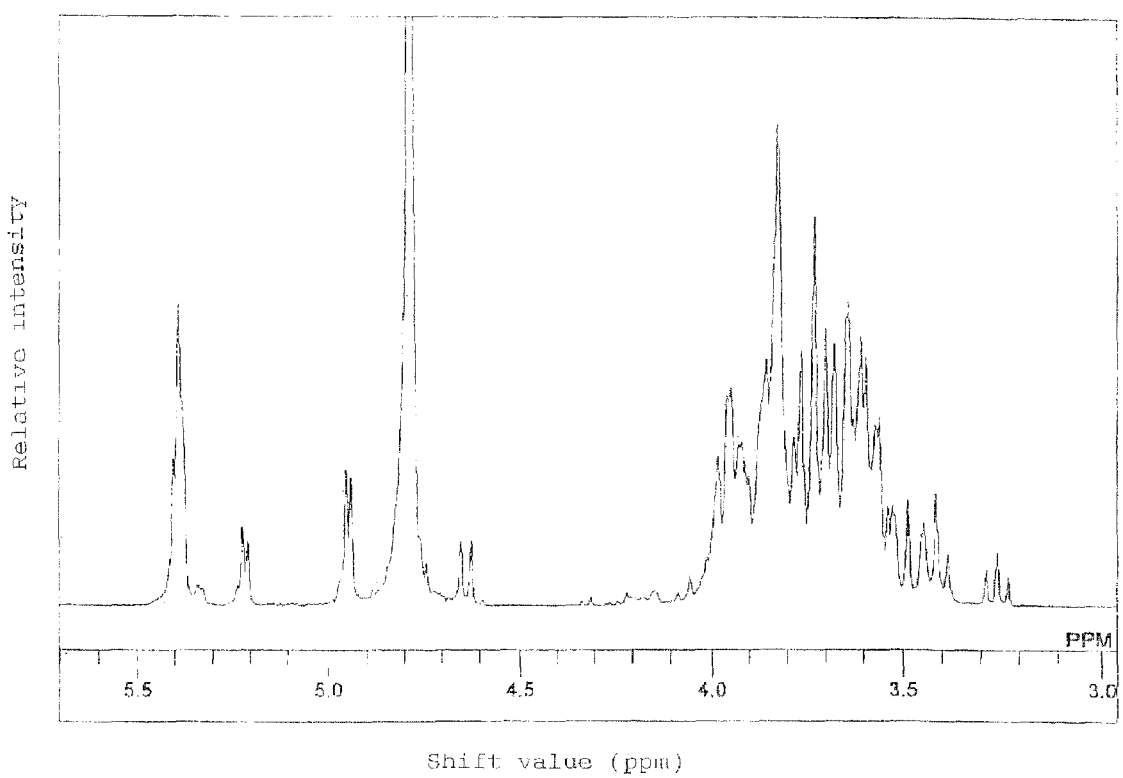
FIG. 17 is a nuclear resonance spectrum ($^1$H-NMR) of α-isomaltosylmaltotriose, obtained by the enzymatic reaction using α-isomaltosylglucosaccharide-forming enzyme.
Figure 18:
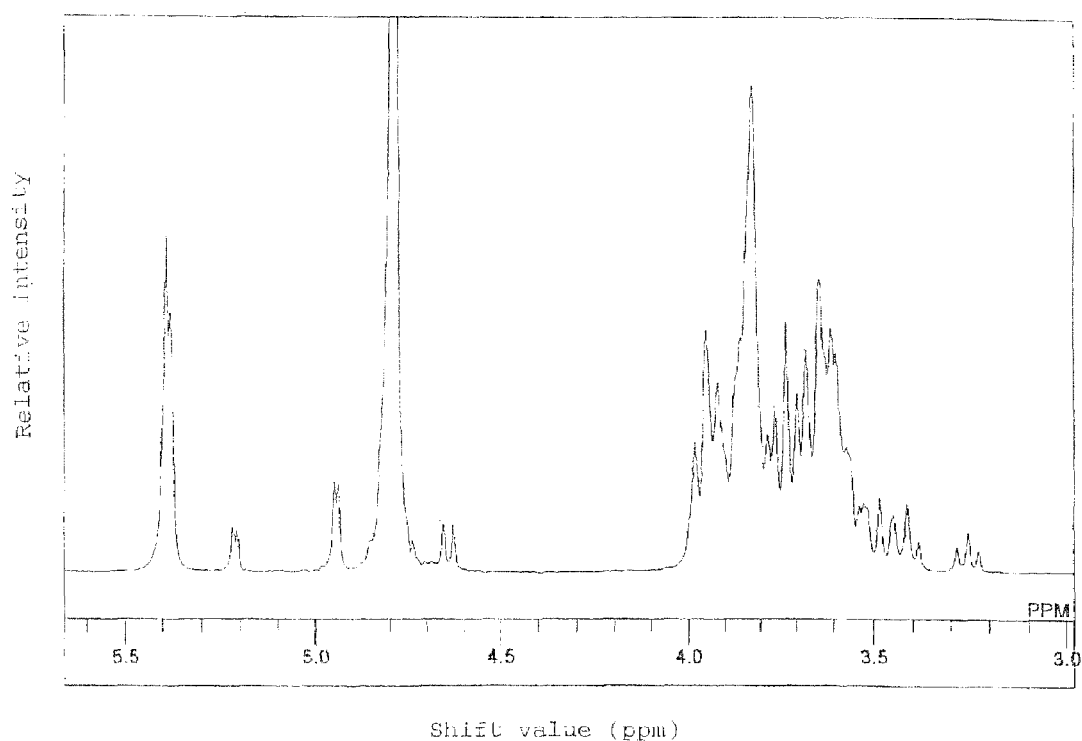
FIG. 18 is a nuclear resonance spectrum ($^1$H-NMR) of α-isomaltosylmaltotetraose, obtained by the enzymatic reaction using α-isomaltosylglucosaccharide-forming enzyme.
Figure 19:
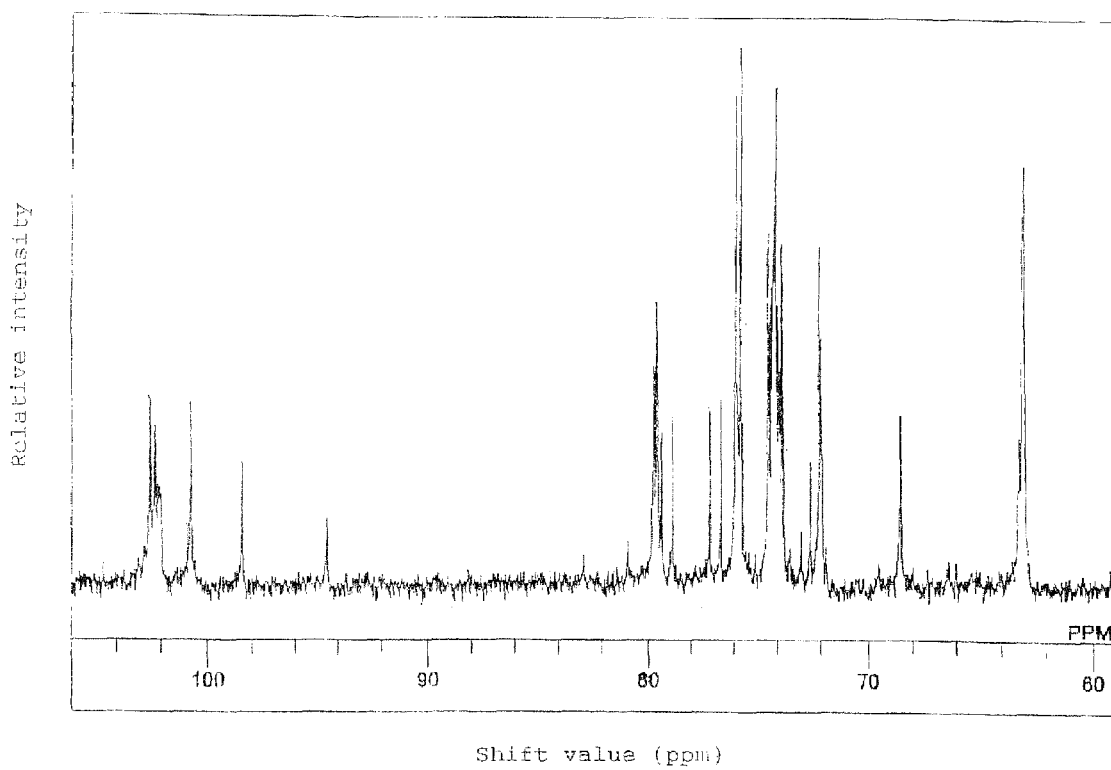
FIG. 19 is a nuclear resonance spectrum ($^{13}$C-NMR) of α-isomaltosylmaltotriose, obtained by the enzymatic reaction using α-isomaltosylglucosaccharide-forming enzyme.
Figure 20:
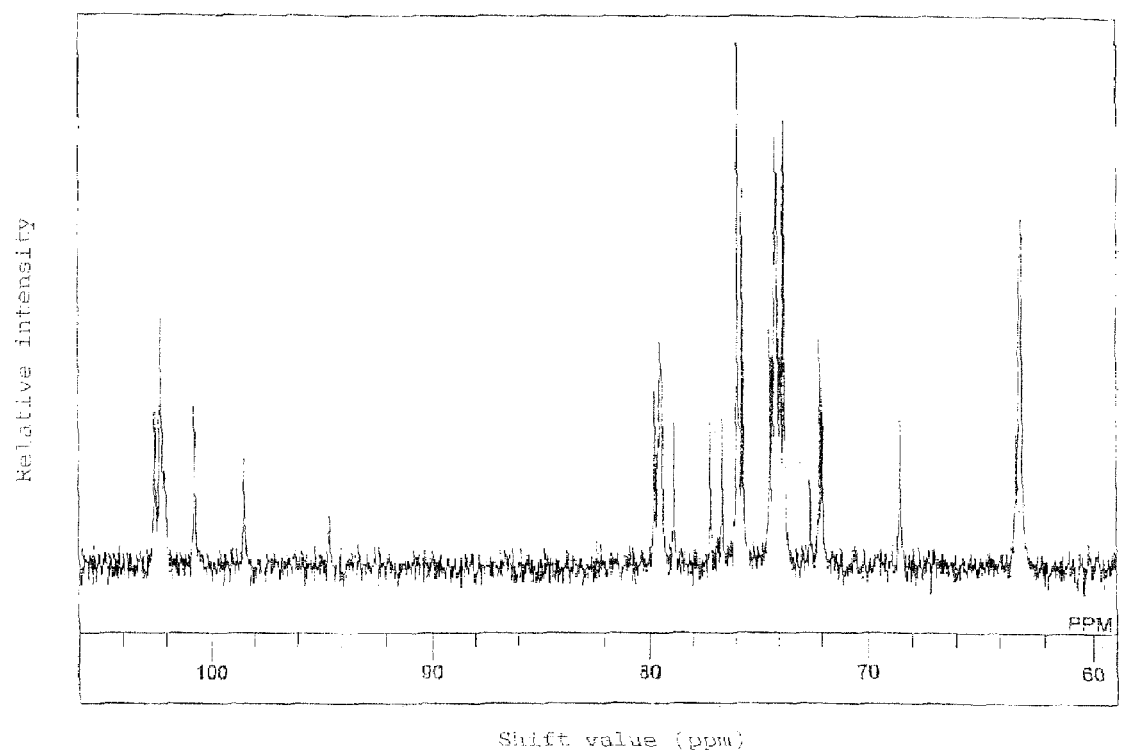
FIG. 20 is a nuclear resonance spectrum ($^{13}$C-NMR) of α-isomaltosylmaltotetraose, obtained by the enzymatic reaction using α-isomaltosylglucosaccharide-forming enzyme.

Using the products X and Y obtained by the method in Experiment 6, they were subjected to methyl analysis and NMR analysis in a usual manner. The results on their methyl analyses are in Table 11. For the results on their NMR analyses, FIG. 17 is a $^1$H-NMR spectrum for the product X and FIG. 18 is for the product Y. The $^{13}$C-NMR spectra for the products X and Y are respectively in FIGS. 19 and 20, and their assignments are in Table 12.

TABLE 11

| Analyzed | Ratio | |
|---|---|---|
| methyl compound | Product X | Product Y |
| 2,3,4-trimethyl compound | 1.00 | 1.00 |
| 2,3,6-trimethyl compound | 3.05 | 3.98 |
| 2,3,4,6-tetramethyl compound | 0.82 | 0.85 |

TABLE 12

| | | NMR chemical shift value (ppm) | |
|---|---|---|---|
| Glucose number | Carbon number | Product X | Product Y |
| a | 1a | 100.8 | 100.8 |
| | 2a | 74.2 | 74.2 |
| | 3a | 75.8 | 75.7 |
| | 4a | 72.2 | 72.2 |
| | 5a | 74.5 | 74.5 |
| | 6a | 63.2 | 63.1 |
| b | 1b | 102.6 | 102.6 |
| | 2b | 74.2 | 74.2 |
| | 3b | 75.8 | 75.7 |
| | 4b | 72.1 | 72.1 |
| | 5b | 74.0 | 74.0 |
| | 6b | 68.6 | 68.6 |
| c | 1c | 102.3 | 102.3 |
| | 2c | 74.2 | 74.2 |
| | 3c | 76.0 | 76.0 |
| | 4c | 79.6 | 79.5 |
| | 5c | 73.9 | 73.9 |
| | 6c | 63.2 | 63.1 |
| d | 1d | 102.2 | 102.3 |
| | 2d | 74.0 (α), 74.4 (β) | 74.2 |
| | 3d | 76.0 | 76.0 |
| | 4d | 79.8 | 79.5 |
| | 5d | 73.9 | 73.9 |
| | 6d | 63.2 | 63.1 |
| e | 1e | 94.6 (α), 98.5 (β) | 102.1 |
| | 2e | 74.2 (α), 76.7 (β) | 74.0 (α), 74.4 (β) |
| | 3e | 75.9 (α), 78.9 (β) | 76.0 |
| | 4e | 79.6 (α), 79.4 (β) | 79.8 |
| | 5e | 72.6 (α), 77.2 (β) | 73.9 |
| | 6e | 63.4 (α), 63.4 (β) | 63.1 |
| f | 1f | | 94.6 (α), 98.5 (β) |
| | 2f | | 74.2 (α), 76.7 (β) |
| | 3f | | 76.0 (α), 78.9 (β) |
| | 4f | | 79.6 (α), 79.5 (β) |
| | 5f | | 72.6 (α), 77.2 (β) |
| | 6f | | 63.3 (α), 63.3 (β) |

Based on these results, the product X formed from maltotetraose via the action of the α-isomaltosylglucosaccharide-forming enzyme was revealed as a pentasaccharide, in which a glucose residue binds via the α-linkage to OH-6 of glucose at the non-reducing end of maltotetraose, i.e., α-isomaltosylmaltotriose, alias $6^4$-O-α-glucosylmaltotetraose, represented by Formula 1.

α-D-Glcp-(1→6)-α-D-Glcp-(1→4)-α-D-Glcp-(1→4)-α-D-Glcp-(1→4)-D-Glcp       Formula 1:

The product Y formed from maltopentaose was revealed as a hexasaccharide, in which a glucosyl residue binds via the α-linkage to OH-6 of glucose at the non-reducing end of maltopentaose, i.e., α-isomaltosylglucotetraose alias 6⁵-O-α-glucosylmaltopentaose, represented by Formula 2.

α-D-Glcp-(1→6)-α-D-Glcp-(1→4)-α-D-Glcp-(1→4)-
α-D-Glcp-(1→4)-α-D-Glcp-(1→4)-D-Glcp     Formula 2:

Based on these results, it was concluded that the α-isomaltosylglucosaccharide-forming enzyme acts on maltooligosaccharides as shown below:

(1) The enzyme acts on maltooligosaccharide substrates having a glucose polymerization degree of at least two where glucoses are linked together via the α-1,4 linkage, and catalyzes the intermolecular 6-glucosyl-transferring reaction in such a manner of transferring a glucosyl residue at the non-reducing end of a maltooligosaccharide molecule to C-6 of the non-reducing end of other maltooligosaccharide molecule to form both an α-isomaltosylglucosaccharide alias 6-O-α-glucosylmaltooligosaccharide, having a 6-O-α-glucosyl residue and a higher glucose polymerization degree by one as compared with the intact substrate, and a maltooligosaccharide with a reduced glucose polymerization degree by one as compared with the intact substrate; and (2) The enzyme slightly catalyzes the 4-glucosyl-transferring reaction and forms both a maltooligosaccharide, having an increased glucose polymerization degree by one as compared with the intact substrate, and a maltooligosaccharide having a reduced glucose polymerization degree by one as compared with the intact substrate.

EXPERIMENT 8

Specificity of Saccharide Transferring Reaction Acceptor

Using different saccharides, it was tested whether the saccharides were used as saccharide transferring reaction acceptors for the α-isomaltosylglucosaccharide-forming enzyme. A 1.6% solution, as a solution of saccharide transferring reaction acceptor, of D-glucose, D-xylose, L-xylose, D-galactose, D-fructose, D-mannose, D-arabinose, D-fucose, L-sorbose, L-rhamnose, methyl-α-glucopyranoside (methyl-α-glucose), methyl-β-glucopyranoside (methyl-α-glucose), N-acetyl-glucosamine, sorbitol, α,α-trehalose, isomaltose, isomaltotriose, cellobiose, gentibiose, maltitol, lactose, sucrose, α-cyclodextrin, β-cyclodextrin, or γ-cyclodextrin, was prepared. To each solution with a saccharide concentration was added "PINE-DEX #100", a partial starch hydrolysate, as a saccharide donor, to give a concentration of 4%, and admixed with one unit/g saccharide donor, d.s.b., of either of purified specimens of α-isomaltosylglucosaccharide-forming enzyme from Bacillus globisporus C9 strain obtained by the method in Experiment 2-1, Bacillus globisporus C11 strain obtained by the method in Experiment 4-1. The resulting mixture solutions were incubated at 30° C. and pH 6.0 except that the enzyme from Arthrobacter globiformis A19 strain was incubated at pH 8.4 for 24 hours. The reaction mixtures of the post-enzymatic reactions were analyzed on gas chromatography (abbreviated as "GLC" hereinafter) for monosaccharides and disaccharides as acceptors, and on HPLC for trisaccharides as acceptors to confirm whether these saccharides could be used as their saccharide transferring reaction acceptors. In the case of performing GLC, the following apparatuses and conditions are used: GLC apparatus, "GC-16A" commercialized by Shimadzu Corporation, Tokyo, Japan; column, a stainless-steel column, 3 mm in diameter and 2 m in length, packed with 2% "SILICONE OV-17/CHROMOSOLV W", commercialized by GL Sciences Inc., Tokyo, Japan; carrier gas, nitrogen gas at a flow rate of 40 ml/min under temperature conditions of increasing from 160° C. to 320° C. at an increasing temperature rate of 7.5° C./min; and detection, a hydrogen flame ionization detector.

In the case of HPLC analysis, the apparatuses and conditions used were: HPLC apparatus, "CCPD" commercialized by Tosoh Corporation, Tokyo, Japan; column, "ODS-AQ-303" commercialized by YMC Co., Ltd., Tokyo, Japan; eluent, water at a flow rate of 0.5 ml/min; and detection, a differential refractometer. The results are in Table 13.

TABLE 13

| Saccharide | Product of saccharide transferring reaction | | Saccharide | Product of saccharide transferring reaction | |
|---|---|---|---|---|---|
| | Enzyme of Strain C9 | Enzyme of Strain C11 | | Enzyme of Strain C9 | Enzyme of Strain C11 |
| D-Glucose | + | + | Sorbitol | − | − |
| D-Xylose | ++ | ++ | Trehalose | ++ | ++ |
| L-Xylose | ++ | ++ | Isomaltose | ++ | ++ |
| D-Galactose | + | + | Isomaltotriose | ++ | ++ |
| D-Fructose | + | + | Cellobiose | ++ | ++ |
| D-Mannose | − | − | Gentibiose | ++ | ++ |
| D-Arabinose | ± | ± | Maltitol | ++ | ++ |
| D-Fucose | + | + | Lactose | ++ | ++ |
| L-Sorbose | + | + | Sucrose | ++ | ++ |
| L-Rhamnose | − | − | α-Cyclodextrin | − | − |
| Methyl-α-glucopyranoside | ++ | ++ | β-Cyclodextrin | − | − |
| Methyl-β-glucopyranoside | ++ | ++ | γ-Cyclodextrin | − | − |
| N-Acetyl-glucosamine | + | + | | | |

Note:
In the table, the symbols "−", "±", "+", and "++" mean that no saccharide-transferred product was detected through transferring reaction to acceptor; a saccharide-transferred product was detected in an amount of less than one percent through transfer reaction to acceptor; a saccharide-transferred product was detected in an amount of at least one percent but less than ten percent through transferring reaction to acceptor; and a saccharide-transferred product was detected in an amount of at least ten percent through transferring reaction to acceptor.

As is evident from the results in Table 13, α-isomaltosyl-glucosaccharide-forming enzyme utilizes different types of saccharides as saccharide transfer acceptors, particularly, the enzyme has a higher saccharide transferring action, particularly, on D-/L-xylose, methyl-α-glucopyranoside, methyl-β-glucopyranoside, α,α-trehalose, isomaltose, isomaltotriose, cellobiose, gentibiose, maltitol, lactose, and sucrose; then on D-glucose, D-fructose, D-fucose, L-sorbose, and N-acetyl-glucosamine, as well as D-arabinose.

EXPERIMENT 9

Preparation of Cyclotetrasaccharide from Culture

A liquid medium consisting of 5% (w/v) of "PINE-DEX #1", a partial starch hydrolysate commercialized by Matsutani Chemical Ind., Tokyo, Japan, 1.5% (w/v) of "ASAHIME-AST", a yeast extract commercialized by Asahi Breweries, Ltd., Tokyo, Japan, 0.1% (w/v) of dipotassium phosphate, 0.06% (w/v) of sodium phosphate dodecahydrate, 0.05% (w/v) magnesium sulfate heptahydrate, and water was placed in a 500-ml Erlenmeyer flask in an amount of 100 ml, sterilized by autoclaving at 121° C. for 20 min, cooled, and then seeded with *Bacillus globisporus* C9 strain, FERM BP-7143, followed by culturing under rotary-shaking conditions at 27° C. and 230 rpm for 48 hours and centrifuging the resulting culture to remove cells to obtain a supernatant. The supernatant was autoclaved at 120° C. for 15 min and then cooled, and the resulting insoluble substances were removed by centrifugation to obtain a supernatant. About 90 ml of the supernatant was adjusted to pH 5.0 and 45° and then incubated for 24 hours after admixed with 1,500 units per gram of solids of "TPANSGLUCOSIDASE L AMANO™", an α-glucosidase commercialized by Amano Pharmaceutical Co., Ltd., Aichi, Japan, and 75 units per gram of solids of a glucoamylase commercialized by Nagase Biochemicals, Ltd., Kyoto, Japan. Thereafter, the resulting culture was adjusted to pH 12 by the addition of sodium hydroxide and boiled for two hours to decompose the remaining reducing sugars. After removing insoluble substances by filtration, the resulting solution was decolored and desalted with "DIAION PK218" and "DIAION WA30", cation exchange resins commercialized by Mitsubishi Chemical Industries, Ltd., Tokyo, Japan, and further desalted with "DIAION SK-1B", commercialized by Mitsubishi Chemical Industries, Ltd., Tokyo, Japan, and "AMBERLITE IRA411", an anion exchange resin commercialized by Japan Organo Co., Ltd., Tokyo, Japan, followed by decoloring with an activated charcoal, membrane filtered, concentrated by an evaporator, and lyophilized in vacuo to obtain about 0.6 g, d.s.b., of a saccharide powder with a cyclotetrasaccharide content of 99.9% or higher.

EXPERIMENT 10

Formation of Cyclotetrasaccharide

The formation test on cyclotetrasaccharide by the action of α-isomaltosylglucosaccharide-forming enzyme and α-isomaltosyl-transferring enzyme was conducted using saccharides.

Using as saccharides maltose, maltotriose, maltotetraose, maltopentaose, amylose, soluble starch, "PINE-DEX #100", a partial starch hydrolyzate commercialized by Matsutani Chemical Ind., Tokyo, Japan, or glycogen from oyster commercialized by Wako Pure Chemical Industries Ltd., Tokyo, Japan, solutions containing each of the saccharides were respectively prepared.

To each of these solutions with a respective concentration of 0.5%, one unit/g solid of a purified specimen of α-isomaltosylglucosaccharide-forming enzyme from Strain C11 obtained by the method in Experiment 4-1 and 10 units/g solid of a purified specimen of α-isomaltosyl-transferring enzyme from Strain C11 obtained by the method in Experiment 4-4, and the resulting mixture was subjected to an enzymatic reaction at 30° C. and pH 6.0. The enzymatic conditions were the following four systems:

(1) After the α-isomaltosylglucosaccharide-forming enzyme was allowed to act on a saccharide solution for 24 hours, the enzyme was inactivated by heating, and then the α-isomaltosyl-transferring enzyme was allowed to act on the resulting mixture for 24 hours and inactivated by heating;

(2) After the α-isomaltosylglucosaccharide-forming enzyme and the α-isomaltosyl-transferring enzyme were allowed in combination to act on a saccharide solution for 24 hours, then the saccharides were inactivated by heating;

(3) After only the α-isomaltosylgluco-saccharide-forming enzyme was allowed to act on a saccharide solution for 24 hours, then the enzyme was inactivated by heating; and (4) After only the α-isomaltosyl-transferring enzyme was allowed to act on a saccharide solution for 24 hours, then the enzyme was inactivated by heating.

To determine the formation level of cyclotetra-saccharide in each reaction mixture after heating, the reaction mixture was treated with α-glucosidase and glucoamylase similarly as in Experiment 1 to hydrolyze the remaining reducing oligosaccharides, followed by quantitation of cyclotetrasaccharide on HPLC. The results are in Table 14.

TABLE 14

| Substrate | Formation yield of cyclotetrasaccharide (%) | | | |
|---|---|---|---|---|
| | A | B | C | D |
| Maltose | 4.0 | 4.2 | 0.0 | 0.0 |
| Maltotriose | 10.2 | 12.4 | 0.0 | 0.0 |
| Maltotetraose | 11.3 | 21.5 | 0.0 | 0.0 |
| Maltopentaose | 10.5 | 37.8 | 0.0 | 0.0 |
| Amylose | 3.5 | 31.6 | 0.0 | 0.0 |
| Soluble starch | 5.1 | 38.2 | 0.0 | 0.0 |
| Partial starch hydrolyzate | 6.8 | 63.7 | 0.0 | 0.0 |
| Glycogen | 10.2 | 86.9 | 0.0 | 0.0 |

Note:
The symbols "A", "B", "C" and "D" mean that α-isomaltosylglucosaccharide-forming enzyme was first allowed to act on a substrate and then α-isomaltosyl-transferring enzyme was allowed to act on the resulting mixture, the α-isomaltosylglucosaccharide-forming enzyme and α-isomaltosyl-transferring enzyme were allowed to coact on a substrate, only α-isomaltosylglucosaccharide-forming enzyme was allowed to act on a substrate, and only α-isomaltosyl-transferring enzyme was allowed to act on a substrate.

As is evident from the results in Table 14, no cyclotetrasaccharide was formed from any of the saccharides tested by the action of only α-isomaltosylglucosaccharide-forming enzyme or α-isomaltosyl-transferring enzyme, but cyclotetrasaccharide was formed by the coaction of these enzymes. It was revealed that the formation level of cyclotetrasaccharide was relatively low as below about 11% when α-isomaltosyl-transferring enzyme was allowed to act on the substrate saccharides after the action of α-isomaltosylglucosaccharide-forming enzyme, while the formation level was increased by simultaneously allowing the enzymes to act on every saccharide tested, particularly, increased to about 87% and about 64% when the enzymes were allowed to act on glycogen and partial starch hydrolyzate, respectively.

Based on the reaction properties of α-isomaltosylglucosaccharide-forming enzyme and α-isomaltosyl-transferring enzyme, the formation mechanism of cyclotetrasaccharide by the coaction of these enzymes is estimated as follows:

(1) α-Isomaltosylglucosaccharide-forming enzyme acts on a glucose residue at the non-reducing end of an α-1,4 glucan chain of glycogen and partial starch hydrolyzates, etc., and intermolecularly transfers the glucose residue to OH-6 of a glucose residue at the non-reducing end of other α-1,4 glucan chain of glycogen to form an α-1,4 glucan chain having an α-isomaltosyl residue at the non-reducing end;

(2) α-Isomaltosyl-transferring enzyme acts on the α-1,4 glucan chain having an α-isomaltosyl residue at the non-reducing end and intermolecularly transfers the isomaltosyl residue to C-3 of glucose residue at the non-reducing end of other α-1,4 glucan chain having isomaltosyl residue at the non-reducing end to form an α-1,4 glucan chain having an isomaltosyl-1,3-isomaltosyl residue at the non-reducing end;

(3) Then, α-isomaltosyl-transferring enzyme acts on the α-1,4 glucan chain having an isomaltosyl-1,3-isomaltosyl residue at the non-reducing end and releases the isomaltosyl-1,3-isomaltosyl residue from the α-1,4 glucan chain via the intramolecular transferring reaction to cyclize the released isomaltosyl-1,3-isomaltosyl residue into cyclotetra-saccharide;

(4) From the released α-1,4 glucan chain, cyclotetrasaccharide is newly formed through the sequential steps (1) to (3). Thus, it is estimated that the coaction of α-isomaltosylglucosaccharide-forming enzyme and α-isomaltosyl-transferring enzyme increases the formation of cyclotetra-saccharide in the above sequential manner.

EXPERIMENT 11

Influence of Liquefaction Degree of Starch

A 15% corn starch suspension was prepared, admixed with 0.1% calcium carbonate, adjusted to pH 6.0, and then mixed with 0.2-2.0% per gram starch of "TERMAMYL 60L", an α-amylase specimen commercialized by Novo Indutri A/S, Copenhagen, Denmark, followed by the enzymatic reaction at 95° C. for 10 min. Thereafter, the reaction mixture was autoclaved at 120° C. for 20 min, promptly cooled to about 35° C. to obtain a liquefied starch with a DE (dextrose equivalent) of 3.2-20.5. To the liquefied starch were added two units/g solid of a purified specimen of α-isomaltosylglucosaccharide-forming enzyme from Strain C11 obtained by the method in Experiment 4-1, and 20 units/g solid of a purified specimen of α-isomaltosyl-transferring enzyme from Strain C11 obtained by the method in Experiment 4-4, followed by the incubation at 35° C. for 24 hours. After completion of the reaction, the reaction mixture was heated at 100° C. for 15 min to inactivate the remaining enzymes. Then, the reaction mixture thus obtained was treated with α-glucosidase and glucoamylase similarly as in Experiment 1 to hydrolyze the remaining reducing oligosaccharides, followed by quantifying the formed cyclotetrasaccharide on HPLC. The results are in Tale 15.

TABLE 15

| Amount of α-amylase per starch (%) | DE | Yield of cyclotetrasaccharide (%) |
|---|---|---|
| 0.2 | 3.2 | 54.5 |
| 0.4 | 4.8 | 50.5 |
| 0.6 | 7.8 | 44.1 |
| 1.0 | 12.5 | 39.8 |
| 1.5 | 17.3 | 34.4 |
| 2.0 | 20.5 | 30.8 |

As is evident from the results in Table 15, it was revealed that the formation of cyclotetrasaccharide by the coaction of α-isomaltosylglucosaccharide-forming enzyme and α-isomaltosyl-transferring enzyme is influenced by the liquefaction degree of starch, i.e., the lower the liquefaction degree or the lower the DE, the more the yield of cyclotetrasaccharide from starch becomes. On the contrary, the higher the liquefaction degree or the high the DE, the lower the yield of cyclotetrasaccharide from starch becomes. It was revealed that a suitable liquefaction degree is a DE of about 20 or lower, preferably, DE of about 12 or lower, more preferably, DE of about five or lower.

EXPERIMENT 12

Influence of Concentration of Partial Starch Hydrolyzate

Aqueous solutions of "PINE-DEX #100", a partial starch hydrolyzate with a DE of about two to about five, having a final concentration of 0.5-40%, were prepared and respectively admixed with one unit/g solid of a purified specimen of α-isomaltosylglucosaccharide-forming enzyme from Strain C11 obtained by the method in Experiment 4-1 and 10 units/g solid of a purified specimen of α-isomaltosyl-transferring enzyme from Strain C11 obtained by the method in Experiment 4-4, followed by the coaction of the enzymes at 30° C. and pH 6.0 for 48 hours. After completion of the reaction, the reaction mixture was heated at 100° C. for 15 min to inactivate the remaining enzymes, and then treated with α-glucosidase and glucoamylase similarly as in Experiment 1 to hydrolyze the remaining reducing oligosaccharides, followed by quantifying the formed cyclotetrasaccharide on HPLC. The results are in Table 16.

TABLE 16

| Concentration of PINE-DEX (%) | Formation yield of cyclotetrasaccharide (%) |
|---|---|
| 0.5 | 63.6 |
| 2.5 | 62.0 |
| 5 | 60.4 |
| 10 | 57.3 |
| 15 | 54.6 |
| 20 | 51.3 |
| 30 | 45.9 |
| 40 | 35.9 |

As is evident from the results shown in Table 16, the formation yield of cyclotetrasaccharide was about 64% at a low concentration of 0.5%, while it was about 40% at a high concentration of 40%. This indicated that the formation yield of cyclotetrasaccharide increased depending on the concentration of partial starch hydrolyzate as a substrate. The result revealed that the formation yield of cyclotetrasaccharide increased as the decrease of partial starch hydrolyzate.

EXPERIMENT 13

Influence of the Addition of Cyclodextrin Glucanotransferase

A 15% aqueous solution of "PINE-DEX #100", a partial starch hydrolyzate was prepared and admixed with one unit/g solid of a purified specimen of α-isomaltosylglucosaccharide-forming enzyme from Strain C11 obtained by the method in Experiment 4-1, 10 units/g solid of a purified specimen of α-isomaltosyl-transferring enzyme from Strain C11 obtained by the method in Experiment 4-4, and 0-0.5 unit/g solid of cyclodextrin glucanotransferase (CGTase) from a microorganism of the species Bacillus stearothermophilus, followed by the coaction of these enzymes at 30° C. and pH 6.0 for 48 hours. After completion of the reaction, the reaction mixture was heated at 100° C. for 15 min to inactivate the remaining enzymes, and then treated with "TRANS-GLUCOSIDASE L AMANO™", an α-glucosidase commercialized by Amano Pharmaceutical Co., Ltd., Aichi, Japan, and a glucoamylase specimen commercialized by Nagase Biochemicals, Ltd., Kyoto, Japan, to hydrolyze the remaining reducing oligosaccharides, followed by quantifying the formed cyclotetrasaccharide on HPLC. The results are shown in Table 17.

TABLE 17

| Amount of CGTase added (unit) | Formation yield of cyclotetrasaccharide (%) |
|---|---|
| 0 | 54.6 |
| 2.5 | 60.1 |
| 5 | 63.1 |
| 10 | 65.2 |

As is evident from the results in Table 17, it was revealed that the addition of CGTase increased the formation yield of cyclotetrasaccharide.

EXPERIMENT 15

Preparation of Isomaltose-releasing Enzyme

A liquid nutrient culture medium, consisting of 3.0% (w/v) of dextran, 0.7% (w/v) of peptone, 0.2% (w/v) of dipotassium phosphate, 0.05% (w/v) magnesium sulfate heptahydrate, and water was placed in 500-ml Erlenmeyer flasks in a volume of 100 ml each, autoclaved at 121° C. for 20 minutes to effect sterilization, cooled, inoculated with a stock culture of *Arthrobacter globiforis*, IAM 12103, and incubated at 27° C. for 48 hours under rotary shaking conditions of 230 rpm for use as a seed culture. About 20 L of a fresh preparation of the same nutrient culture medium as used in the above culture were placed in a 30-L fermentor, sterilized by heating, cooled to 27° C., inoculated with 1% (v/v) of the seed culture, and incubated for about 72 hours while stirring under aeration agitation conditions at 27° C. and a pH of 6.0-8.0. The resultant culture, having an activity of about 16.5 units/ml of α-isomaltodextranase as an isomaltose-releasing enzyme, was centrifuged at 10,000 rpm for 30 min to obtain about 18 L of a supernatant having an activity of about 16 units/ml of the enzyme and a total enzyme activity of about 288,000 units. The activity of isomaltodextranase was assayed as follows: Provide as a substrate solution a 1.25% (w/v) aqueous dextran solution containing 0.1M acetate buffer (pH 5.5), add one milliliter of an enzyme solution to the substrate solution, react the mixture solution at 40° C. for 20 min, collect one milliliter of the reaction mixture, added the collected reaction mixture to two milliliters of Somogyi reagent to suspend the enzymatic reaction, and quantify the reducing power of the formed isomaltose by the Somogyi-Nelson's method. One unit of isomaltodextranase activity was defined as the enzyme amount that exhibits a reducing power corresponding to that of one micromole of isomaltose per minute under the above enzymatic reaction conditions. About 18 L of the resulting supernatant was concentrated with a UF membrane into an about two liter solution which was then dialyzed against 80% saturated ammonium sulfate solution at 4° C. for 24 hours. The salted out precipitates were collected by centrifugation at 10,000 rpm for 30 min and dissolved in 5 mM phosphate buffer (pH 6.8), followed by dialyzing the resulting solution against a fresh preparation of the same phosphate buffer to obtain about 400 ml of a crude enzyme solution. The crude enzyme solution was subjected to ion-exchange chromatography using two liters of "SEPABEADS FP-DA13" gel. Isomaltodextranase was eluted in non-adsorbed fractions without adsorbing on the gel. The fractions with isomaltodextranase activity were collected, pooled and dialyzed against 80% saturated ammonium solution at 4° C. for 24 hours. The resulting precipitates were collected by centrifugation at 10,000 rpm for 30 min and dissolved in 5 mM phosphate buffer (pH 6.8), and the solution was dialyzed against a fresh preparation of the same phosphate buffer to obtain about 500 ml of a partially purified enzyme solution having an activity of 161,000 units of isomaltodextranase.

EXPERIMENT 16

Preparation of Isomaltose from α-isomaltosylglucosaccharide and Cyclotetrasaccharide To an aqueous solution having a final solid concentration of 0.2% (w/v) of panose, α-isomaltosylmaltose, α-isomaltosyltriose, α-isomaltosyltetraose, or cyclotetrasaccharide, were added 100 units/g solid of an isomaltodextranase specimen, obtained by the method in Experiment 15, except for using 100 or 3,000 units of the specimen for the aqueous solution of cyclotetrasaccharide, allowed to react at 40° C. and pH 5.5 for 24 hours, and kept at 100° C. for 20 min to suspend the enzymatic reactions. The saccharide composition for each reaction mixture was determined on HPLC. The conditions used in HPLC were: Column, "MCIGEL CK04SS" comercialized by Mitsubishi Chemical Industries, Ltd., Tokyo, Japan; 80° C., inner column temperature; 0.5 ml/min, a flow rate of water as an eluent; and detection, "RI-8012", a diffraction refractometer commercialized by Tosoh Corporation, Tokyo, Japan. The results are in Table 18.

TABLE 18

| Substrate | Amount of enzyme (unit) | Saccharide formed (peak area (%) on HPLC) | | | | |
|---|---|---|---|---|---|---|
| | | G1 | IM | G2 | G3 | G4 | A |
| IMG1 | 100 | 35 | 65 | 0 | 0 | 0 | 0 |
| IMG2 | 100 | 0 | 51 | 49 | 0 | 0 | 0 |
| IMG3 | 100 | 0 | 41 | 0 | 59 | 0 | 0 |
| IMG4 | 100 | 0 | 35 | 0 | 0 | 65 | 0 |
| Cyclotetrasaccharide | 100 | 0 | 22 | 0 | 0 | 0 | 78 |
| Cyclotetrasaccharide | 3,000 | 0 | 100 | 0 | 0 | 0 | 0 |

Note:
The symbols "IMG1", "IMG2", "IMG3" and "IMG4" mean panose, α-isomaltosylmaltose, α-isomaltosyltriose, and isomaltosyltetraose, respectively; the symbols "G1", "IM", "G2", "G3", and "G4" mean glucose, isomaltose, maltose, maltotriose, and maltotetraose, respectively; and the symbol "A" means an intermediate product formed during the formation of isomaltose from cyclotetrasaccharide.

As is evident from the results shown in Table 18, it was revealed that, when acts on α-isomaltosylglucosaccharides, isomaltodextranase forms only glucose and isomaltose from panose as a substrate; only isomaltose and maltose from α-isomaltosylmaltose as a substrate; only isomaltose and maltotriose from α-isomaltosyltriose as a substrate; and forms only isomaltose and maltotetraose from α-isomaltosyltetraose as a substrate. It was revealed that the enzyme forms only isomaltose from cyclotetrasaccharide as a substrate through product A as the intermediate.

Thereafter, product A as an intermediate formed from cyclotetrasaccharide as a substrate, was purified and isolated as follows: Using "YMC-PACK ODS-A R355-15S-15 12A", a separatory HPLC column commercialized by YMC Co., Ltd., Tokyo, Japan, the product A was purified and isolated, resulting in an isolation of product A, having a purity of at least 98.2% in a yield of about 7.2%, from the reaction products formed from the material cyclotetrasaccharide.

Figure 21:
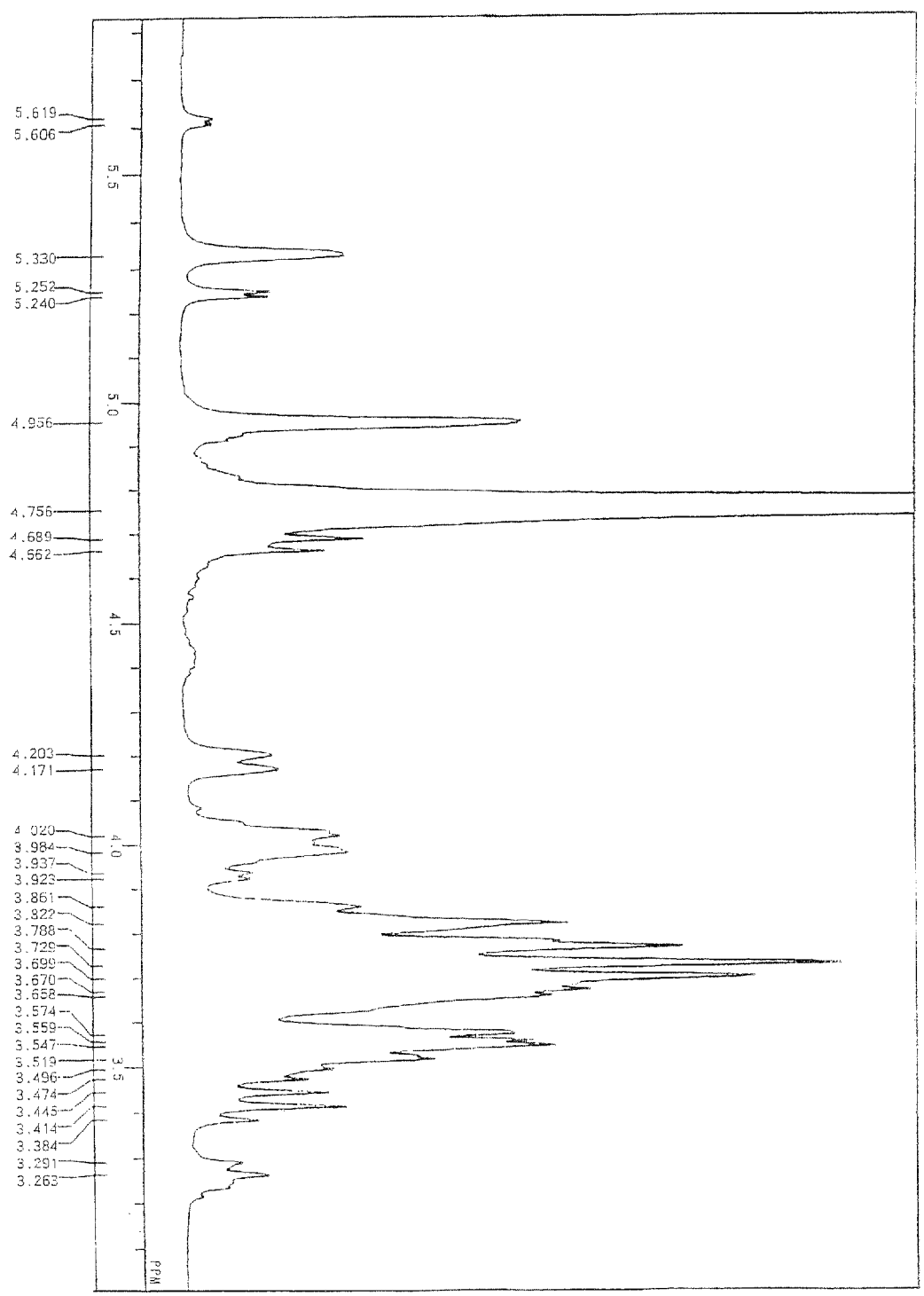
FIG. 21 is a nuclear resonance spectrum ($^1$H-NMR) of the product A.
Figure 22:
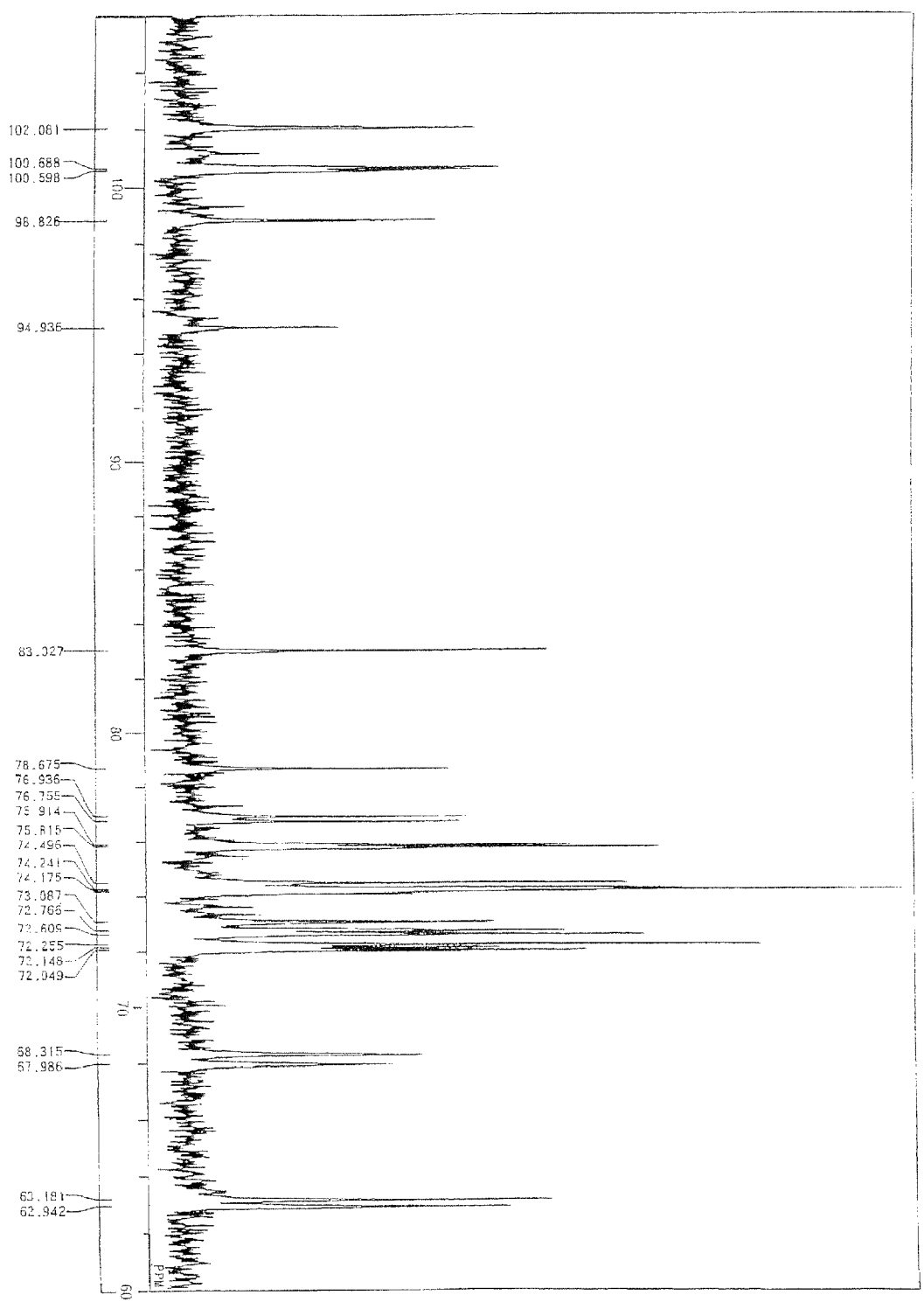
FIG. 22 is a nuclear resonance spectrum ($^{13}$C-NMR) of the product A.

Upon the product A, it was subjected to methyl analysis and NMR analysis in a usual manner. The results on the methyl analysis is in Table 19. For the result on the NMR analysis, the $^1$H-NMR spectrum is FIG. 21. The $^{13}$C-NMR spectrum for the product A is in FIG. 22, and the assignment thereof is tabulated in Table 20.

TABLE 19

| Analyzed methyl compound | Ratio |
|---|---|
| 2,3,4-trimethyl compound | 2.00 |
| 2,3,6-trimethyl compound | 0.92 |
| 2,3,4,6-tetramethyl compound | 0.88 |

TABLE 20

| Glucose number | Carbon Number | NMR Chemical shift (ppm) |
|---|---|---|
| a | 1a | 100.7 |
|   | 2a | 74.2 |
|   | 3a | 75.2 |
|   | 4a | 72.3 |
|   | 5a | 74.5 |
|   | 6a | 63.2 |
| b | 1b | 102.1 |
|   | 2b | 74.3 |
|   | 3b | 75.9 |
|   | 4b | 72.6 |
|   | 5b | 74.2 |
|   | 6b | 68.0 |
| c | 1c | 100.6 |
|   | 2c | 72.8 |
|   | 3c | 83.0 |
|   | 4c | 72.0 |
|   | 5c | 73.1 |
|   | 6c | 62.9 |
| e | 1e | 94.9 (α), 98.8 (β) |
|   | 2e | 74.1 (α), 76.6 (β) |
|   | 3e | 75.8 (α), 78.7 (β) |
|   | 4e | 72.1 (α), 72.1 (β) |
|   | 5e | 72.6 (α), 76.9 (β) |
|   | 6e | 68.3 (α), 68.3 (β) |

Based on these results, it was revealed that product A, as an intermediate, formed during the formation of isomaltose from cyclotetrasaccharide via the action of isomaltodextranase was a tetrasaccharide represented by Formula 3, α-D-glucosyl-(1→6)-α-D-glucosyl-(1→3)-α-D-glucosyl-(1→6)-α-D-glucose (designated as "ring-opened tetrasaccharide" hereinafter), obtained by hydrolyzing either of the α-1,3 linkages in cyclotetrasaccharide for ring opening.

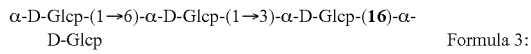

Formula 3:

Based on these results, the action of isomaltodextranase on α-isomaltosylglucosaccharide is judged as follows:

Isomaltodextranase acts on α-isomaltosyl-glucosaccharides having a 6-O-α-glucosyl residue as substrates to specifically hydrolyze the α-1,4 linkage between the isomaltosyl residue at the non-reducing end and the glucose residue (or a maltooligosaccharide residue) to form isomaltose and glucose (or a maltooligosaccharide). The enzyme also acts on cyclotetrasaccharide as a substrate and hydrolyzes its α-1,3 linkage, and further acts on a ring-opened tetrasaccharide and hydrolyzes its α-1,3 linkage to form isomaltose.

EXPERIMENT 17

Formation of Isomaltose from Substrates

Using different substrates, the isomaltose formation by the action of α-isomaltosylglucosaccharide-forming enzyme and isomaltodextranase was tested. Using calcium chloride and maltose, maltotriose, maltotetraose, maltopentaose, maltohexaose, maltoheptaose, amylose, or "PINE-DEX #100", a partial starch hydrolyzate commercialized by Matsutani Chemical Ind., Tokyo, Japan, aqueous solutions for saccharides each were prepared to give a final saccharide concentration of 5% and a final calcium chloride concentration of 1 mM. Then, to each solution were added 0.2 unit/g solids of the purified α-isomaltosylglucosaccharide-forming enzyme from Strain C11 obtained in Experiment 4-1 and 100 units/g solids of the isomaltodextranase obtained in Experiment 15, followed by reacting at 40° C. at pH 5.5. The reaction conditions were conducted in the following two reaction systems:

(1) After contacting α-isomaltosylglucosaccharide-forming enzyme with each saccharide for 65 hours, the enzyme was inactivated by heating, and then isomaltodextranase was further allowed to act on the saccharide for 65 hours and inactivated by heating.

(2) After contacting α-isomaltosylglucosaccharide-forming enzyme in combination with isomaltodextranase with each saccharide for 65 hours, the enzymes were inactivated by heating.

After the above enzymatic reactions, the formation yield of isomaltose in the resulting reaction mixtures received with heat treatment was quantified on HPLC. The results are in Table 21.

TABLE 21

| | Formation yield of isomaltose (%) | |
|---|---|---|
| Substrate | A | B |
| Maltose | 6.6 | 7.0 |
| Maltotriose | 15.7 | 18.7 |
| Maltotetraose | 15.8 | 45.4 |
| Maltopentaose | 15.3 | 55.0 |
| Maltohexaose | 10.1 | 58.1 |
| Maltoheptaose | 8.5 | 63.6 |
| Amylose | 4.0 | 64.9 |
| Partial starch hydrolyzate | 3.8 | 62.7 |

Note:
The symbol "A" means that after contacting α-isomaltosylglucosaccharide-forming enzyme with each saccharide, isomaltodextranase was further allowed to act on the resulting mixture. The symbol "B" means that α-isomaltosylglucosaccharide-forming enzyme and isomaltodextranase were used in combination.

As evident from the results in Table 21, from every saccharide tested, isomaltose was formed via the action of α-isomaltosylglucosaccharide-forming enzyme and isomaltodextranase. It was revealed that, in the case of sequentially contacting α-isomaltosylglucosaccharide-forming enzyme and isomaltodextranase with each saccharide, the formation yield of isomaltose was relatively low as about 15%, while in the case of contacting these enzymes in a combinative manner with any of the saccharides, the formation yield of isomaltose was improved, particularly, it was improved up to 60% or higher when acted on maltoheptaose, amylose, and partial starch hydrolyzate. The mechanism of forming isomaltose by the combination use of α-isomaltosylglucosaccharide-forming enzyme and isomaltodextranase would be as follows:

(1) α-Isomaltosylglucosaccharide-forming enzyme acts on a glucose residue at the non-reducing end of an α-1,4 glucan chain such as amylose and partial starch hydrolyzate and transfers the glucose residue to the C-6 hydroxyl group of another glucose residue at the non-reducing end of another α-1,4 glucan chain to form a α-1,4 gluacan chain having an α-isomaltosyl residue at the non-reducing end;

(2) Isomaltodextranase acts on an α-1,4 glucan chain having an isomaltosyl residue at the non-reducing end and hydrolyzes the α-1,4 linkage between the isomaltosyl residue and the α-1,4 glucan chain to form a glucan chain, free of the isomaltose, with a lowered glucose polymerization degree by two; and (3) The released α-1,4 glucan chain is again sequentially received the steps (1) and (2) to newly form isomaltose.

It would be estimated that, through the combination use of α-isomaltosylglucosaccharide-forming enzyme and isomaltodextranase, the formation yield of isomaltose would be increased by the repeated action of the enzymes on α-1,4 glucan chains as described above.

EXPERIMENT 18

Effect of the Addition of Isoamylase

Aqueous solutions of "PINE-DEX #100", a partial starch hydrolyzate, having a final concentration of 5% and 1 mM calcium chloride, were prepared, admixed with 0.2 unit/g starch of the purified α-isomaltosylglucosaccharide-forming enzyme from Strain C11 in Experiment 4-1, 100 units/g starch of the isomaltodextranase in Experiment 15, and 0-250 units/g starch of an isoamylase specimen from a microorganism of the species Pseudomonas amyloderamosa commercialized by Hayashibara Biochemical Laboratories, Inc., Okayama, Japan, incubated at 40° C. and pH 5.5 for 65 hours, and then heated at 100° C. for 15 min to inactivate the enzymes used. The formed isomaltose was quantified on HPLC. The results are in Table 22.

TABLE 22

| Amount of isoamylase added (unit) | Formation yield of isomaltose (%) |
| --- | --- |
| 0 | 62.7 |
| 50 | 65.1 |
| 250 | 71.1 |

As is evident from the results shown in Table 22, it was revealed that the addition of isoamylase increases the formation yield of isomaltose formed.

EXPERIMENT 19

Influence of the Concentration of Partial Starch Hydrolyzate

Eight types of aqueous solutions with different concentrations of "PINE-DEX #100", a partial starch hydrolyzate with a DE of about 2-5, having final concentrations of 1-40% and 1 mM calcium chloride, were prepared. To each aqueous solution 0.2 unit/g starch of the purified α-isomaltosylglucosaccharide-forming enzyme from Strain C11 in Experiment 4-1, 100 units/g starch of the isomaltodextranase in Experiment 15, and 250 units/g starch of an isoamylase specimen from a microorganism of the species Pseudomonas amyloderamosa commercialized by Hayashibara Biochemical Laboratories, Inc., Okayama, Japan, incubated at 40° C. and pH 5.5 for 65 hours, and then heated at 100° C. for 15 min to inactivate the enzymes used. The formed isomaltose was quantified on HPLC. The results are in Table 23.

TABLE 23

| Concentration of PINE-DEX (%) | Formation yield of isomaltose (%) |
| --- | --- |
| 1 | 73.0 |
| 2.5 | 72.8 |
| 5 | 71.1 |
| 10 | 67.0 |
| 15 | 63.7 |
| 20 | 60.7 |
| 30 | 55.4 |
| 40 | 50.7 |

As is evident from the results in Table 23, it was revealed that the formation of yield of isomaltose was about 73% at a concentration of one percent of partial starch hydrolyzate, while it was about 51% at a relatively high concentration of 40%. Thus, the formation of yield of isomaltose changes depends on the concentration of partial starch hydrolyzate as a substrate.

EXPERIMENT 20

Influence of the Liquefaction Degree of Starch

Corn starch was prepared into a 15% starch suspension which was then mixed with 0.1% calcium carbonate, adjusted to pH 6.0, admixed with 0.2-2.0% per gram starch of "TERMAMYL 60L", an α-amylase specimen commercialized by Novo Indutri A/S, Copenhagen, Denmark, allowed to react at 95° C. for 10 min, and autoclaved at 120° C. Thereafter, the reaction mixture was promptly cooled to about 40° C. to obtain a liquefied solution with a DE of 3.2-20.5 which was then adjusted to pH 5.5, admixed with 0.2 unit/g starch of the purified α-isomaltosylglucosaccharide-forming enzyme from Strain C11 in Experiment 4-1, 100 units/g starch of the isomaltodextranase in Experiment 15, and 250 units/g starch of an isoamylase specimen from a microorganism of the species Pseudomonas amyloderamosa commercialized by Hayashibara Biochemical Laboratories, Inc., Okayama, Japan, incubated at 40° C. for 65 hours, and then heated at 100° C. for 15 min to inactivate the enzymes used. The formed isomaltose was quantified on HPLC. The results are in Table 24.

TABLE 24

| Amount of α-amylase used (% (w/w) per gram starch) | DE | Formation yield of isomaltose (%) |
| --- | --- | --- |
| 0.2 | 3.2 | 71.5 |
| 0.4 | 4.8 | 71.0 |
| 0.6 | 7.8 | 66.2 |
| 1.0 | 12.5 | 59.8 |
| 1.5 | 17.3 | 53.2 |
| 2.0 | 20.5 | 47.9 |

As is evident from the results shown in Table 24, it was revealed that the liquefaction degree of starch influences the formation yield of isomaltose using α-isomaltosylglucosaccharide-forming enzyme and isomaltodextranase; the lower the liquefaction degree or the lower the DE, the higher the formation yield of isomaltose becomes, in reverse, the higher the liquefaction degree or the higher the DE, the lower the formation yield of isomaltose becomes; it was revealed that the liquefaction degree should preferably be a DE not higher than 20, preferably, DE not higher than 12, more preferably, DE not higher than five.

EXPERIMENT 23

Effect of the Addition of Cyclodextrin Glucanotransferase and Glucoamylase

Aqueous solutions of "PINE-DEX #100", a partial starch hydrolyzate, having a final concentration of 20% and 1 mM calcium chloride, were prepared and admixed with 0.2 unit/g starch of the purified α-isomaltosylglucosaccharide-forming enzyme from Strain C11 in Experiment 4-1, 100 units/g starch of the isomaltodextranase in Experiment 15, 250 units/g starch of an isoamylase specimen from a microorganism of the species *Pseudomonas amyloderamosa* commercialized by Hayashibara Biochemical Laboratories, Inc., Okayama, Japan, and 0-0.5 unit/g starch of a CGTase specimen from a microorganism of the species *Bacillus stearothermophilus*, commercialized by Hayashibara Biochemical Laboratories, Inc., Okayama, Japan, and incubated with these enzymes at 40° C. and pH 5.5 for 65 hours. Thereafter, each reaction mixture was heated at 100° C. for 15 min to inactivate the enzymes, admixed with 20 units/g starch of "XL-4", a glucoamylase commercialized by Nagase Biochemicals, Ltd., Kyoto, Japan, incubated at 50° C. for 24 hours, and heated at 100° C. for 20 min to inactivate the remaining enzyme. The formed isomaltose was quantified on HPLC. The results are in Table 25.

TABLE 25

| Amount of CGTase added (unit per gram starch) | Formation yield of isomaltose (%) |
| --- | --- |
| 0 | 60.7 |
| 0.1 | 62.9 |
| 0.25 | 65.0 |
| 0.5 | 66.4 |

As evident from the results in Table 25, it was revealed that the addition of CGTase to the enzymatic system of α-isomaltosylglucosaccharide-forming enzyme and isomaltodextranase increases the formation yield of isomaltose. The object of using the glucoamylase was to increase the formation of isomaltose by releasing D-glucose residue(s) from a saccharide composed of isomaltose and at least one D-glucose residue.

With reference to the following Examples A and B, the process for producing isomaltose or high isomaltose content products according to the present invention and uses thereof are disclosed in detail:

EXAMPLE A-1

About 100 L of an aqueous solution of phytoglycogen from corn, commercialized by Q.P. Corporation, Tokyo, Japan, were adjusted to give a concentration of 4% (w/v), pH 6.0, and a temperature of 30° C., admixed with one unit/g starch of a purified α-isomaltosylglucosaccharide-forming enzyme from Strain C11 obtained by the method in Experiment 4-1, and 10 units/g starch of an α-isomaltosyl-transferring enzyme from Strain C11 obtained by the method in Experiment 4-4, allowed to react for 48 hours, and heated at 100° C. for 10 min to inactivate the remaining enzymes. The resulting mixture was sampled and quantified the formation yield of cyclotetrasaccharide on HPLC to be about 84% with respect to the saccharide composition, wherein HPLC was carried out under the conditions of: Column, "SHODEX KS-801 COLUMN" comercialized by Showa Denko K.K., Tokyo, Japan; 60° C., an inner column temperature; 0.5 ml/min, a flow rate of water as an eluent; and detection by "RI-8012", a diffraction refractometer commercialized by Tosoh Corporation, Tokyo, Japan. After adjusted to pH 5.0 and 45° C., the resulting reaction mixture was admixed with 1,500 units/g starch "TRANSGLUCOSIDASE L AMANO™", an α-glucosidase commercialized by Amano Pharmaceutical Co., Ltd., Aichi, Japan, and 75 units/g starch of "XL-4", a glucoamylase specimen commercialized by Nagase Biochemicals, Ltd., Kyoto, Japan, to hydrolyze the remaining reducing-oligosaccharides. Then, the resulting mixture was adjusted to give a pH 5.8 by the addition of sodium hydroxide, kept at 90° C. for one hour to inactivate the remaining enzymes, and filtered to remove insoluble substances. The filtrate was concentrated using "HOLLOSEP® HR5155PI", a reverse osmosis membrane commercialized by Toyobo Co., Ltd., Tokyo, Japan, up to give a concentration of about 16% (w/v). Then, the concentrate was in a usual manner decolored, desalted, filtered, and concentrated into about 6.2 kg of a saccharide solution having about 3,700 g of solid contents. The saccharide solution was fed to a column packed with about 225 L of "AMBERLITE CR-1310 ($Na^+$-form)", a strong-acid cation-exchanger commercialized by Japan Organo Co., Ltd., Tokyo, Japan, and chromatographed at a column temperature of 60° C. and a flow rate of about 45 L/h. While monitoring the saccharide composition of the eluate by the above HPLC, fractions of cyclotetrasaccharide with a purity of 98% or higher were collected and pooled, and then in a usual manner, desalted, decolored, filtered, and concentrated to obtain about 7.5 kg saccharide solution with a solid content of about 2,500 g. The HPLC revealed that the saccharide solution had a purity of about 99.5% of cyclotetrasaccharide. The obtained saccharide solution containing cyclotetrasaccharide was concentrated by an evaporator to give a concentration of about 50%, and about 5 kg of the concentrate was placed in a cylindrical plastic container and cooled from 65° C. to 20° C. over about 20 hours under gentle stirring conditions to crystallize cyclotetrasaccharide. Thereafter, the resulting massecuite was centrifuged to separate 1,360 g of cyclotetrasaccharide crystal on a wet weight, which was then dried at 60° C. for three hours to obtain 1,170 g of a powdery cyclotetrasaccharide crystal. The powdery crystal was analyzed for saccharide composition on HPLC to reveal that it had a quite high purity of at least 99.9% of cyclotetrasaccharide.

The powdery cyclotetrasaccharide crystal thus obtained was dissolved in deionized water to give a concentration of one percent, pH 5.5, and 50° C., followed by admixing with 500 units/g solids of an isomaltodextranase specimen obtained by the method in Experiment 15, and incubating the mixture at pH 5.5 and 50° C. for 70 hours. After completion of the enzymatic reaction, the reaction mixture was heated to 95° C. and kept at the temperature for 10 min, cooled, and filtered. The resulting filtrate was in a usual manner decolored with an activated charcoal, desalted and purified using ion-exchange resins in H— and OH-forms, and further concentrated to give a concentration of 75%. Thus, a high isomaltose content syrup was obtained in a yield of about 95%, d.s.b.

The product contained 96.1% isomaltose, 2.8% ring-opened tetrasaccharide, and 1.1% other saccharides, d.s.b. Since the product substantially free of crystallization has a satisfactory humectancy, low-sweetness, osmosis controllability, filler-imparting ability, gloss-imparting ability, viscosity, ability of preventing crystallization of other saccharides, insubstantial fermentability, ability of preventing retrogradation of starches, etc., it can be arbitrarily used in foods, beverages, health foods, feeds, pet foods, cosmetics, pharmaceuticals, tobaccos, and cigarettes.

EXAMPLE A-2

A high isomaltose content syrup, obtained by the method in Example A-1, was subjected to column chromatography using "AMBERLITE CR-1310 ($Na^+$-form)", a strong-acid cation exchanger commercialized by Japan Organo Co., Ltd., Tokyo, Japan. The resin was packed into 10 jacketed stainless steel columns having a diameter of 12.5 cm, which were then cascaded in series to give a total gel bed depth of 16 m. Under the conditions of keeping the inner column temperature at 40° C., the above saccharide syrup was fed to the columns in a volume of 1.5% (v/v) and fractionated by feeding to the columns hot water heated to 40° C. at an SV (space velocity) of 0.2 to obtain high isomaltose content fractions while monitoring the saccharide composition of eluate on HPLC. Then, the fractions were pooled and purified to obtain a high isomaltose content solution in a yield of about 80%, d.s.b. The solution was in a usual manner decolored, desalted, and concentrated into an about 75%, d.s.b., of high isomaltose content syrup.

The product contained a high purity isomaltose with a purity of at least 99.9%, d.s.b. Since the product substantially free of crystallization has a satisfactory humectancy, low-sweetness, osmosis controllability, filler-imparting ability, gloss-imparting ability, viscosity, ability of preventing crystallization of other saccharides, insubstantial fermentability, ability of preventing retrogradation of starches, etc., it can be arbitrarily used in foods, beverages, health foods, feeds, pet foods, cosmetics, pharmaceuticals, tobaccos, and cigarettes.

EXAMPLE A-3

A tapioca starch was prepared into an about 20% starch suspension, admixed with calcium carbonate to give a concentration of 0.1%, adjusted to pH 6.5, further admixed with 0.3% per gram starch, d.s.b., of "TERMAMYL 60L", an α-amylase commercialized by Novo Industri A/S, Copenhagen, Denmark, and then heated at 95° C. for about 15 min. Thereafter, the mixture was autoclaved at 120° C. for 20 min and then promptly cooled to about 40° C. to obtain a liquefied solution with a DE of about four. To the liquefied solution was added 0.2 unit/g starch of an α-isomaltosylglucosaccharide-forming enzyme obtained by the method in Experiment 2-1, 100 units/g starch of an isomaltodextranase obtained by the method in Experiment 15, 250 units/g starch of an isomaltodextranase specimen commercialized by Hayashibara Biochemical Laboratories, Inc., Okayama, Japan, and 0.5 unit/g starch of a CGTase specimen commercialized by Hayashibara Biochemical Laboratories, Inc., Okayama, Japan, and then enzymatically reacted at pH 5.5 and 40° C. for 64 hours. The reaction mixture was kept at 95° C. for 30 min, adjusted to 50° C., 10 units/g solids of "GLUCOZYME", a glucoamylase preparation commercialized by Nagase Biochemicals, Ltd., Kyoto, Japan, and then enzymatically reacted for 24 hours. The reaction mixture thus obtained was heated to and kept at 95° C. for 30 min, and then cooled and filtered. The filtrate was in a conventional manner decolored with an activated charcoal, desalted and purified with ion exchangers in H— and OH-forms, and then concentrated, dried, pulverized, and granulated into isomaltose granules in a yield of about 95%, d.s.b.

The product contains, on a dry solid basis, 11.0% glucose, 66.5% isomaltose, 2.4% other disaccharides, and 20.1% trisaccharides or higher. Since the product has a satisfactory humectancy, low-sweetness, osmosis controllability, filler-imparting ability, gloss-imparting ability, viscosity, ability of preventing crystallization of other saccharides, insubstantial fermentability, ability of preventing retrogradation of starches, etc., it can be arbitrarily used in foods, beverages, health foods, feeds, pet foods, cosmetics, pharmaceuticals, tobaccos, and cigarettes.

EXAMPLE A-4

*Bacillus globisporus* C9 strain, FERM BP-7143, was cultured by a fermentor for 48 hours in accordance with the method in Experiment 1. After completion of the culture, the resulting culture was filtered with an SF membrane to remove cells and to collect about 18 L of a culture supernatant. Then the culture supernatant was concentrated with a UF membrane to collect about one liter of a concentrated enzyme solution containing 8.8 units/ml of an α-isomaltosylglucosaccharide-forming enzyme and 26.7 units/ml of an α-isomaltosyl-transferring enzyme. A potato starch was prepared into an about 27% starch suspension which was then admixed with 0.1% calcium carbonate, adjusted to pH 6.5, admixed with 0.3% per gram starch, d.s.b., of "TERMAMYL 60L", an α-amylase commercialized by Novo Industri A/S, Copenhagen, Denmark, and then sequentially heated at 95° C. for 15 min, autoclaved at 120° C. for 20 min, and promptly cooled to about 40° C. to obtain a liquefied solution with a DE of about four. To the liquefied solution were added 0.25 ml per gram of starch of the above concentrated enzyme solution containing the α-isomaltosylglucosaccharide-forming enzyme and the α-isomaltosyl-transferring enzyme, 100 units/g starch of an isomaltodextranase obtained by the method in Experiment 15, 250 units/g starch of an isoamylase specimen commercialized by Hayashibara Biochemical Laboratories, Inc., Okayama, Japan, and 0.5 unit/g starch of a CGTase specimen commercialized by Hayashibara Biochemical Laboratories, Inc., Okayama, Japan, and then the resulting mixture was subjected to enzymatic reaction at pH 5.5 and 40° C. for 70 hours. The reaction mixture was heated to and kept at 95° C. for 10 min, adjusted to 50° C., admixed with 20 units/g starch of "GLUCOZYME", a glucoamylase preparation commercialized by Nagase Biochemicals, Ltd., Kyoto, Japan, and then enzymatically reacted for 24 hours. The reaction mixture thus obtained was heated to and kept at 95° C. for 30 min, and then cooled and filtered. The filtrate was in a conventional manner decolored with an activated charcoal, desalted and purified with ion exchangers in H— and OH-forms and concentrated to obtain a 75% high isomaltose content syrup in a yield of about 95%, d.s.b.

The product contains, on a dry solid basis, 32.6% glucose, 59.4% isomaltose, 1.2% other disaccharides, and 6.8% trisaccharides or higher. Since the product substantially free of crystallization has a satisfactory humectancy, low-sweetness, osmosis controllability, filler-imparting ability, gloss-imparting ability, viscosity, ability of preventing crystallization of other saccharides, insubstantial fermentability, ability of preventing retrogradation of starches, etc., it can be arbitrarily used in foods, beverages, health foods, feeds, pet foods, cosmetics, pharmaceuticals, tobaccos, and cigarettes.

EXAMPLE A-5

To increase the isomaltose content in the high isomaltose content syrup in Example A-4 as a material saccharide solution, in accordance with the method in Example A-2, the syrup was subjected to column chromatography using a strong-acid cation exchange resin, followed by collecting the resulting high isomaltose content fractions which were then pooled and concentrated to obtain a high isomaltose content syrup in a yield of about 60%, d.s.b.

The product contains, on a dry solid basis, 4.8% glucose, 85.3% isomaltose, 3.9% other disaccharides, and 6.0% trisaccharides or higher. Since the product substantially free of crystallization has a satisfactory humectancy, low-sweetness, osmosis controllability, filler-imparting ability, gloss-imparting ability, viscosity, ability of preventing crystallization of other saccharides, insubstantial fermentability, ability of preventing retrogradation of starches, etc., it can be arbitrarily used in foods, beverages, health foods, feeds, pet foods, cosmetics, pharmaceuticals, tobaccos, and cigarettes.

EXAMPLE B-1

Sweetener

To 0.8 part by weight of a high isomaltose content powder, obtained by the method in Example A-1, were homogeneously added 0.2 part by weight of "TREHA®", a crystalline trehalose hydrate commercialized by Hayashibara Shoji Inc., Okayama, Japan, 0.01 part by weight of "αG SWEET™" (α-glycosyl stevioside commercialized by Toyo Sugar Refining Co., Tokyo, Japan), and 0.01 part by weight of "ASPARTAME" (L-aspartyl-L-phenylalanine methyl ester). The resulting mixture was fed to a granulator to obtain a granular sweetener. The product has a satisfactory sweetness and about 2-fold higher sweetening power than sucrose. The product is a low-sweetener composition containing isomaltose which is substantially free of crystallization and has satisfactory humectancy and low sweetness. The product has a satisfactory stability with less tendency to cause quality deterioration even when stored at ambient temperature.

EXAMPLE B-2

Hard Candy

One hundred parts by weight of a 55% sucrose solution was admixed while heating with 50 parts by weight of a high isomaltose content syrup obtained by the method in Example A-2.

The mixture was then concentrated by heating under reduced pressure to give a moisture content of less than 2%, and the concentrate was mixed with 0.6 part by weight of citric acid and adequate amounts of a lemon flavor and a color, followed by forming the resultant mixture into the desired product in the usual manner. The product is a stable, high quality hard candy which has a satisfactory mouth feel, taste, and flavor, scarcely adsorbs moisture, and does not cause crystallization of sucrose.

EXAMPLE B-3

Chewing Gum

Three parts by weight of a gum base were melted by heating to an extent to be softened and then admixed with two parts by weight of anhydrous crystalline maltitol anhydride, two parts by weight of xylitol, two parts by weight of a high isomaltose content syrup obtained by the method in Example A-5, and one part by weight of trehalose, and further mixed with adequate amounts of a flavor and a color. The mixture was kneaded by a roll in the usual manner and then was shaped and packed to obtain the desired product. The product was a relatively low cariogenic and caloric chewing gum having a satisfactory texture, taste, and flavor.

EXAMPLE B-4

Powdery Peptide

One part by weight of 40% of "HINUTE S", a peptide solution of edible soy beans commercialized by Fuji Oil Co., Ltd., Tokyo, Japan, was mixed with two parts by weight of a high isomaltose content syrup obtained by the method in Example A-4, and the resultant mixture was placed in a plastic vat, dried in vacuo at 50° C., and pulverized to obtain a powdery peptide. The product, having a satisfactory flavor and taste, can be arbitrarily used as a material for low-calorie confectioneries such as premixes, sherbets and ice creams, as well as a material for controlling intestinal conditions, health food, and substantially non-digestible edible fibers used for fluid diets for oral administration and intubation feeding.

EXAMPLE B-5

Bath Salt

One part by weight of a peel juice of "yuzu" (a Chinese lemon) was mixed with 10 parts by weight of a high isomaltose content syrup obtained by the method in Example A-3, and one part by weight of cyclotetrasaccharide, and the mixture was pulverized into an isomaltose powder containing peel juice of yuzu.

A bath salt was obtained by mixing five parts by weight of the above powder with 90 parts by weight of grilled salt, two parts by weight of crystalline trehalose hydrate, one part by weight of silicic anhydride, and 0.5 part by weight of "αG HESPERIDIN", α-glucosyl hesperidin commercialized by Hayashibara Shoji, Inc., Okayama, Japan.

The product is a high quality bath salt enriched with yuzu flavor and used by diluting in hot bath water by 100-10,000 folds, and it moisturizes and smooths the skin and does not make one feel cold after taking a bath therewith.

EXAMPLE B-6

Cosmetic Cream

Two parts by weight of polyoxyethylene glycol monostearate, five parts by weight of glyceryl monostearate, self-emulsifying, two parts by weight of a high isomaltose content syrup obtained by the method in Example A-2, one part by weight of "αG RUTIN", α-glucosyl rutin commercialized by Hayashibara Shoji, Inc., Okayama, Japan, one part by weight of liquid petrolatum, 10 parts by weight of glyceryl tri-2-ethylhexanoate, and an adequate amount of an antiseptic were dissolved by heating in a usual manner. The resulting solution was admixed with two parts by weight of L-lactic acid, five parts by weight of 1,3-butylene glycol, and 66 parts by weight of refined water, followed by emulsifying the mixture with a homogenizer and further admixing by stirring with an adequate amount of a flavor stirring to obtain a cosmetic cream. The product has an antioxidant activity and a relatively high stability, and these render it advantageously useful as a high quality sunscreen, skin-refining agent, and skin-whitening agent.

EXAMPLE B-7

Toothpaste

A toothpaste was obtained by mixing 45 parts by weight of calcium secondary phosphate, 1.5 parts by weight of sodium lauryl sulfate, 25 parts by weight of glycerine, 0.5 part by weight of polyoxyethylene sorbitan laurate, 15 parts by weight of a high isomaltose content syrup obtained by the method in Example A-5, 0.02 part by weight of saccharine, 0.05 part by weight of an antiseptic, and 13 parts by weight of water. The product has an improved after taste and a satisfactory feeling after use without deteriorating the washing power of the surfactant.

EXAMPLE B-8

Solid Preparation for Fluid Diet

One hundred parts by weight of a high isomaltose content syrup obtained by the method in Example A-1, 200 parts by weight of crystalline trehalose hydrate, 200 parts by weight of high maltotetraose content powder, 270 parts by weight of an egg yolk powder, 209 parts by weight of a skim milk powder, 4.4 parts by weight of sodium chloride, 1.8 parts by weight of potassium chloride, four parts by weight of magnesium sulfate, 0.01 part by weight of thiamine, 0.1 part by weight of sodium L-ascorbate, 0.6 part by weight of vitamin E acetate, and 0.04 part by weight of nicotinamide were mixed. Twenty-five grams aliquots of the resulting composition were injected into moisture-proof laminated small bags which were then heat sealed to obtain the desired product.

The product is a liquid diet that has a satisfactory intestinal-controlling action. One bag of the product is dissolved in about 150-300 ml of water into a; liquid diet and arbitrarily used by administering orally or intubationally into nasal cavity, stomach, intestines, etc., to supplement energy to living bodies.

EXAMPLE B-9

Tablet

Fifty parts by weight of aspirin were sufficiently admixed with 14 parts by weight of a high isomaltose content syrup obtained by the method in Example A-2, and four parts by weight of corn starch. The resulting mixture was tabletted by a tabletting machine in the usual manner to obtain tablets, 680 mg each, 5.25 mm in thickness.

The tablets, processed using the filler-imparting ability of isomaltose, have substantially no hygroscopicity, a sufficient physical strength and a quite satisfactory degradability in water.

EXAMPLE B-10

Sugar Coated Tablet

A crude tablet as a core, 150 mg weight, was sugar coated with a first solution consisting of 40 parts by weight of a high isomaltose content syrup obtained by the method in Example A-1, two parts by weight of pullulan having an average molecular weight of 200,000, 30 parts by weight of water, 25 parts by weight of talc, and three parts by weight of titanium oxide until the total weight reached about 230 mg. The resultant was then sugar coated with a second solution consisting of 65 parts by weight of crystalline cyclotetrasaccharide, one part by weight of pullulan, and 34 parts by weight of water, and glossed with a liquid wax to obtain a sugar coated tablet having a satisfactory gloss and appearance. The product has a relatively high shock tolerance and retains its high quality for a relatively-long period of time.

EXAMPLE B-11

Ointment for Treating Trauma

To 100 parts by weight of a high isomaltose content syrup obtained by the method in Example A-5 and 300 parts by weight of maltose was added 50 parts by weight of methanol dissolving three parts by weight of iodine. The resulting mixture was admixed with 200 parts by weight of a 10% (w/v) aqueous pullulan solution to obtain the captioned product with an adequate extensibility and adhesiveness. The product is a high-valued ointment in which the dispersion of iodine and methanol is well inhibited by isomaltose and which is relatively low in change during storage.

Because the product exerts a sterilizing action by iodine and acts, based on maltose, as an energy-supplementing agent to living cells, it shortens the curing term and well cures the affected parts and surfaces.

INDUSTRIAL APPLICABILITY

As described above, the present invention relates to a novel process for producing isomaltose and uses thereof, more particularly, to a process for producing isomaltose characterized in that it comprises the steps of allowing α-isomaltosylglucosaccharide-forming enzyme, in the presence or the absence of α-isomaltosyl-transferring enzyme, to act on saccharides having both a glucose polymerization degree of at least two and α-1,4 glucosidic linkage as a linkage at the non-reducing end to form α-isomaltosylglucosaccharides, which have a glucose polymerization degree of at least three, α-1,6 glucosidic linkage as a linkage at the non-reducing end, and α-1,4 glucosidic linkage as a linkage other than the non-reducing end, and/or to form cyclo{→6)-α-D-glucopyranosyl-(1→3)-α-D-glucopyranosyl-(1→6)-α-D-glucopyranosyl-(1→3)-α-D-glucopyranosyl-(1→}; allowing isomaltose-releasing enzyme to act on the formed saccharides to release isomaltose; and collecting the released isomaltose; and relates to uses thereof. The isomaltose and high isomaltose content products of the present invention do not substantially crystallize and have useful properties of humectancy, low sweetness, osmosis-controlling ability, filler-imparting ability, gloss-imparting ability, viscosity, crystallization-preventing ability for saccharides, insubstantial fermentability, retrogradation-preventing ability for gelatinized starches, etc. Thus, the isomaltose and high isomaltose content products can be arbitrarily used in foods, beverages, health foods, feeds, pet foods, cosmetics, pharmaceuticals, tobaccos, and cigarettes.

The present invention having these outstanding effects and functions is a significant invention that will greatly contribute to this art.

The invention claimed is:

1. A process for producing isomaltose, comprising the steps of:
   (a) allowing α-isomaltosylglucosaccharide-forming enzyme to act on a starting saccharide selected from the group consisting of maltooligosaccharides, maltodextrins, amylodextrins, amyloses, amylopectins, soluble starches, liquefied starches, and glycogens to form α-isomaltosylglucosaccharide having a glucose polymerization degree of at least three, an α-1,6 glucosidic linkage as a linkage at the non-reducing end, and α-1,4 glucosidic linkages at all positions except the linkage at the non-reducing end; said α-isomaltosylglucosaccharide-forming enzyme forms said α-isomaltosylglucosaccharide from said starting saccharide by catalyzing an α-glucosyl-transferring reaction without substantially hydrolyzing isomaltose, and said α-isomaltosylglucosaccharide forming enzyme is obtained from a microorganism of genus *Bacillus* or *Arthrobacter*;
   (b) allowing isomaltodextranase to act on the formed α-isomaltosylglucosaccharide to release isomaltose; and
   (c) collecting the released isomaltose wherein said α-isomaltosylglucosaccharide forming enzyme has the following physicochemical properties:
   (1) Molecular weight
      Having a molecular weight of about 117,000 to about 160,000 daltons when determined on SDS-PAGE;

(2) Isoelectric point (pI)
  Having an isoelectric point of 4.7 to about 5.7 when determined on isoelectrophoresis using ampholine;
(3) Optimum temperature
  Having a optimum temperature of about 40° C. to bout 45° C. when incubated at a pH of 6.0 for 60 min, or an optimum temperature of about 45° C. to about 50° C. when incubated in the presence of 1 mM $Ca^{2+}$;
(4) Optimum pH
  Having an optimum pH of about 6.0 to about 6.5 when incubated at 35° C. for 60 min;
(5) Thermal stability
  Stable up to a temperature of about 35° C. to 40° C. when incubated at pH 6.0 for 60 min, or a temperature of about 40° C. to about 45° C. when incubated in the presence of 1 mM $Ca^{2+}$; and
(6) pH stability
  Stable at a pH of about 4.5 to about 10.0 when incubated at 4° C. for 24 hours.

2. The process of claim 1, wherein in the step (a), one or more enzymes selected from the group consisting of α-isomaltosyl-transferring enzyme, cyclomaltodextrin glucanotransferase and starch debranching enzyme are allowed to act on the starting saccharide simultaneously; said α-isomaltosyl-transferring enzyme forms cyclotetrasaccharide having a structure of cyclo{→6)-α-D-glucopyranosyl-(1→3)-α-D-glucopyranosyl-(1→6)-α-D-glucopyranosyl-(1→3)-α-D-glucopyranosyl-(1→} through α-isomaltosyl transfer from said α-isomaltosylglucosaccharide; and said α-isomaltosyl-transferring enzyme is obtained from a microorganism of genus *Bacillus* or *Arthrobacter*, and has the following physicochemical properties:

(1) Molecular weight
  Having a molecular weight of about 82,000 to about 132,000 daltons when determined on SDS-PAGE:
(2) Isoelectric point (pI)
  Having an isoelectric point of about 5.0 to about 6.1 when determined on isoelectrophoresis using ampholine;
(3) Optimum temperature
  Having an optimum temperature of about 45° C. to about 50° C. when incubated at a pH of 6.0 for 30 min;
(4) Optimum pH
  Having an optimum pH of about 5.5 to about 6.0 when incubated at 35° C. for 30 min;
(5) Thermal stability
  Stable up to a temperature of about 40° C. when incubated at a pH of 6.0 or 60 min; and
(6) pH stability
  Stable at a pH of about 4.0 to about 9.0 when incubated at 4° C. for 24 hours.

3. The process of claim 1, wherein after the step (b), glucoamylase is allowed to act on the resulting mixture.

4. The process of claim 1, wherein in the step (c), the released isomaltose is collected on a column chromatograph using an alkaline metal and/or alkaline earth metal strong-acid cation exchange resin.

5. The process of claim 1, wherein the collected isomaltose is a high isomaltose content syrup having an isomaltose content of at least 40% (w/w), on a dry solid basis.

6. The process according to claim 1 wherein the α-isomaltosylglucosaccharide-forming enzyme is encoded by SEQ ID NO:1.

7. The process according to claim 2 wherein α-isomaltosyl-transferring enzyme is encoded by SEQ ID NO:2.

* * * * *

UNITED STATES PATENT AND TRADEMARK OFFICE
CERTIFICATE OF CORRECTION

PATENT NO. : 7,709,230 B2
APPLICATION NO. : 11/777044
DATED : May 4, 2010
INVENTOR(S) : Kubota It is certified that error appears in the above-identified patent and that said Letters Patent is hereby corrected as shown below:

At claim 1, column 60, lines 55-56, delete "α-isomaltosylglucosaccharide forming" and insert --α-isomaltosylglucosaccharide-forming--;

At claim 1, column 60, lines 61-63, delete:
"(c) collecting the released isomaltose wherein said α-isomaltosylglucosaccharide forming enzyme has the following physicochemical properties:" and substitute:
--(c) collecting the released isomaltose;
wherein said α-isomaltosylglucosaccharide-forming enzyme has the following physicochemical properties:--

At claim 4, column 62, line 23, delete "column chromatograph" and insert --chromatography column--.

Signed and Sealed this
Third Day of July, 2012

David J. Kappos
*Director of the United States Patent and Trademark Office*

SEQUENCE LISTING

<160> NUMBER OF SEQ ID NOS: 2

<210> SEQ ID NO 1
<211> LENGTH: 5180
<212> TYPE: DNA

-continued

<213> ORGANISM: Unknown
<220> FEATURE:
<223> OTHER INFORMATION: Bacterial
<220> FEATURE:
<221> NAME/KEY: CDS
<222> LOCATION: (877)..(4731)

<400> SEQUENCE: 1

| | |
|---|---:|
| atctaccggt ttttgtgaag tttggcagta ttcttccgat gaatttgaac gcgcaatatc | 60 |
| aagtgggcgg gaccattggc aacagcttga cgagctacac gaatctcgcg ttccgcattt | 120 |
| atccgcttgg gacaacaacg tacgactgga atgatgatat tggcggttcg gtgaaaacca | 180 |
| taacttctac agagcaatat gggttgaata agaaaccgt gactgttcca gcgattaatt | 240 |
| ctaccaagac attgcaagtg tttacgacta agccttcctc tgtaacggtg ggtggttctg | 300 |
| tgatgacaga gtacagtact ttaactgccc taacgggagc gtcgacaggc tggtactatg | 360 |
| atactgtaca gaaattcact tacgtcaagc ttggttcaag tgcatctgct caatccgttg | 420 |
| tgctaaatgg cgttaataag gtggaatatg aagcagaatt cggcgtgcaa agcggcgttt | 480 |
| caacgaacac gaaccatgca ggttatactg gtacaggatt tgtggacggc tttgagactc | 540 |
| ttggagacaa tgttgctttt gatgtttccg tcaaagccgc aggtacttat acgatgaagg | 600 |
| ttcggtattc atccggtgca ggcaatggct caagagccat ctatgtgaat aacaccaaag | 660 |
| tgacggacct tgccttgccg caaacaacaa gctgggatac atgggggact gctacgttta | 720 |
| gcgtctcgct gagtacaggt ctcaacacgg tgaaagtcag ctatgatggt accagttcac | 780 |
| ttggcattaa tttcgataac atcgcgattg tagagcaata aaaggtcggg agggcaagtc | 840 |
| cctcccttaa tttctaatcg aaagggagta tccttg atg cgt cca cca aac aaa | 894 |
|                                                       Met Arg Pro Pro Asn Lys<br>                                                      1                  5 | |
| gaa att cca cgt att ctt gct ttt ttt aca gcg ttt acg ttg ttt ggt<br>Glu Ile Pro Arg Ile Leu Ala Phe Phe Thr Ala Phe Thr Leu Phe Gly<br>          10                    15                      20 | 942 |
| tca acc ctt gcc ttg ctt cct gct ccg cct gcg cat gcc tat gtc agc<br>Ser Thr Leu Ala Leu Leu Pro Ala Pro Pro Ala His Ala Tyr Val Ser<br>      25                    30                    35 | 990 |
| agc cta gga aat ctc att tct tcg agt gtc acc gga gat acc ttg acg<br>Ser Leu Gly Asn Leu Ile Ser Ser Ser Val Thr Gly Asp Thr Leu Thr<br>40                        45                    50 | 1038 |
| cta act gtt gat aac ggt gcg gag ccg agt gat gac ctc ttg att gtt<br>Leu Thr Val Asp Asn Gly Ala Glu Pro Ser Asp Asp Leu Leu Ile Val<br>55                    60                    65                    70 | 1086 |
| caa gcg gtg caa aac ggt att ttg aag gtg gat tat cgt cca aat agc<br>Gln Ala Val Gln Asn Gly Ile Leu Lys Val Asp Tyr Arg Pro Asn Ser<br>                75                    80                    85 | 1134 |
| ata acg ccg agc gcg aag acg ccg atg ctg gat ccg aac aaa act tgg<br>Ile Thr Pro Ser Ala Lys Thr Pro Met Leu Asp Pro Asn Lys Thr Trp<br>      90                    95                   100 | 1182 |
| tca gct gta gga gct acg att aat acg aca gcc aat cca atg acc atc<br>Ser Ala Val Gly Ala Thr Ile Asn Thr Thr Ala Asn Pro Met Thr Ile<br>          105                   110                  115 | 1230 |
| acg act tcc aat atg aag att gag att acc aag aat cca gta cga atg<br>Thr Thr Ser Asn Met Lys Ile Glu Ile Thr Lys Asn Pro Val Arg Met<br>120                   125                   130 | 1278 |
| acg gtc aag aag gcg gac ggc act acg cta ttc tgg gaa cca tca ggc<br>Thr Val Lys Lys Ala Asp Gly Thr Thr Leu Phe Trp Glu Pro Ser Gly<br>135                 140                  145               150 | 1326 |
| gga ggg gta ttc tca gac ggt gtg cgc ttc ctt cat gcc aca ggg gat<br>Gly Gly Val Phe Ser Asp Gly Val Arg Phe Leu His Ala Thr Gly Asp | 1374 |

-continued

```
                155                 160                 165
aat atg tat ggc atc cgg agc ttc aat gct ttt gat agc ggg ggt gac    1422
Asn Met Tyr Gly Ile Arg Ser Phe Asn Ala Phe Asp Ser Gly Gly Asp
        170                 175                 180 ctg ctg cgg aat tcg tcc aat cat gcc gcc cat gcg ggt gaa cag gga    1470
Leu Leu Arg Asn Ser Ser Asn His Ala Ala His Ala Gly Glu Gln Gly
            185                 190                 195 gat tcc ggt ggt ccg ctt att tgg agt acg gca gga tat gga cta tta    1518
Asp Ser Gly Gly Pro Leu Ile Trp Ser Thr Ala Gly Tyr Gly Leu Leu
200                 205                 210 gtc gat agc gat ggc ggc tac ccc tat aca gat agc aca acc ggt caa    1566
Val Asp Ser Asp Gly Gly Tyr Pro Tyr Thr Asp Ser Thr Thr Gly Gln
215                 220                 225                 230 atg gag ttt tat tat ggt ggg acc cct cct gag gga cgt cgt tat gcg    1614
Met Glu Phe Tyr Tyr Gly Gly Thr Pro Pro Glu Gly Arg Arg Tyr Ala
                235                 240                 245 aaa caa aac gtg gaa tat tat att atg ctc gga acc ccc aag gaa att    1662
Lys Gln Asn Val Glu Tyr Tyr Ile Met Leu Gly Thr Pro Lys Glu Ile
            250                 255                 260 atg acc gac gta ggg gaa atc aca ggg aaa ccg cct atg ctg cct aag    1710
Met Thr Asp Val Gly Glu Ile Thr Gly Lys Pro Pro Met Leu Pro Lys
        265                 270                 275 tgg tcg ctt gga ttc atg aac ttt gag tgg gat acg aat caa acg gag    1758
Trp Ser Leu Gly Phe Met Asn Phe Glu Trp Asp Thr Asn Gln Thr Glu
280                 285                 290 ttt acg aat aat gtg gat acg tat cgt gcc aaa aat atc ccc ata gat    1806
Phe Thr Asn Asn Val Asp Thr Tyr Arg Ala Lys Asn Ile Pro Ile Asp
295                 300                 305                 310 gct tac gcc ttc gac tat gac tgg aaa aag tac ggg gaa acc aac tat    1854
Ala Tyr Ala Phe Asp Tyr Asp Trp Lys Lys Tyr Gly Glu Thr Asn Tyr
                315                 320                 325 ggt gaa ttc gcg tgg aat acg act aat ttc cct tct gcg tca acg act    1902
Gly Glu Phe Ala Trp Asn Thr Thr Asn Phe Pro Ser Ala Ser Thr Thr
            330                 335                 340 tct tta aag tca aca atg gat gct aaa ggc atc aaa atg atc gga att    1950
Ser Leu Lys Ser Thr Met Asp Ala Lys Gly Ile Lys Met Ile Gly Ile
        345                 350                 355 aca aaa ccc cgc atc gtt acg aag gat gct tca gcg aat gtg acg acc    1998
Thr Lys Pro Arg Ile Val Thr Lys Asp Ala Ser Ala Asn Val Thr Thr
    360                 365                 370 caa ggg acg gac gcg aca aat ggc ggt tat ttt tat cca ggc cat aac    2046
Gln Gly Thr Asp Ala Thr Asn Gly Gly Tyr Phe Tyr Pro Gly His Asn
375                 380                 385                 390 gag tat cag gat tat ttc att ccc gta act gtg cgt agt atc gat cct    2094
Glu Tyr Gln Asp Tyr Phe Ile Pro Val Thr Val Arg Ser Ile Asp Pro
                395                 400                 405 tac aat gct aac gaa cgt gct tgg ttc tgg aat cat tcc aca gat gcg    2142
Tyr Asn Ala Asn Glu Arg Ala Trp Phe Trp Asn His Ser Thr Asp Ala
            410                 415                 420 ctt aat aaa ggg atc gta ggt tgg tgg aat gac gag acg gat aaa gta    2190
Leu Asn Lys Gly Ile Val Gly Trp Trp Asn Asp Glu Thr Asp Lys Val
        425                 430                 435 tct tcg ggt gga gcg tta tat tgg ttt ggc aat ttc aca aca ggc cac    2238
Ser Ser Gly Gly Ala Leu Tyr Trp Phe Gly Asn Phe Thr Thr Gly His
    440                 445                 450 atg tct cag acg atg tac gaa ggg ggg cgg gct tac acg agt gga gcg    2286
Met Ser Gln Thr Met Tyr Glu Gly Gly Arg Ala Tyr Thr Ser Gly Ala
455                 460                 465                 470 cag cgt gtt tgg caa acg gct aga acc ttc tac cca ggt gcc cag cgg    2334
```

```
                Gln Arg Val Trp Gln Thr Ala Arg Thr Phe Tyr Pro Gly Ala Gln Arg
                                475                 480                 485 tat gcg act acg ctt tgg tct ggc gat att ggc att caa tac aat aaa      2382
Tyr Ala Thr Thr Leu Trp Ser Gly Asp Ile Gly Ile Gln Tyr Asn Lys
            490                 495                 500 ggc gaa cgg atc aat tgg gct gcc ggg atg cag gag caa agg gca gtt      2430
Gly Glu Arg Ile Asn Trp Ala Ala Gly Met Gln Glu Gln Arg Ala Val
        505                 510                 515 atg cta tcc tcc gtg aac aat ggc cag gtg aaa tgg ggc atg gat acc      2478
Met Leu Ser Ser Val Asn Asn Gly Gln Val Lys Trp Gly Met Asp Thr
    520                 525                 530 ggc gga ttc aat cag cag gat ggc acg acg aac aat ccg aat ccc gat      2526
Gly Gly Phe Asn Gln Gln Asp Gly Thr Thr Asn Asn Pro Asn Pro Asp
535                 540                 545                 550 tta tac gct cgg tgg atg cag ttc agt gcc cta acg cct gtt ttc cga      2574
Leu Tyr Ala Arg Trp Met Gln Phe Ser Ala Leu Thr Pro Val Phe Arg
                555                 560                 565 gtg cat ggg aac aac cat cag cag cgc cag cca tgg tac ttc gga tcg      2622
Val His Gly Asn Asn His Gln Gln Arg Gln Pro Trp Tyr Phe Gly Ser
            570                 575                 580 act gcg gag gag gcc tcc aaa gag gca att cag ctg cgg tac tcc ctg      2670
Thr Ala Glu Glu Ala Ser Lys Glu Ala Ile Gln Leu Arg Tyr Ser Leu
        585                 590                 595 atc cct tat atg tat gcc tat gag aga agt gct tac gag aat ggg aat      2718
Ile Pro Tyr Met Tyr Ala Tyr Glu Arg Ser Ala Tyr Glu Asn Gly Asn
    600                 605                 610 ggg ctc gtt cgg cca ttg atg caa gcc tat cca aca gat gcg gcc gtc      2766
Gly Leu Val Arg Pro Leu Met Gln Ala Tyr Pro Thr Asp Ala Ala Val
615                 620                 625                 630 aaa aat tac acg gat gct tgg atg ttt ggt gac tgg ctg ctg gct gca      2814
Lys Asn Tyr Thr Asp Ala Trp Met Phe Gly Asp Trp Leu Leu Ala Ala
                635                 640                 645 cct gtg gta gat aaa cag cag acg agt aag gat atc tat tta ccg tct      2862
Pro Val Val Asp Lys Gln Gln Thr Ser Lys Asp Ile Tyr Leu Pro Ser
            650                 655                 660 ggg tca tgg att gac tat gcg cga ggc aat gca ata act ggc ggt caa      2910
Gly Ser Trp Ile Asp Tyr Ala Arg Gly Asn Ala Ile Thr Gly Gly Gln
        665                 670                 675 acc atc cga tat tcg gtt aat ccg gac acg ttg aca gac atg cct ctc      2958
Thr Ile Arg Tyr Ser Val Asn Pro Asp Thr Leu Thr Asp Met Pro Leu
    680                 685                 690 ttt att aaa aaa ggt gcc att att cca aca cag aaa gtg cag gat tac      3006
Phe Ile Lys Lys Gly Ala Ile Ile Pro Thr Gln Lys Val Gln Asp Tyr
695                 700                 705                 710 gta ggg cag gct tcc gtc act tcc gtt gat gtg gat gtg ttt ccg gat      3054
Val Gly Gln Ala Ser Val Thr Ser Val Asp Val Asp Val Phe Pro Asp
                715                 720                 725 acg acg cag tcg agt ttc acg tac tac gat gat gat ggc gcc agt tat      3102
Thr Thr Gln Ser Ser Phe Thr Tyr Tyr Asp Asp Asp Gly Ala Ser Tyr
            730                 735                 740 aac tat gag agc ggc act tat ttt aag caa aat atg act gct cag gat      3150
Asn Tyr Glu Ser Gly Thr Tyr Phe Lys Gln Asn Met Thr Ala Gln Asp
        745                 750                 755 aat ggg tca ggc tcg tta agt ttt act tta gga gca aag agt ggc agt      3198
Asn Gly Ser Gly Ser Leu Ser Phe Thr Leu Gly Ala Lys Ser Gly Ser
    760                 765                 770 tac acg ccg gct ctc caa tcc tat atc gtt aag ctg cac ggt tct gct      3246
Tyr Thr Pro Ala Leu Gln Ser Tyr Ile Val Lys Leu His Gly Ser Ala
775                 780                 785                 790
```

| | | |
|---|---|---|
| gga act tct gtt acg aat aac agc gca gct atg aca tct tat gca agc<br>Gly Thr Ser Val Thr Asn Asn Ser Ala Ala Met Thr Ser Tyr Ala Ser<br>795                            800                       805 | | 3294 |
| ttg gaa gca tta aaa gct gct gct ggg gaa ggc tgg gcg act ggg aag<br>Leu Glu Ala Leu Lys Ala Ala Ala Gly Glu Gly Trp Ala Thr Gly Lys<br>        810                       815                       820 | | 3342 |
| gac att tat ggg gat gtc acc tat gtg aaa gtg acg gca ggt aca gct<br>Asp Ile Tyr Gly Asp Val Thr Tyr Val Lys Val Thr Ala Gly Thr Ala<br>             825                     830                     835 | | 3390 |
| tct tct aaa tct att gct gtt aca ggt gtt gct gcc gtg agc gca act<br>Ser Ser Lys Ser Ile Ala Val Thr Gly Val Ala Ala Val Ser Ala Thr<br>840                            845                       850 | | 3438 |
| act tcg caa tac gaa gct gag gat gca tcg ctt tct ggc aat tcg gtt<br>Thr Ser Gln Tyr Glu Ala Glu Asp Ala Ser Leu Ser Gly Asn Ser Val<br>855                          860                       865                   870 | | 3486 |
| gct gca aag gcg tcc ata aac acg aat cat acc gga tat acg gga act<br>Ala Ala Lys Ala Ser Ile Asn Thr Asn His Thr Gly Tyr Thr Gly Thr<br>                   875                     880                     885 | | 3534 |
| gga ttt gta gat ggt ttg ggg aat gat ggc gct ggt gtc acc ttc tat<br>Gly Phe Val Asp Gly Leu Gly Asn Asp Gly Ala Gly Val Thr Phe Tyr<br>        890                       895                       900 | | 3582 |
| cca aag gtg aaa act ggc ggt gac tac aat gtc tcc ttg cgt tat gcg<br>Pro Lys Val Lys Thr Gly Gly Asp Tyr Asn Val Ser Leu Arg Tyr Ala<br>             905                     910                     915 | | 3630 |
| aat gct tca ggc acg gct aag tca gtc agt att ttt gtt aat gga aaa<br>Asn Ala Ser Gly Thr Ala Lys Ser Val Ser Ile Phe Val Asn Gly Lys<br>920                            925                       930 | | 3678 |
| aga gtg aag tcc acc tcg ctc gct aat ctc gca aat tgg gac act tgg<br>Arg Val Lys Ser Thr Ser Leu Ala Asn Leu Ala Asn Trp Asp Thr Trp<br>935                            940                       945                   950 | | 3726 |
| tct aca caa tct gag aca ctg ccg ttg acg gca ggt gtg aat gtt gtg<br>Ser Thr Gln Ser Glu Thr Leu Pro Leu Thr Ala Gly Val Asn Val Val<br>                   955                     960                     965 | | 3774 |
| acc tat aaa tat tac tcc gat gcg gga gat aca ggc aat gtt aac atc<br>Thr Tyr Lys Tyr Tyr Ser Asp Ala Gly Asp Thr Gly Asn Val Asn Ile<br>        970                       975                     980 | | 3822 |
| gac aac atc acg gta cct ttt gcg cca att atc ggt aag tat gaa gca<br>Asp Asn Ile Thr Val Pro Phe Ala Pro Ile Ile Gly Lys Tyr Glu Ala<br>             985                     990                     995 | | 3870 |
| gag agt gct gag ctt tct ggt ggc agc tca ttg aac acg aac cat<br>Glu Ser Ala Glu Leu Ser Gly Gly Ser Ser Leu Asn Thr Asn His<br>1000                         1005                       1010 | | 3915 |
| tgg tac tac agt ggt acg gct ttt gta gac ggt ttg agt gct gta<br>Trp Tyr Tyr Ser Gly Thr Ala Phe Val Asp Gly Leu Ser Ala Val<br>1015                         1020                       1025 | | 3960 |
| ggc gcg cag gtg aaa tac aac gtg aat gtc cct agc gca gga agt<br>Gly Ala Gln Val Lys Tyr Asn Val Asn Val Pro Ser Ala Gly Ser<br>1030                         1035                       1040 | | 4005 |
| tat cag gta gcg ctg cga tat gcg aat ggc agt gca gcg acg aaa<br>Tyr Gln Val Ala Leu Arg Tyr Ala Asn Gly Ser Ala Ala Thr Lys<br>1045                         1050                       1055 | | 4050 |
| acg ttg agt act tat atc aat gga gcc aag ctg ggg caa acc agt<br>Thr Leu Ser Thr Tyr Ile Asn Gly Ala Lys Leu Gly Gln Thr Ser<br>1060                         1065                       1070 | | 4095 |
| ttt acg agt cct ggt acg aat tgg aat gtt tgg cag gat aat gtg<br>Phe Thr Ser Pro Gly Thr Asn Trp Asn Val Trp Gln Asp Asn Val<br>1075                         1080                       1085 | | 4140 |
| caa acg gtg acg tta aat gca ggg gca aac acg att gcg ttt aaa<br>Gln Thr Val Thr Leu Asn Ala Gly Ala Asn Thr Ile Ala Phe Lys<br>1090                         1095                       1100 | | 4185 |

```
tac gac gcc gct gac agc ggg aac atc aac gta gat cgt ctg ctt      4230
Tyr Asp Ala Ala Asp Ser Gly Asn Ile Asn Val Asp Arg Leu Leu
    1105                1110                1115 ctt tca act tcg gca gcg gga acg ccg gtt tct gag cag aac ctg      4275
Leu Ser Thr Ser Ala Ala Gly Thr Pro Val Ser Glu Gln Asn Leu
1120                1125                1130 cta gac aat ccc ggt ttc gag cgt gac acg agt caa acc aat aac      4320
Leu Asp Asn Pro Gly Phe Glu Arg Asp Thr Ser Gln Thr Asn Asn
    1135                1140                1145 tgg att gag tgg cat cca ggc acg caa gct gtt gct ttt ggc gtt      4365
Trp Ile Glu Trp His Pro Gly Thr Gln Ala Val Ala Phe Gly Val
1150                1155                1160 gat agc ggc tca acc acc aat ccg ccg gaa tcc ccg tgg tcg ggt      4410
Asp Ser Gly Ser Thr Thr Asn Pro Pro Glu Ser Pro Trp Ser Gly
    1165                1170                1175 gat aag cgt gcc tac ttc ttt gca gca ggt gcc tat caa caa agc      4455
Asp Lys Arg Ala Tyr Phe Phe Ala Ala Gly Ala Tyr Gln Gln Ser
1180                1185                1190 atc cat caa acc att agt gtt cct gtt aat aat gta aaa tac aaa      4500
Ile His Gln Thr Ile Ser Val Pro Val Asn Asn Val Lys Tyr Lys
    1195                1200                1205 ttt gaa gcc tgg gtc cgc atg aag aat acg acg ccg acg acg gca      4545
Phe Glu Ala Trp Val Arg Met Lys Asn Thr Thr Pro Thr Thr Ala
1210                1215                1220 aga gcc gaa att caa aac tat ggc gga tca gcc att tat gcg aac      4590
Arg Ala Glu Ile Gln Asn Tyr Gly Gly Ser Ala Ile Tyr Ala Asn
    1225                1230                1235 ata agt aac agc ggt gtt tgg aaa tat atc agc gta agt gat att      4635
Ile Ser Asn Ser Gly Val Trp Lys Tyr Ile Ser Val Ser Asp Ile
1240                1245                1250 atg gtg acc aat ggt cag ata gat gtt gga ttt tac gtg gat tca      4680
Met Val Thr Asn Gly Gln Ile Asp Val Gly Phe Tyr Val Asp Ser
    1255                1260                1265 cct ggt gga act acg ctt cac att gat gat gtg cgc gta acc aaa      4725
Pro Gly Gly Thr Thr Leu His Ile Asp Asp Val Arg Val Thr Lys
1270                1275                1280 caa taa acaaacaacc agctctcccg ttaatgggag gctggttgt tgttatgat    4781
Gln aatccatcta tttagagtgg attaaacgtt ttgaagtgct tgctgaactt cttgcacaat 4841 ggataacgcc gcggtgcggg cacttgagaa agcacgttct gcaagctctc ccttacctgt 4901 acagccgtct ccgcagaagt agaaaggaac gttttccacg cgtatcggca gcagattatt 4961 ggaagcaatg tttttcacgc tggaaaccat cgctttcttg gaaacccgtt tcacggctgt 5021 gacatcgcgc cagcctggat aatgtttatc aaataaggct tccatttgga ggttcttctc 5081 ttccaggtac gctttgcgct gctcctcgtt atcaaagcgg tcgcttaagt atgcgatacc 5141 ttgcagcagc tgcccgcctt ctggtactag tgtgtgatc                       5180

<210> SEQ ID NO 2
<211> LENGTH: 3869
<212> TYPE: DNA
<213> ORGANISM: Unknown
<220> FEATURE:
<223> OTHER INFORMATION: Bacterial
<220> FEATURE:
<221> NAME/KEY: CDS
<222> LOCATION: (241)..(3522)

<400> SEQUENCE: 2
```

-continued

| | | |
|---|---|---|
| tcatcgctac tggcaatcgg attcaaacaa atggctgcag ctcgcacaga cgattgtgga | | 60 |
| aagggaatat ctgatttaac catacggcgg tcgcgattga ttgaatagga ttcgtggccg | | 120 |
| cctaatattg aaaggggga tgcgtggagc agcgcatgca cggcgaggaa taactgttgt | | 180 |
| tggagcctct aagtcattca tgtttagcaa acaaatttcg gtacgaaagg ggaaatgttt | | 240 |

| | | |
|---|---|---|
| atg tat gta agg aat cta aca ggt tca ttc cga ttt tct ctc tct ttt | 288 |
| Met Tyr Val Arg Asn Leu Thr Gly Ser Phe Arg Phe Ser Leu Ser Phe | |
| 1               5                   10                  15 | |
| ttg ctc tgt ttc tgt ctc ttc gtc ccc tct att tat gcc att gat ggt | 336 |
| Leu Leu Cys Phe Cys Leu Phe Val Pro Ser Ile Tyr Ala Ile Asp Gly | |
|         20                  25                  30 | |
| gtt tat cat gcg cca tac gga atc gat gat ctg tac gag att cag gcg | 384 |
| Val Tyr His Ala Pro Tyr Gly Ile Asp Asp Leu Tyr Glu Ile Gln Ala | |
|     35                  40                  45 | |
| acg gag cgg agt cca aga gat ccc gtt gca ggc gat act gtg tat atc | 432 |
| Thr Glu Arg Ser Pro Arg Asp Pro Val Ala Gly Asp Thr Val Tyr Ile | |
| 50                  55                  60 | |
| aag ata aca acg tgg ccc att gaa tca gga caa acg gct tgg gtg acc | 480 |
| Lys Ile Thr Thr Trp Pro Ile Glu Ser Gly Gln Thr Ala Trp Val Thr | |
| 65                  70                  75                  80 | |
| tgg acg aaa aac ggt gtc aat caa gct gct gtc gga gca gca ttc aaa | 528 |
| Trp Thr Lys Asn Gly Val Asn Gln Ala Ala Val Gly Ala Ala Phe Lys | |
|             85                  90                  95 | |
| tac aac agc ggc aac aac act tac tgg gaa gcg aac ctt ggc act ttt | 576 |
| Tyr Asn Ser Gly Asn Asn Thr Tyr Trp Glu Ala Asn Leu Gly Thr Phe | |
|         100                 105                 110 | |
| gca aaa ggg gac gtg atc agt tat acc gtt cat ggc aac aag gat ggc | 624 |
| Ala Lys Gly Asp Val Ile Ser Tyr Thr Val His Gly Asn Lys Asp Gly | |
|     115                 120                 125 | |
| gcg aat gag aag gtt atc ggt cct ttt act ttt acc gta acg gga tgg | 672 |
| Ala Asn Glu Lys Val Ile Gly Pro Phe Thr Phe Thr Val Thr Gly Trp | |
| 130                 135                 140 | |
| gaa tcc gtt agc agt atc agc tct att acg gat aat acg aac cgt gtt | 720 |
| Glu Ser Val Ser Ser Ile Ser Ser Ile Thr Asp Asn Thr Asn Arg Val | |
| 145                 150                 155                 160 | |
| gtg ctg aat gcg gtg ccg aat aca ggc aca ttg aag cca aag atc aac | 768 |
| Val Leu Asn Ala Val Pro Asn Thr Gly Thr Leu Lys Pro Lys Ile Asn | |
|             165                 170                 175 | |
| ctt tcc ttt acg gcg gat gat gtc ctc cgc gta cag gtt tct cca acc | 816 |
| Leu Ser Phe Thr Ala Asp Asp Val Leu Arg Val Gln Val Ser Pro Thr | |
|         180                 185                 190 | |
| gga aca gga acg tta agc agt gga ctt agt aat tac aca gtt tca gat | 864 |
| Gly Thr Gly Thr Leu Ser Ser Gly Leu Ser Asn Tyr Thr Val Ser Asp | |
|     195                 200                 205 | |
| acc gcc tca acc act tgg ctt aca act tcc aag ctg aag gtg aag gtg | 912 |
| Thr Ala Ser Thr Thr Trp Leu Thr Thr Ser Lys Leu Lys Val Lys Val | |
| 210                 215                 220 | |
| gat aag aat cca ttc aaa ctt agt gtg tat aag cct gat gga acg acg | 960 |
| Asp Lys Asn Pro Phe Lys Leu Ser Val Tyr Lys Pro Asp Gly Thr Thr | |
| 225                 230                 235                 240 | |
| ttg att gcc cgt caa tat gac agc act acg aat cgt aac att gcc tgg | 1008 |
| Leu Ile Ala Arg Gln Tyr Asp Ser Thr Thr Asn Arg Asn Ile Ala Trp | |
|             245                 250                 255 | |
| tta acc aat ggc agt aca atc atc gac aag gta gaa gat cat ttt tat | 1056 |
| Leu Thr Asn Gly Ser Thr Ile Ile Asp Lys Val Glu Asp His Phe Tyr | |
|         260                 265                 270 | |
| tca ccg gct tcc gag gag ttt ttt ggc ttt gga gag cat tac aac aac | 1104 |
| Ser Pro Ala Ser Glu Glu Phe Phe Gly Phe Gly Glu His Tyr Asn Asn | |
|     275                 280                 285 | |

```
ttc cgt aaa cgc gga aat gat gtg gac acc tat gtg ttc aac cag tat      1152
Phe Arg Lys Arg Gly Asn Asp Val Asp Thr Tyr Val Phe Asn Gln Tyr
    290                 295                 300 aag aat caa aat gac cgc acc tac atg gca att cct ttt atg ctt aac      1200
Lys Asn Gln Asn Asp Arg Thr Tyr Met Ala Ile Pro Phe Met Leu Asn
305                 310                 315                 320 agc agc ggt tat ggc att ttc gta aat tca acg tat tat tcc aaa ttt      1248
Ser Ser Gly Tyr Gly Ile Phe Val Asn Ser Thr Tyr Tyr Ser Lys Phe
            325                 330                 335 cgg ttg gca acc gaa cgc acc gat atg ttc agc ttt acg gct gat aca      1296
Arg Leu Ala Thr Glu Arg Thr Asp Met Phe Ser Phe Thr Ala Asp Thr
                340                 345                 350 ggg ggt agt gcc gcc tcg atg ctg gat tat tat ttc att tac ggt aat      1344
Gly Gly Ser Ala Ala Ser Met Leu Asp Tyr Tyr Phe Ile Tyr Gly Asn
        355                 360                 365 gat ttg aaa aat gtg gtg agt aac tac gct aac att acc ggt aag cca      1392
Asp Leu Lys Asn Val Val Ser Asn Tyr Ala Asn Ile Thr Gly Lys Pro
370                 375                 380 aca gcg ctg ccg aaa tgg gct ttc ggg tta tgg atg tca gct aac gag      1440
Thr Ala Leu Pro Lys Trp Ala Phe Gly Leu Trp Met Ser Ala Asn Glu
385                 390                 395                 400 tgg gat cgt caa acc aag gtg aat aca gcc att aat aac gcg aac tcc      1488
Trp Asp Arg Gln Thr Lys Val Asn Thr Ala Ile Asn Asn Ala Asn Ser
            405                 410                 415 aat aat att ccg gct aca gcg gtt gtg ctc gaa cag tgg agt gat gag      1536
Asn Asn Ile Pro Ala Thr Ala Val Val Leu Glu Gln Trp Ser Asp Glu
                420                 425                 430 aac acg ttt tat att ttc aat gat gcc acc tat acc ccg aaa acg ggc      1584
Asn Thr Phe Tyr Ile Phe Asn Asp Ala Thr Tyr Thr Pro Lys Thr Gly
        435                 440                 445 agt gct gcg cat gcc tat acc gat ttc act ttc ccg aca tct ggg aga      1632
Ser Ala Ala His Ala Tyr Thr Asp Phe Thr Phe Pro Thr Ser Gly Arg
450                 455                 460 tgg acg gat cca aaa gcg atg gca gac aat gtg cat aac aat ggg atg      1680
Trp Thr Asp Pro Lys Ala Met Ala Asp Asn Val His Asn Asn Gly Met
465                 470                 475                 480 aag ctg gtg ctt tgg cag gtc cct att cag aaa tgg act tca acg ccc      1728
Lys Leu Val Leu Trp Gln Val Pro Ile Gln Lys Trp Thr Ser Thr Pro
            485                 490                 495 tat acc cag aaa gat aat gat gaa gcc tat atg acg gct cag aat tat      1776
Tyr Thr Gln Lys Asp Asn Asp Glu Ala Tyr Met Thr Ala Gln Asn Tyr
                500                 505                 510 gca gtt ggc aac ggt agc gga ggc cag tac agg ata cct tca gga caa      1824
Ala Val Gly Asn Gly Ser Gly Gly Gln Tyr Arg Ile Pro Ser Gly Gln
        515                 520                 525 tgg ttc gag aac agt ttg ctg ctt gat ttt acg aat acg gcc gcc aaa      1872
Trp Phe Glu Asn Ser Leu Leu Leu Asp Phe Thr Asn Thr Ala Ala Lys
530                 535                 540 aac tgg tgg atg tct aaa cgc gct tat ctg ttt gat ggt gtg ggt atc      1920
Asn Trp Trp Met Ser Lys Arg Ala Tyr Leu Phe Asp Gly Val Gly Ile
545                 550                 555                 560 gac ggc ttc aaa aca gat ggc ggt gaa atg gta tgg ggt cgc tca aat      1968
Asp Gly Phe Lys Thr Asp Gly Gly Glu Met Val Trp Gly Arg Ser Asn
            565                 570                 575 act ttc tca aac ggt aag aaa ggc aat gaa atg cgc aat caa tac ccg      2016
Thr Phe Ser Asn Gly Lys Lys Gly Asn Glu Met Arg Asn Gln Tyr Pro
                580                 585                 590 aat gag tat gtg aaa gcc tat aac gag tac gcg cgc tcg aag aaa gcc      2064
Asn Glu Tyr Val Lys Ala Tyr Asn Glu Tyr Ala Arg Ser Lys Lys Ala
```

-continued

|  |  |  |  |  |  |  |  |  |  |  |  |  |  |  |  |  |
|---|---|---|---|---|---|---|---|---|---|---|---|---|---|---|---|---|
|  |  |  | 595 |  |  |  | 600 |  |  |  | 605 |  |  |  |  |  |
| gat | gcg | gtc | tcc | ttt | agc | cgt | tcc | ggc | acg | caa | ggc | gca | cag | gcg | aat | 2112 |
| Asp | Ala | Val | Ser | Phe | Ser | Arg | Ser | Gly | Thr | Gln | Gly | Ala | Gln | Ala | Asn |  |
| 610 |  |  |  |  | 615 |  |  |  |  | 620 |  |  |  |  |  |  |
| cag | att | ttc | tgg | tcc | ggt | gac | caa | gag | tcg | acg | ttt | ggt | gct | ttt | caa | 2160 |
| Gln | Ile | Phe | Trp | Ser | Gly | Asp | Gln | Glu | Ser | Thr | Phe | Gly | Ala | Phe | Gln |  |
| 625 |  |  |  |  | 630 |  |  |  |  | 635 |  |  |  |  | 640 |  |
| caa | gct | gtg | aat | gca | ggg | ctt | acg | gca | agt | atg | tct | ggc | gtt | cct | tat | 2208 |
| Gln | Ala | Val | Asn | Ala | Gly | Leu | Thr | Ala | Ser | Met | Ser | Gly | Val | Pro | Tyr |  |
|  |  |  |  | 645 |  |  |  |  | 650 |  |  |  |  | 655 |  |  |
| tgg | agc | tgg | gat | atg | gca | ggc | ttt | aca | ggc | act | tat | cca | acg | gct | gag | 2256 |
| Trp | Ser | Trp | Asp | Met | Ala | Gly | Phe | Thr | Gly | Thr | Tyr | Pro | Thr | Ala | Glu |  |
|  |  |  | 660 |  |  |  |  | 665 |  |  |  |  | 670 |  |  |  |
| ttg | tac | aaa | cgt | gct | act | gaa | atg | gct | gct | ttt | gca | ccg | gtc | atg | cag | 2304 |
| Leu | Tyr | Lys | Arg | Ala | Thr | Glu | Met | Ala | Ala | Phe | Ala | Pro | Val | Met | Gln |  |
|  |  | 675 |  |  |  |  | 680 |  |  |  |  | 685 |  |  |  |  |
| ttt | cat | tcc | gag | tct | aac | ggc | agc | tct | ggt | atc | aac | gag | gaa | cgt | tct | 2352 |
| Phe | His | Ser | Glu | Ser | Asn | Gly | Ser | Ser | Gly | Ile | Asn | Glu | Glu | Arg | Ser |  |
|  | 690 |  |  |  |  | 695 |  |  |  |  | 700 |  |  |  |  |  |
| cca | tgg | aac | gca | caa | gcg | cgt | aca | ggc | gac | aat | acg | atc | att | agt | cat | 2400 |
| Pro | Trp | Asn | Ala | Gln | Ala | Arg | Thr | Gly | Asp | Asn | Thr | Ile | Ile | Ser | His |  |
| 705 |  |  |  |  | 710 |  |  |  |  | 715 |  |  |  |  | 720 |  |
| ttt | gcc | aaa | tat | acg | aat | acg | cgc | atg | aat | ttg | ctt | cct | tat | att | tat | 2448 |
| Phe | Ala | Lys | Tyr | Thr | Asn | Thr | Arg | Met | Asn | Leu | Leu | Pro | Tyr | Ile | Tyr |  |
|  |  |  |  | 725 |  |  |  |  | 730 |  |  |  |  | 735 |  |  |
| agc | gaa | gcg | aag | atg | gct | agt | gat | act | ggc | gtt | ccc | atg | atg | cgc | gcc | 2496 |
| Ser | Glu | Ala | Lys | Met | Ala | Ser | Asp | Thr | Gly | Val | Pro | Met | Met | Arg | Ala |  |
|  |  |  | 740 |  |  |  |  | 745 |  |  |  |  | 750 |  |  |  |
| atg | gcg | ctt | gaa | tat | ccg | aag | gac | acg | aac | acg | tac | ggt | ttg | aca | caa | 2544 |
| Met | Ala | Leu | Glu | Tyr | Pro | Lys | Asp | Thr | Asn | Thr | Tyr | Gly | Leu | Thr | Gln |  |
|  |  | 755 |  |  |  |  | 760 |  |  |  |  | 765 |  |  |  |  |
| cag | tat | atg | ttc | gga | ggt | aat | tta | ctt | att | gct | cct | gtt | atg | aat | cag | 2592 |
| Gln | Tyr | Met | Phe | Gly | Gly | Asn | Leu | Leu | Ile | Ala | Pro | Val | Met | Asn | Gln |  |
| 770 |  |  |  |  | 775 |  |  |  |  | 780 |  |  |  |  |  |  |
| gga | gaa | aca | aac | aag | agt | att | tat | ctt | ccg | cag | ggg | gat | tgg | atc | gat | 2640 |
| Gly | Glu | Thr | Asn | Lys | Ser | Ile | Tyr | Leu | Pro | Gln | Gly | Asp | Trp | Ile | Asp |  |
| 785 |  |  |  |  | 790 |  |  |  |  | 795 |  |  |  |  | 800 |  |
| ttc | tgg | ttc | ggt | gct | cag | cgt | cct | ggc | ggt | cga | aca | atc | agc | tac | acg | 2688 |
| Phe | Trp | Phe | Gly | Ala | Gln | Arg | Pro | Gly | Gly | Arg | Thr | Ile | Ser | Tyr | Thr |  |
|  |  |  |  | 805 |  |  |  |  | 810 |  |  |  |  | 815 |  |  |
| gcc | ggc | atc | gat | gat | cta | ccg | gtt | ttt | gtg | aag | ttt | ggc | agt | att | ctt | 2736 |
| Ala | Gly | Ile | Asp | Asp | Leu | Pro | Val | Phe | Val | Lys | Phe | Gly | Ser | Ile | Leu |  |
|  |  |  | 820 |  |  |  |  | 825 |  |  |  |  | 830 |  |  |  |
| ccg | atg | aat | ttg | aac | gcg | caa | tat | caa | gtg | ggc | ggg | acc | att | ggc | aac | 2784 |
| Pro | Met | Asn | Leu | Asn | Ala | Gln | Tyr | Gln | Val | Gly | Gly | Thr | Ile | Gly | Asn |  |
|  |  | 835 |  |  |  |  | 840 |  |  |  |  | 845 |  |  |  |  |
| agc | ttg | acg | agc | tac | acg | aat | ctc | gcg | ttc | cgc | att | tat | ccg | ctt | ggg | 2832 |
| Ser | Leu | Thr | Ser | Tyr | Thr | Asn | Leu | Ala | Phe | Arg | Ile | Tyr | Pro | Leu | Gly |  |
| 850 |  |  |  |  | 855 |  |  |  |  | 860 |  |  |  |  |  |  |
| aca | aca | acg | tac | gac | tgg | aat | gat | gat | att | ggc | ggt | tcg | gta | aaa | acc | 2880 |
| Thr | Thr | Thr | Tyr | Asp | Trp | Asn | Asp | Asp | Ile | Gly | Gly | Ser | Val | Lys | Thr |  |
| 865 |  |  |  |  | 870 |  |  |  |  | 875 |  |  |  |  | 880 |  |
| ata | act | tct | aca | gag | caa | tat | ggg | ttg | aat | aaa | gaa | acc | gtg | act | gtt | 2928 |
| Ile | Thr | Ser | Thr | Glu | Gln | Tyr | Gly | Leu | Asn | Lys | Glu | Thr | Val | Thr | Val |  |
|  |  |  |  | 885 |  |  |  |  | 890 |  |  |  |  | 895 |  |  |
| cca | gcg | att | aat | tct | acc | aag | aca | ttg | caa | gtg | ttt | acg | act | aag | cct | 2976 |
| Pro | Ala | Ile | Asn | Ser | Thr | Lys | Thr | Leu | Gln | Val | Phe | Thr | Thr | Lys | Pro |  |
|  |  |  | 900 |  |  |  |  | 905 |  |  |  |  | 910 |  |  |  |
| tcc | tct | gta | acg | gtg | ggt | ggt | tct | gtg | atg | aca | gag | tac | agt | act | tta | 3024 |

-continued

| | | | | | | | | | | | | |
|---|---|---|---|---|---|---|---|---|---|---|---|---|
| Ser | Ser | Val | Thr | Val | Gly | Gly | Ser | Val | Met | Thr | Glu | Tyr | Ser | Thr | Leu |
| | 915 | | | | | 920 | | | | | 925 | | | | |

| act | gcc | cta | acg | gga | gcg | tcg | aca | ggc | tgg | tac | tat | gat | act | gta | cag | 3072 |
| Thr | Ala | Leu | Thr | Gly | Ala | Ser | Thr | Gly | Trp | Tyr | Tyr | Asp | Thr | Val | Gln |
| | 930 | | | | | 935 | | | | | 940 | | | | |

| aaa | ttc | act | tac | gtc | aag | ctt | ggt | tca | agt | gca | tct | gct | caa | tcc | gtt | 3120 |
| Lys | Phe | Thr | Tyr | Val | Lys | Leu | Gly | Ser | Ser | Ala | Ser | Ala | Gln | Ser | Val |
| 945 | | | | | 950 | | | | | 955 | | | | | 960 |

| gtg | cta | aat | ggc | gtt | aat | aag | gtg | gaa | tat | gaa | gca | gaa | ttc | ggc | gtg | 3168 |
| Val | Leu | Asn | Gly | Val | Asn | Lys | Val | Glu | Tyr | Glu | Ala | Glu | Phe | Gly | Val |
| | | | | 965 | | | | | 970 | | | | | 975 | |

| caa | agc | ggc | gtt | tca | acg | aac | acg | aac | cat | gca | ggt | tat | act | ggt | aca | 3216 |
| Gln | Ser | Gly | Val | Ser | Thr | Asn | Thr | Asn | His | Ala | Gly | Tyr | Thr | Gly | Thr |
| | | | | 980 | | | | | 985 | | | | | 990 | |

| gga | ttt | gtg | gac | ggc | ttt | gag | act | ctt | gga | gac | aat | gtt | | gct | ttt | gat | 3264 |
| Gly | Phe | Val | Asp | Gly | Phe | Glu | Thr | Leu | Gly | Asp | Asn | Val | | Ala | Phe | Asp |
| | | 995 | | | | | 1000 | | | | | 1005 | | | | |

| gtt | tcc | gtc | aaa | gcc | gca | ggt | act | tat | acg | atg | aag | | gtt | cgg | tat | 3309 |
| Val | Ser | Val | Lys | Ala | Ala | Gly | Thr | Tyr | Thr | Met | Lys | | Val | Arg | Tyr |
| | 1010 | | | | | 1015 | | | | | 1020 | | | | |

| tca | tcc | ggt | gca | ggc | aat | ggc | tca | aga | gcc | atc | tat | | gtg | aat | aac | 3354 |
| Ser | Ser | Gly | Ala | Gly | Asn | Gly | Ser | Arg | Ala | Ile | Tyr | | Val | Asn | Asn |
| | 1025 | | | | | 1030 | | | | | 1035 | | | | |

| acc | aaa | gtg | acg | gac | ctt | gcc | ttg | ccg | caa | aca | aca | agc | tgg | gat | 3399 |
| Thr | Lys | Val | Thr | Asp | Leu | Ala | Leu | Pro | Gln | Thr | Thr | Ser | Trp | Asp |
| | 1040 | | | | | 1045 | | | | | 1050 | | | |

| aca | tgg | ggg | act | gct | acg | ttt | agc | gtc | tcg | ctg | agt | aca | ggt | ctc | 3444 |
| Thr | Trp | Gly | Thr | Ala | Thr | Phe | Ser | Val | Ser | Leu | Ser | Thr | Gly | Leu |
| | 1055 | | | | | 1060 | | | | | 1065 | | | |

| aac | acg | gtg | aaa | gtc | agc | tat | gat | ggt | acc | agt | tca | ctt | ggc | att | 3489 |
| Asn | Thr | Val | Lys | Val | Ser | Tyr | Asp | Gly | Thr | Ser | Ser | Leu | Gly | Ile |
| | 1070 | | | | | 1075 | | | | | 1080 | | | |

| aat | ttc | gat | aac | atc | gcg | att | gta | gag | caa | taa | aaggtcggga | 3532 |
| Asn | Phe | Asp | Asn | Ile | Ala | Ile | Val | Glu | Gln | | | |
| | 1085 | | | | | 1090 | | | | | | |

| gggcaagtcc | ctcccttaat | ttctaatcga | aagggagtat | ccttgatgcg | tccaccaaac | 3592 |
| aaagaaattc | cacgtattct | tgctttttt | acagcgttta | cgttgtttgg | ttcaacccctt | 3652 |
| gccttgcttc | ctgctccgcc | tgcgcatgcc | tatgtcagca | gcctagggga | aaatctcatt | 3712 |
| tcttcgagtg | tcaccggaga | taccttgacg | ctaactgttg | ataacggtgc | gccgagtgat | 3772 |
| gacctcttga | ttgttcaagc | ggtgcaaaac | ggtattttga | aggtggatta | tcgtccaaat | 3832 |
| agcataacgc | cgagcgcgaa | gacgccgatg | ctggatc | | | 3869 |